US012589234B2

(12) United States Patent
Varghai et al.

(10) Patent No.: US 12,589,234 B2
(45) Date of Patent: Mar. 31, 2026

(54) INTRAVASCULAR BLOOD PUMPS

(71) Applicant: SHIFAMED HOLDINGS, LLC, Campbell, CA (US)

(72) Inventors: Daniel Varghai, Campbell, CA (US); Ari Ryan, Sunnyvale, CA (US); Daniel Hildebrand, Santa Cruz, CA (US); Mostafa Ghoreyshi, Campbell, CA (US)

(73) Assignee: Supira Medical, Inc., Los Gatos, CA (US)

( * ) Notice: Subject to any disclaimer, the term of this patent is extended or adjusted under 35 U.S.C. 154(b) by 427 days.

(21) Appl. No.: 18/000,265

(22) PCT Filed: May 28, 2021

(86) PCT No.: PCT/US2021/034941
§ 371 (c)(1),
(2) Date: Nov. 29, 2022

(87) PCT Pub. No.: WO2021/243263
PCT Pub. Date: Dec. 2, 2021

(65) Prior Publication Data
US 2023/0201558 A1 Jun. 29, 2023

Related U.S. Application Data

(60) Provisional application No. 63/032,211, filed on May 29, 2020.

(51) Int. Cl.
*A61M 60/13* (2021.01)
*A61M 60/216* (2021.01)
(Continued)

(52) U.S. Cl.
CPC .......... *A61M 60/13* (2021.01); *A61M 60/216* (2021.01); *A61M 60/408* (2021.01); *A61M 60/818* (2021.01); *A61M 60/865* (2021.01)

(58) Field of Classification Search
None
See application file for complete search history.

(56) References Cited

U.S. PATENT DOCUMENTS

| | | | |
|---|---|---|---|
| 4,625,712 | A | 12/1986 | Wampler |
| 4,753,221 | A | 6/1988 | Kensey et al. |

(Continued)

FOREIGN PATENT DOCUMENTS

| | | |
|---|---|---|
| CA | 3014105 A1 | 8/2017 |
| EP | 3131599 A1 | 2/2017 |

(Continued)

OTHER PUBLICATIONS

Salahieh et al.; U.S. Appl. No. 19/256,688 entitled "Intravascular blood pumps and methods of use and manufacture," filed Jul. 1, 2025.

*Primary Examiner* — Mallika D Fairchild
(74) *Attorney, Agent, or Firm* — Shay Glenn LLP

(57) ABSTRACT
Catheter blood pumps that include collapsible blood conduits and one or more collapsible impellers. The catheter blood pumps include an outflow and an expandable flow diverter disposed in an outflow region. The expandable flow diverters can be completely proximal to a proximal end of the collapsible blood conduit.

17 Claims, 35 Drawing Sheets

(51) Int. Cl.
  *A61M 60/408*     (2021.01)
  *A61M 60/818*     (2021.01)
  *A61M 60/865*     (2021.01)

(56)             References Cited

U.S. PATENT DOCUMENTS

| | | | |
|---|---|---|---|
| 5,061,256 | A | 10/1991 | Wampler |
| 5,287,858 | A | 2/1994 | Hammerslag et al. |
| 5,507,629 | A | 4/1996 | Jarvik |
| 5,735,892 | A | 4/1998 | Myers et al. |
| 6,007,478 | A | 12/1999 | Siess et al. |
| 6,053,943 | A | 4/2000 | Edwin et al. |
| 6,685,696 | B2 | 2/2004 | Fleischhacker et al. |
| 6,712,844 | B2 | 3/2004 | Pacetti |
| 7,022,100 | B1 | 4/2006 | Hosn et al. |
| 7,027,875 | B2 | 4/2006 | Siess et al. |
| 7,220,275 | B2 | 5/2007 | Davidson et al. |
| 7,828,710 | B2 | 11/2010 | Shifflette |
| 7,841,976 | B2 | 11/2010 | McBride et al. |
| 8,388,565 | B2 | 3/2013 | Shifflette |
| 8,485,961 | B2 | 7/2013 | Campbell et al. |
| 8,535,211 | B2 | 9/2013 | Campbell et al. |
| 8,591,393 | B2 | 11/2013 | Walters et al. |
| 8,597,170 | B2 | 12/2013 | Walters et al. |
| 8,721,517 | B2 | 5/2014 | Zeng et al. |
| 8,734,508 | B2 | 5/2014 | Hastings et al. |
| 8,814,776 | B2 | 8/2014 | Hastie et al. |
| 8,814,933 | B2 | 8/2014 | Siess |
| 8,849,398 | B2 | 9/2014 | Evans |
| 8,932,141 | B2 | 1/2015 | Liebing |
| 8,934,956 | B2 | 1/2015 | Glenn et al. |
| 9,028,216 | B2 | 5/2015 | Schumacher et al. |
| 9,028,392 | B2 | 5/2015 | Shifflette |
| 9,072,825 | B2 | 7/2015 | Pfeffer et al. |
| 9,138,518 | B2 | 9/2015 | Campbell et al. |
| 9,180,235 | B2 | 11/2015 | Forsell |
| 9,446,179 | B2 | 9/2016 | Keenan et al. |
| 9,512,839 | B2 | 12/2016 | Liebing |
| 9,833,550 | B2 | 12/2017 | Siess |
| 9,872,948 | B2 | 1/2018 | Siess |
| 10,052,419 | B2 | 8/2018 | Er |
| 10,208,763 | B2 | 2/2019 | Schumacher et al. |
| 10,357,598 | B2 | 7/2019 | Aboul-Hosn et al. |
| 10,722,631 | B2 | 7/2020 | Salahieh et al. |
| 10,881,770 | B2 | 1/2021 | Tuval et al. |
| 10,894,115 | B2 | 1/2021 | Pfeffer et al. |
| 11,268,521 | B2 | 3/2022 | Toellner |
| 11,280,345 | B2 | 3/2022 | Bredenbreuker et al. |
| 11,850,413 | B2 | 12/2023 | Zeng et al. |
| 12,017,056 | B2 | 6/2024 | Guo et al. |
| 2005/0277803 | A1 | 12/2005 | Pecor |
| 2007/0250148 | A1 | 10/2007 | Perry et al. |
| 2014/0148638 | A1 | 5/2014 | LaRose et al. |
| 2015/0238671 | A1 | 8/2015 | Mesallum |
| 2015/0328382 | A1 | 11/2015 | Corbett et al. |
| 2015/0335803 | A1 | 11/2015 | Yamane |
| 2016/0022890 | A1 | 1/2016 | Schwammenthal et al. |
| 2016/0053763 | A1 | 2/2016 | Toellner |
| 2017/0014562 | A1 | 1/2017 | Liebing |
| 2017/0037860 | A1 | 2/2017 | Toellner |
| 2017/0100527 | A1 | 4/2017 | Schwammenthal et al. |
| 2017/0173242 | A1 | 6/2017 | Anderson et al. |
| 2017/0232169 | A1 | 8/2017 | Muller |
| 2017/0340788 | A1 | 11/2017 | Korakianitis et al. |
| 2018/0080326 | A1 | 3/2018 | Schumacher et al. |
| 2018/0149164 | A1 | 5/2018 | Siess |
| 2018/0303990 | A1 | 10/2018 | Siess et al. |
| 2019/0143018 | A1* | 5/2019 | Salahieh ............ A61M 60/825 600/16 |
| 2019/0328948 | A1* | 10/2019 | Salahieh ............ A61M 60/808 |
| 2020/0030510 | A1 | 1/2020 | Higgins |
| 2020/0121835 | A1 | 4/2020 | Farago et al. |
| 2020/0237981 | A1 | 7/2020 | Tuval et al. |
| 2020/0316268 | A1 | 10/2020 | Antoni et al. |
| 2022/0203084 | A1 | 6/2022 | Zarins et al. |

FOREIGN PATENT DOCUMENTS

| | | |
|---|---|---|
| EP | 3153190 A1 | 4/2017 |
| WO | WO01/019444 A1 | 3/2001 |
| WO | WO2005/020848 A2 | 3/2005 |
| WO | WO2009/046789 A1 | 4/2009 |
| WO | WO2015/177793 A2 | 11/2015 |
| WO | WO2017/060257 A1 | 4/2017 |
| WO | WO2018/061002 A1 | 4/2018 |
| WO | WO2018/067410 A1 | 4/2018 |
| WO | WO2018/078615 A1 | 5/2018 |
| WO | WO2018/088939 A1 | 5/2018 |
| WO | WO2018/096531 A1 | 5/2018 |
| WO | WO2019/191851 A1 | 9/2019 |
| WO | WO2019/194956 A1 | 10/2019 |

* cited by examiner

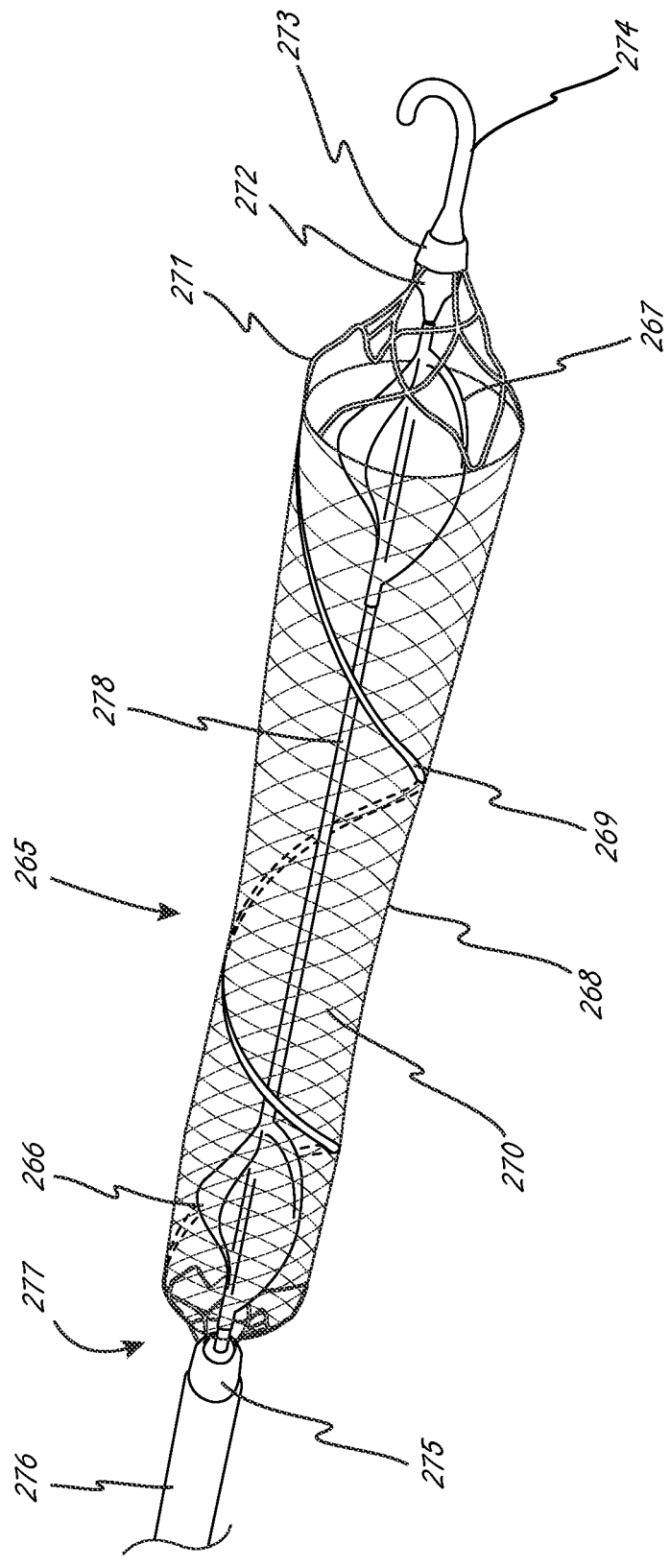
273
274
272
271
267
278
265
269
268
266
277
270
275
276
*Fig. 5* different pitch than

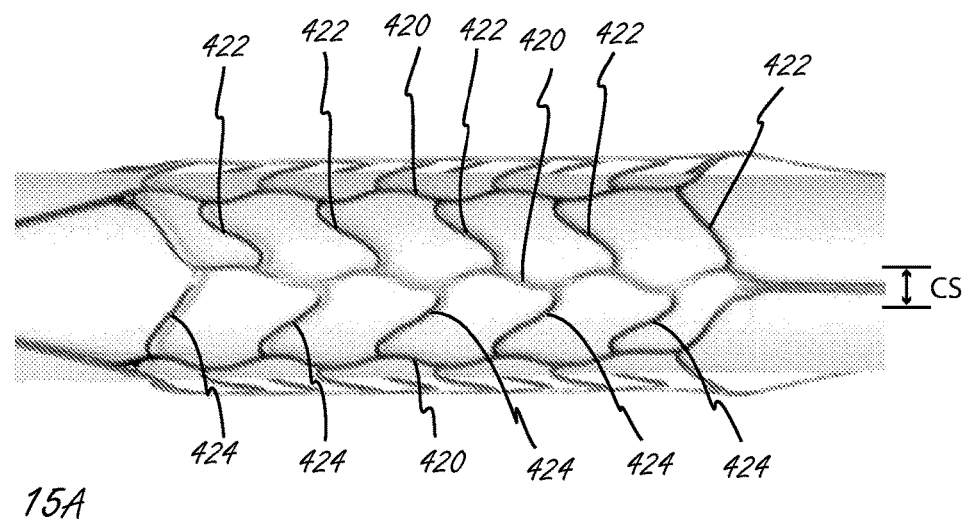
*Fig. 15A*
*Fig. 15B*
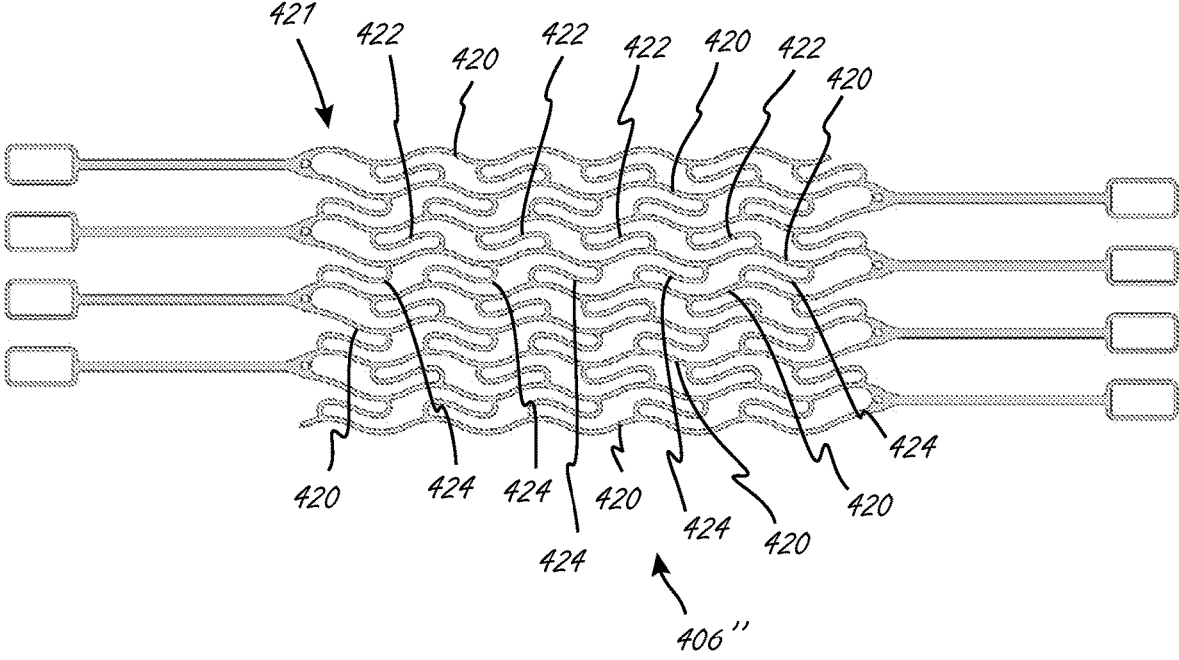

Fi. 23B

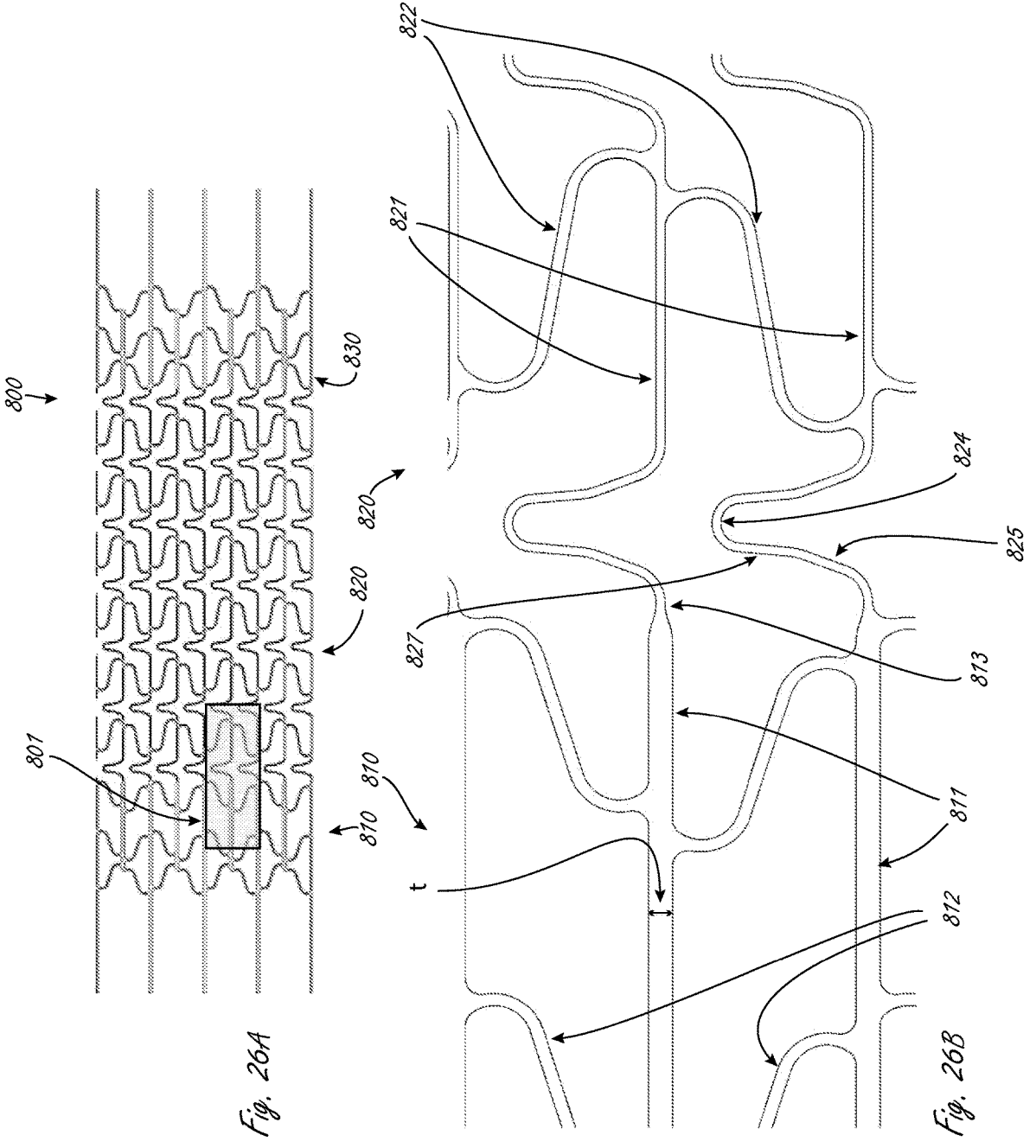

Distal

Proximal

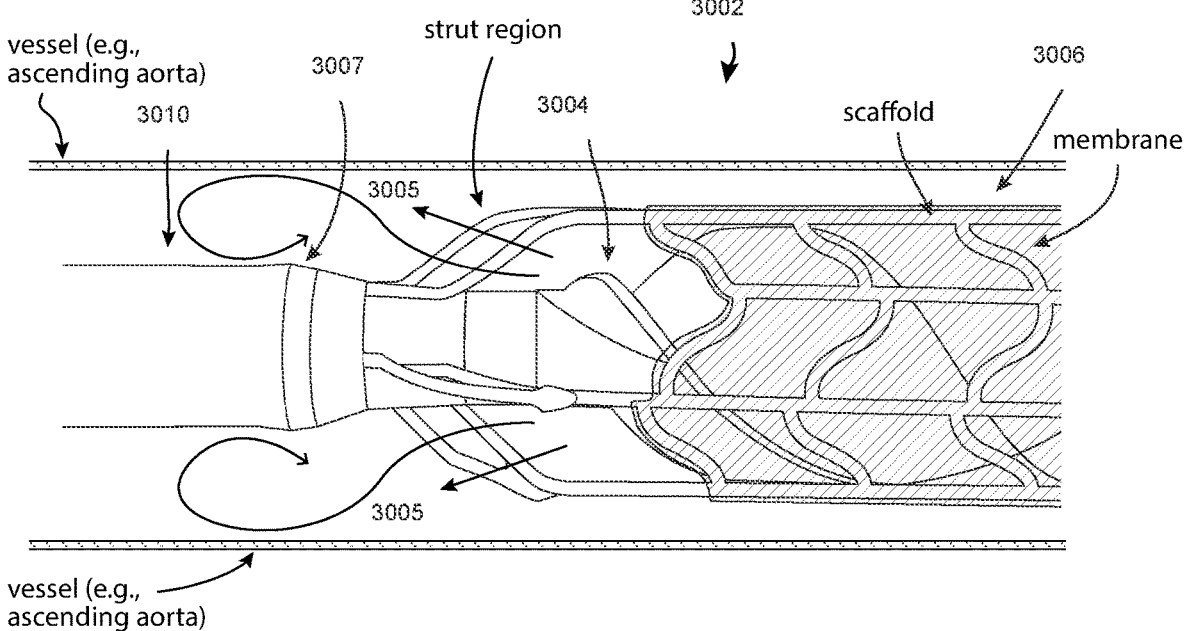
*Fig.* 30

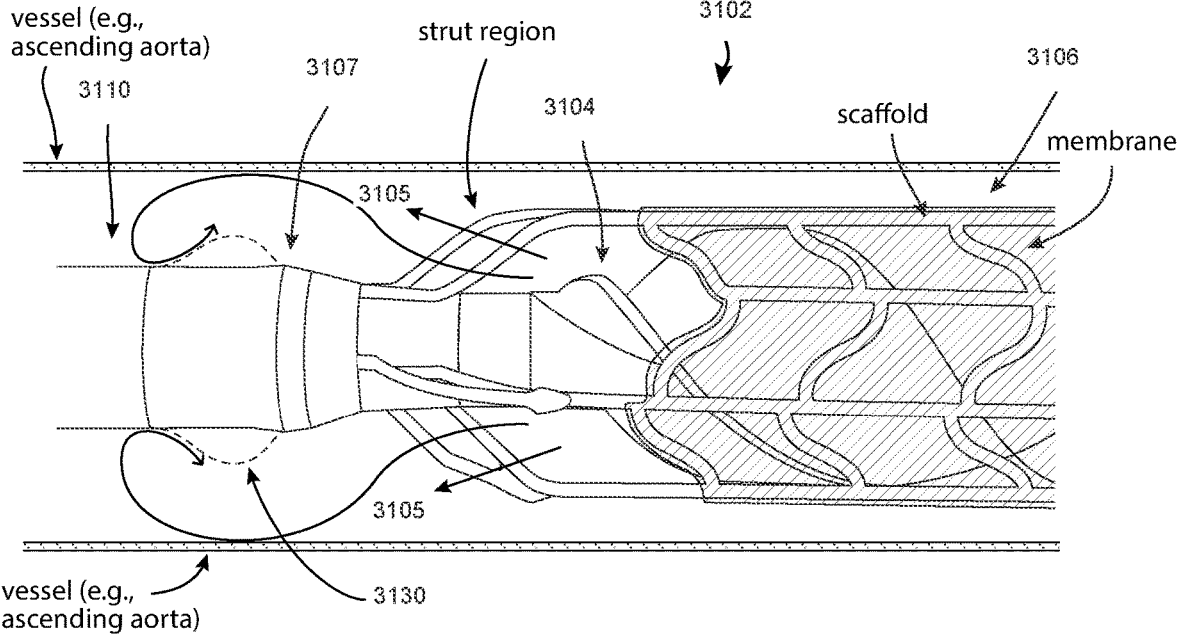
*Fig.* 31

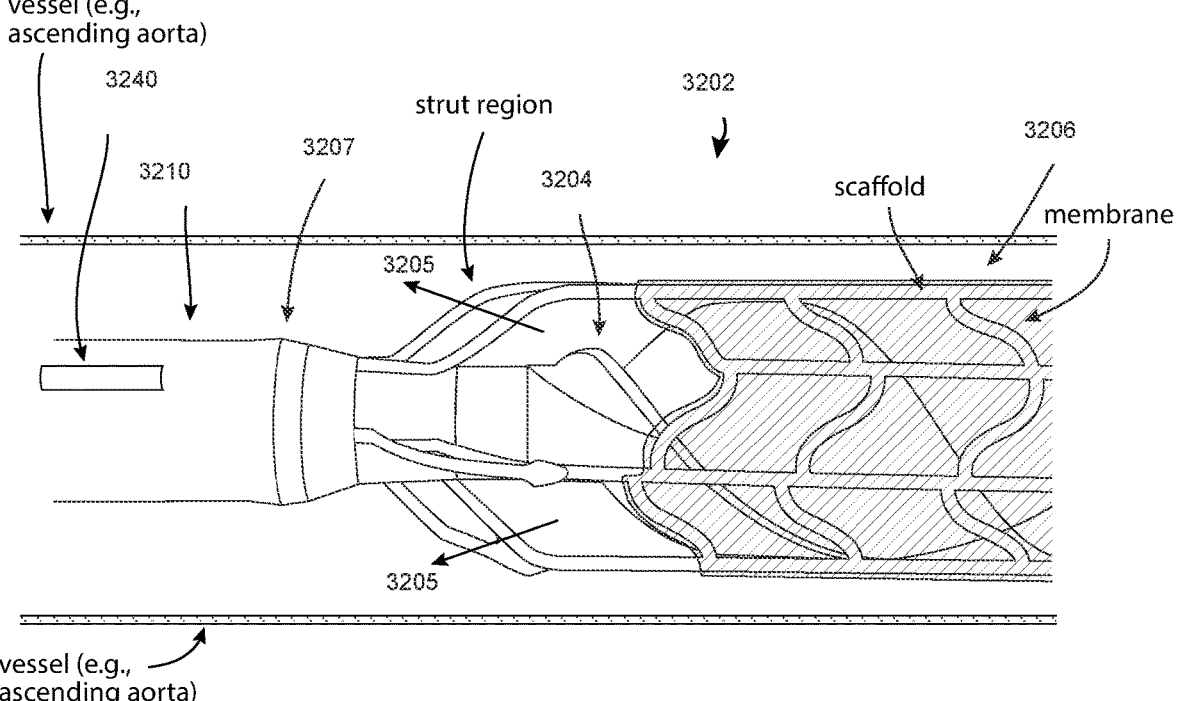
*Fig.* 32

INTRAVASCULAR BLOOD PUMPS

CROSS REFERENCE TO RELATED APPLICATIONS

This application claims priority to U.S. Prov. App. 63/032,211, filed May 29, 2020, the entire disclosures of which are incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

This application also incorporates by reference herein the following applications in their entireties for all purposes: WO 2018/226991; WO2019/094963; WO2019/152875; PCT/US2019/044432; and PCT/US2019/055038.

BACKGROUND

Intravascular blood pumps may benefit from being collapsible to facilitate a smaller delivery profile, yet may be adapted to be expanded to a larger radial dimension at a target location within a subject, and operated to facilitate the movement of blood.

Pump features and configurations are generally desired that can provide desired pump performance, including without limitation flow rate, while maintaining hemolysis within acceptable limits.

SUMMARY OF THE DISCLOSURE

One aspect of the disclosure is a method of directing outflow of an intravascular blood pump. The method can include expanding a collapsible blood pump from a collapsed configuration at a location within a subject, the expanding step including expanding a collapsible fluid conduit from a collapsed configuration and expanding one or more collapsible impellers; expanding an expandable flow diverter into an expanded configuration in which at least a portion of the flow diverter is disposed proximal to the fluid conduit; and rotating the at least one impeller to cause blood to move from a fluid conduit distal end towards the fluid conduit proximal end.

One aspect of the disclosure is an intravascular blood pump that includes a pump portion comprising a collapsible fluid conduit and one or more collapsible impellers, and an expandable flow diverter comprising a flow diverting surface, the flow diverting surface disposed proximal to (optionally completely proximal to) a proximal end of the fluid conduit and proximal to the one or more impellers when the flow diverter is in an expanded configuration.

One aspect of the disclosure is an intravascular blood pump that includes a pump portion comprising a collapsible fluid conduit, one or more collapsible impellers, and one or more proximal fluid conduit struts extending proximally from the fluid conduit; an expandable flow diverter comprising a flow diverting surface, the flow diverter having an expanded configuration in which at least a portion of the flow diverter is disposed proximal to the fluid conduit, and wherein a portion of each of the one or more proximal fluid conduit struts are secured to the expandable flow diverter.

One aspect of the disclosure is an intravascular blood pump that includes a pump portion comprising a collapsible fluid conduit and one or more collapsible impellers; and an expandable flow diverter comprising a flow diverting surface, the flow diverter having an expanded configuration in which at least a portion of the flow diverter is disposed proximal to the fluid conduit, the expandable flow diverter having an expanded configuration in which a radially outermost dimension of the flow diverter is at least 25% of a radially outermost dimension of the one or more impellers, optionally at least 50%, optionally at least 55%, optionally at least 60%, optionally at least 65%, optionally at least 70%, optionally at least 75%, optionally at least 80%, optionally at least 85%, optionally at least 90%, optionally at least 95%, optionally at least 100%, and optionally no more than 300%.

Flow diverting surfaces herein may be configured and positioned to increase a radial flow component of the blood at a location proximal to the proximal end of the collapsible fluid conduit, the increase relative to flow without the flow diverting surface.

Flow diverters herein can be rotationally uncoupled from the one or more impellers.

A radial dimension of a flow diverting surface herein can increase in an axial distal-to-proximal direction.

Flow diverters herein may include a proximal surface proximal to a flow diverting surface, the proximal surface having a radial dimension that decreases in an axial distal-to-proximal direction.

A pump herein can further comprise a plurality of proximal fluid conduit struts extending proximally from the fluid conduit.

A portion of each of the struts may be secured to a flow diverter (e.g., to a proximal surface of the flow diverter), and a portion of each of the struts (e.g., a distal portion of the struts) may not be secured to the flow diverter.

Flow diverters herein may have a bulbous expanded configuration.

A portion of impellers herein may extend proximally from a fluid conduit proximal end.

Flow diverters herein can comprise a deformable material that allows the flow diverter to at least partially self-expand when released from a sheathing force.

An inner volume of flow diverters herein may be in fluid communication with an inflation lumen extending axially through the blood pump, wherein the inflation lumen can be coupleable to a fluid source.

Flow diverters herein, in expanded configurations, may have a radially outermost dimension that is at least 25% of a radially outermost dimension of the expanded impeller, optionally at least 50%, optionally at least 55%, optionally at least 60%, optionally at least 65%, optionally at least 70%, optionally at least 75%, optionally at least 80%, optionally at least 85%, optionally at least 90%, optionally at least 95%, optionally at least 100%, and optionally no more than 300%.

One aspect of the disclosure is an intravascular blood pump that includes a collapsible pump portion that includes a collapsible blood conduit and one or more collapsible impellers, the blood conduit having a proximal end with a non-circular configuration.

In this aspect, the collapsible fluid conduit may include a support member and a layer secured relative to the support member, the layer at least partially defining a fluid lumen, wherein a layer proximal end has a configuration that is non-circular. A layer proximal end may define the blood conduit proximal end. A support member proximal end may have a configuration that is non-circular. A layer proximal end may follow a support member proximal end. A layer proximal end may have an undulating configuration. A layer proximal end may not follow a support member proximal end around the entire blood conduit proximal end. A layer proximal end may have a configuration that includes a plurality of protrusions having peaks that extend proximally Optionally not all of the plurality of protrusions extend to the same location proximally One aspect of the disclosure is an intravascular blood pump including a blood conduit having a proximal end defined by alternating protrusions and depressions, with the protrusions protruding in a proximal direction. Each one of a plurality of struts may extend from one of the plurality of protrusions. A proximal impeller may axially overlap with the protrusions and depressions. A proximal impeller may extend further proximally than proximal ends of the protrusions.

BRIEF DESCRIPTION OF THE DRAWINGS

FIG. 5 illustrates an exemplary pump portion including an expandable impeller housing, a blood conduit, and a plurality of impellers.

FIG. 15A illustrates an exemplary expanded scaffold that may be part of any of the expandable pump portions herein.

FIG. 15B illustrates the scaffold and struts from FIG. 15A in a flattened and non-expanded configuration.

FIG. 23B illustrates the scaffold from FIG. 23A in an expanded configuration.

FIG. 26A illustrates an exemplary scaffold in a flattened and non-expanded configuration.

FIG. 26B highlights an exemplary section of the scaffold shown in FIG. 26A.

FIG. 30 illustrates an exemplary outflow region of a pump portion of a catheter blood pump.

FIG. 31 illustrates an exemplary outflow region of a pump portion of a catheter blood pump.

FIG. 32 illustrates an exemplary outflow region of a pump portion of a catheter blood pump.

DESCRIPTION

The present disclosure is related to medical devices, systems, and methods of use and manufacture. Medical devices herein may include a distal pump portion (which may also be referred to herein as a working portion) adapted to be disposed within a physiologic vessel, wherein the distal pump portion includes one or more components that act upon fluid. For example, pump portions herein may include one or more rotating members that when rotated, can facilitate the movement of a fluid such as blood.

Any of the disclosure herein relating to an aspect of a system, device, or method of use can be incorporated with any other suitable disclosure herein. For example, a figure describing only one aspect of a device or method can be included with other embodiments even if that is not specifically stated in a description of one or both parts of the disclosure. It is thus understood that combinations of different portions of this disclosure are included herein.

Figure 1:
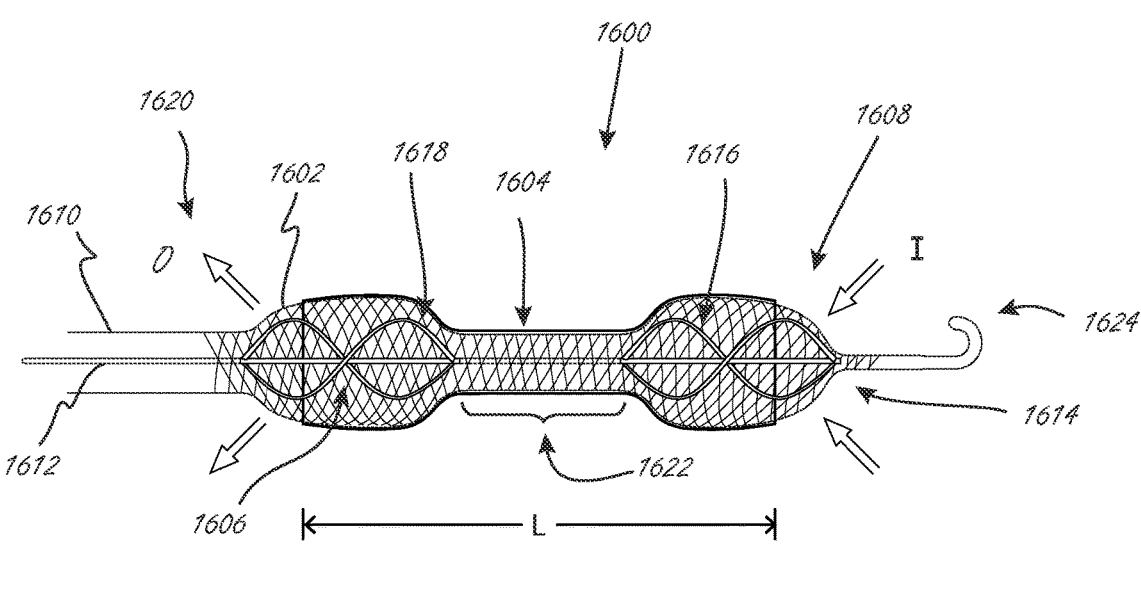
FIG. 1 is a side view of an exemplary expandable pump portion that includes an expandable impeller housing that includes a scaffold and blood conduit, and a plurality of impellers.

FIG. 1 is a side view illustrating a distal portion of an exemplary catheter blood pump, including pump portion 1600, wherein pump portion 1600 includes proximal impeller 1606 and distal impeller 1616, both of which are in operable communication with drive cable 1612. Pump portion 1600 is in an expanded configuration in FIG. 1, but is adapted to be collapsed to a delivery configuration so that it can be delivered with a lower profile. The impellers can be attached to drive mechanism 1612 (e.g., a drive cable). Drive mechanism 1612 is in operable communication with an external motor, not shown, and extends through elongate shaft 1610. The phrases "pump portion" and "working portion" (or derivatives thereof) may be used herein interchangeably unless indicated to the contrary. For example without limitation, "pump portion" 1600 can also be referred to herein as a "working portion."

Pump portion 1600 also includes expandable member or expandable scaffold 1602, which in this embodiment has a proximal end 1620 that extends further proximally than a proximal end of proximal impeller 1606, and a distal end 1608 that extends further distally than a distal end 1614 of distal impeller 1616. Expandable members may also be referred to herein as expandable scaffolds or scaffold sections. Expandable scaffold 1602 is disposed radially outside of the impellers along the axial length of the impellers. Expandable scaffold 1602 can be constructed in a manner and made from materials similar to many types of expandable structures that are known in the medical arts to be able to collapsed and expanded, examples of which are provided herein. Examples of suitable materials include, but are not limited to, polyurethane, polyurethane elastomers, metallic alloys, etc.

Pump portion 1600 also includes blood conduit 1604, which is coupled to and supported by expandable member 1602, has a length L, and extends axially between the impellers. Conduit 1604 creates and provides a fluid lumen between the two impellers. When in use, fluid moves through the lumen defined by conduit 1604. The conduits herein may be non-permeable, or they may be semi-permeable, or even porous as long as they still define a lumen. The conduits herein are also flexible, unless otherwise indicated.

The conduits herein extend completely around (i.e., 360 degrees) at least a portion of the pump portion. In pump portion 1600, the conduit extends completely around expandable member 1602, but does not extend all the way to the proximal end 1602 or distal end 1608 of expandable member 1602. The structure of the expandable member creates at least one inlet aperture to allow for inflow "I," and at least one outflow aperture to allow for outflow "O." Conduit 1604 improves impeller pumping dynamics, compared to pump portions without a conduit. As described herein, expandable members or scaffolds may also be considered to be a part of the blood conduit generally, which together define a blood lumen. In these instances the scaffold and material supported by the scaffold may be referred to herein as an expandable impeller housing or housing.

Expandable member 1602 may have a variety of constructions, and made from a variety of materials. For example, expandable member 1602 may be formed similar to expandable stents or stent-like devices, or any other example provided herein. For example without limitation, expandable member 1602 could have an open-braided construction, such as a 24-end braid, although more or fewer braid wires could be used. Exemplary materials for the expandable member as well as the struts herein include nitinol, cobalt alloys, and polymers, although other materials could be used. Expandable member 1602 has an expanded configuration, as shown, in which the outer dimension (measured orthogonally relative a longitudinal axis of the working portion) of the expandable member is greater in at least a region where it is disposed radially outside of the impellers than in a central region 1622 of the expandable member that extends axially between the impeller. Drive mechanism 1612 is co-axial with the longitudinal axis in this embodiment. In use, the central region can be placed across a valve, such as an aortic valve. In some embodiments, expandable member 1602 is adapted and constructed to expand to an outermost dimension of 12-24 F(4.0-8.0 mm) where the impellers are axially within the expandable member, and to an outermost dimension of 10-20 F (3.3-6.7 mm) in central region 1622 between the impellers. The smaller central region outer dimension can reduce forces acting on the valve, which can reduce or minimize damage to the valve. The larger dimensions of the expandable member in the regions of the impellers can help stabilize the working portion axially when in use. Expandable member 1602 has a general dumbbell configuration. Expandable member 1602 has an outer configuration that tapers as it transitions from the impeller regions to central region 1622, and again tapers at the distal and proximal ends of expandable member 1602.

Expandable member 1602 has a proximal end 1620 that is coupled to shaft 1610, and a distal end 1608 that is coupled to distal tip 1624. The impellers and drive mechanism 1612 rotate within the expandable member and conduit assembly. Drive mechanism 1612 is axially stabilized with respect to distal tip 1624, but is free to rotate with respect to tip 1624.

In some embodiments, expandable member 1602 can be collapsed by pulling tension from end-to-end on the expandable member. This may include linear motion (such as, for example without limitation, 5-20 mm of travel) to axially extend expandable member 1602 to a collapsed configuration with collapsed outer dimension(s). Expandable member 1602 can also be collapsed by pushing an outer shaft such as a sheath over the expandable member/conduit assembly, causing the expandable member and conduit to collapse towards their collapsed delivery configuration.

Impellers 1606 and 1616 are also adapted and constructed such that one or more blades will stretch or radially compress to a reduced outermost dimension (measured orthogonally to the longitudinal axis of the working portion). For example without limitation, any of the impellers herein can include one or more blades made from a plastic formulation with spring characteristics, such as any of the impellers described in U.S. Pat. No. 7,393,181, the disclosure of which is incorporated by reference herein for all purposes and can be incorporated into embodiments herein unless this disclosure indicates to the contrary. Alternatively, for example, one or more collapsible impellers can comprise a superelastic wire frame, with polymer or other material that acts as a webbing across the wire frame, such as those described in U.S. Pat. No. 6,533,716, the disclosure of which is incorporated by reference herein for all purposes.

The inflow and/or outflow configurations of working portion 1600 can be mostly axial in nature.

Exemplary sheathing and unsheathing techniques and concepts to collapse and expand medical devices are known, such as, for example, those described and shown in U.S. Pat. No. 7,841,976 or U.S. Pat. No. 8,052,749, the disclosures of which are incorporated by reference herein.

Figure 2:
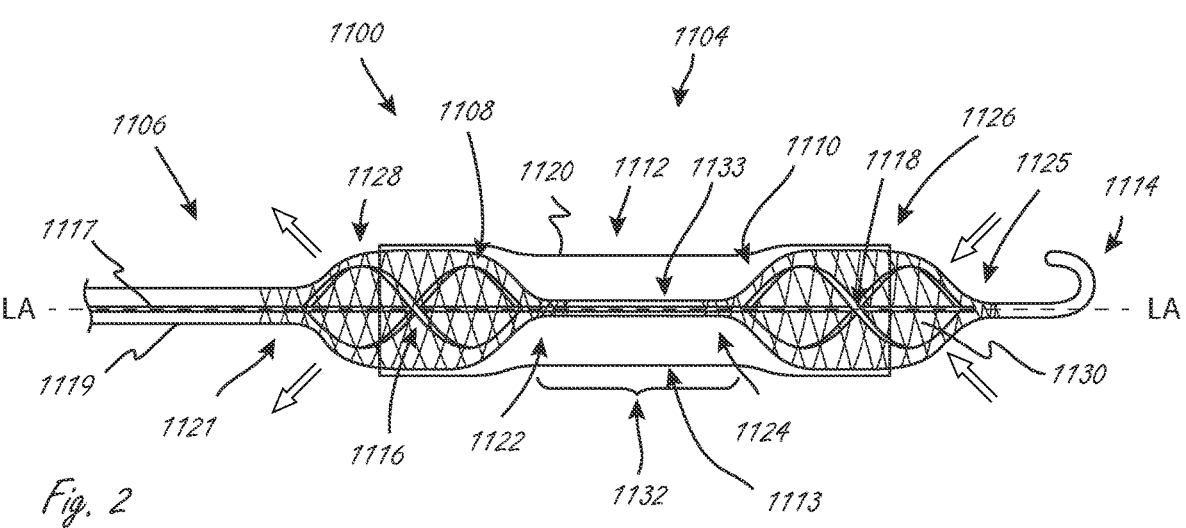
FIG. 2 is a side view of an exemplary expandable pump portion that includes an expandable impeller housing, a blood conduit, a plurality of impellers, and a plurality of expandable scaffolds sections or support members.

FIG. 2 is a side view illustrating a deployed configuration (shown extracorporeally) of a distal portion of an exemplary embodiment of a catheter blood pump. Exemplary blood pump 1100 includes working portion 1104 (which as set forth herein may also be referred to herein as a pump portion) and an elongate portion 1106 extending from working portion 1104. Elongate portion 1106 can extend to a more proximal region of the system, not shown for clarity, and that can include, for example, a motor. Working portion 1104 includes first expandable scaffold or member 1108 and second expandable scaffold or member 1110, axially spaced apart along a longitudinal axis LA of working portion 1104. First scaffold 1108 and second scaffold 1110 (and any other separate scaffolds herein) may also be referenced as part of a common scaffold and referred to herein as scaffold sections. Spaced axially in this context refers to the entire first expandable member being axially spaced from the entire second expandable member along a longitudinal axis LA of working portion 1104. A first end 1122 of first expandable member 1108 is axially spaced from a first end 1124 of second expandable member 1110.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Working portion 1104 also includes blood conduit 1112 that is coupled to first expandable member 1108 and to second expandable member 1110, and extends axially in between first expandable member 1108 and second expandable member 1110 in the deployed configuration. A central region 1113 of conduit 1112 spans an axial distance 1132 where the working portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a blood conduit being coupled to an expandable scaffold or member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations.

Any of the blood conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as working portion 1104 is deployed towards the configuration shown in FIG. 2. The conduit may be stretched tightly between the expandable members in some embodiments. The conduit may alternatively be designed with a looseness that causes a greater degree of compliance. This can be desirable when the working portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the blood conduits herein, or at least a portion of the conduit, can be impermeable to blood. In FIG. 2, working portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable scaffolds or members help maintain the blood conduit in an open configuration to create the lumen, while each also creates a working environment for an impeller, described below. Each of the expandable scaffolds, when in the deployed configuration, is maintained in a spaced relationship relative to a respective impeller, which allows the impeller to rotate within the expandable member without contacting the expandable member. Working portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the working portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and working portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Working portion 1104 is adapted and configured to be collapsed to a smaller profile than its deployed configuration (which is shown in FIG. 2). This allows it to be delivered using a lower profile delivery device (smaller French size) than would be required if none of working portion 1104 was collapsible. Even if not specifically stated herein, any of the expandable members and impellers may be adapted and configured to be collapsible to some extent to a smaller delivery configuration.

The working portions herein can be collapsed to a collapsed delivery configuration using conventional techniques, such as with an outer sheath that is movable relative to the working portion (e.g., by axially moving one or both of the sheath and working portion). For example without limitation, any of the systems, devices, or methods shown in the following references may be used to facilitate the collapse of a working portions herein: U.S. Pat. No. 7,841, 976 or 8,052,749, the disclosures of which are incorporated by reference herein for all purposes.

Figures 3A, 3B:
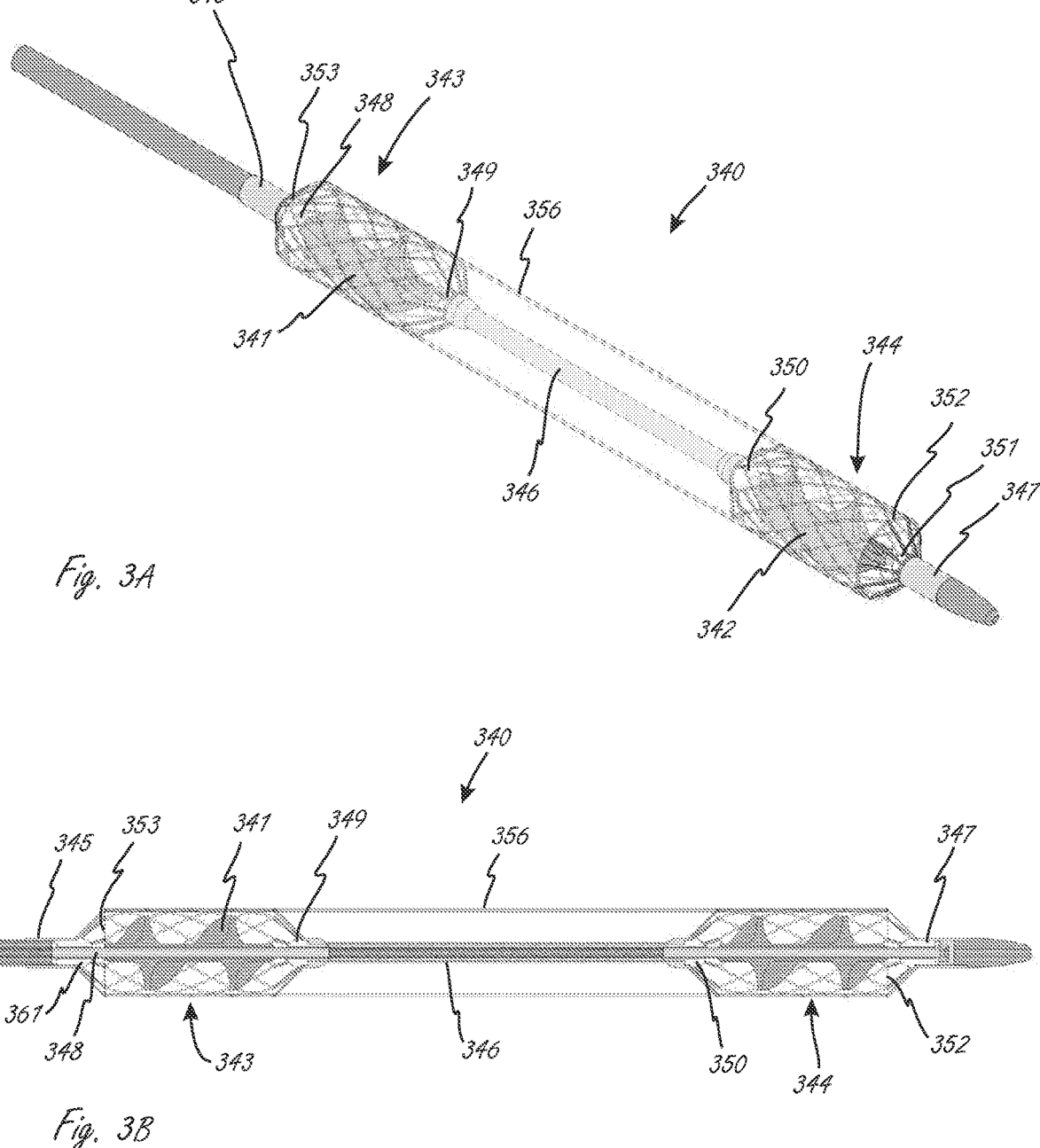
FIGS. 3A, 3B, 3C and 3D illustrate an exemplary expandable pump portion that includes a blood conduit, a plurality of impellers, and a plurality of expandable scaffold sections or support members.
Figure 3C:
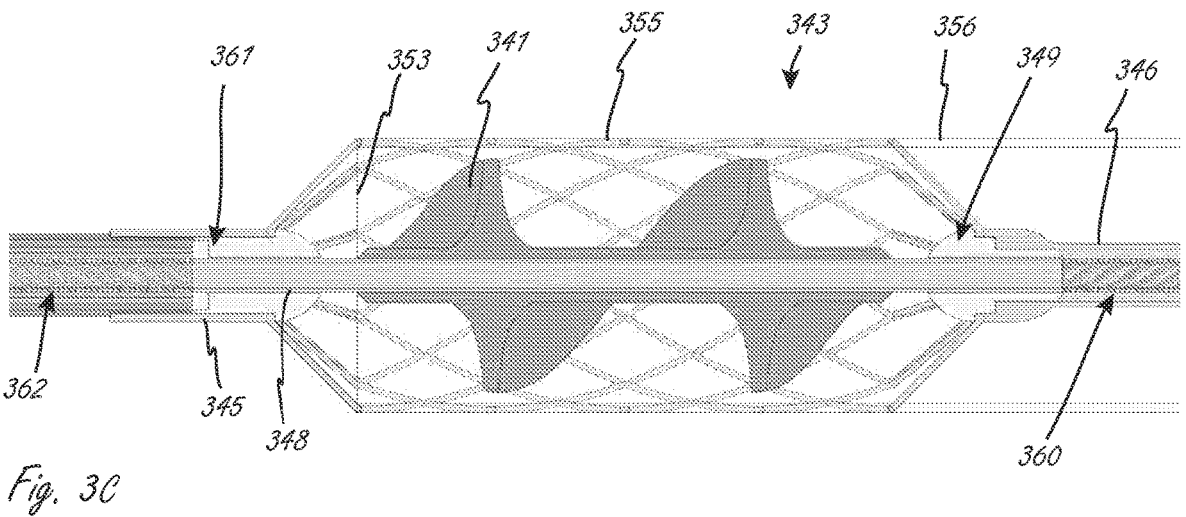
Figure 3D:
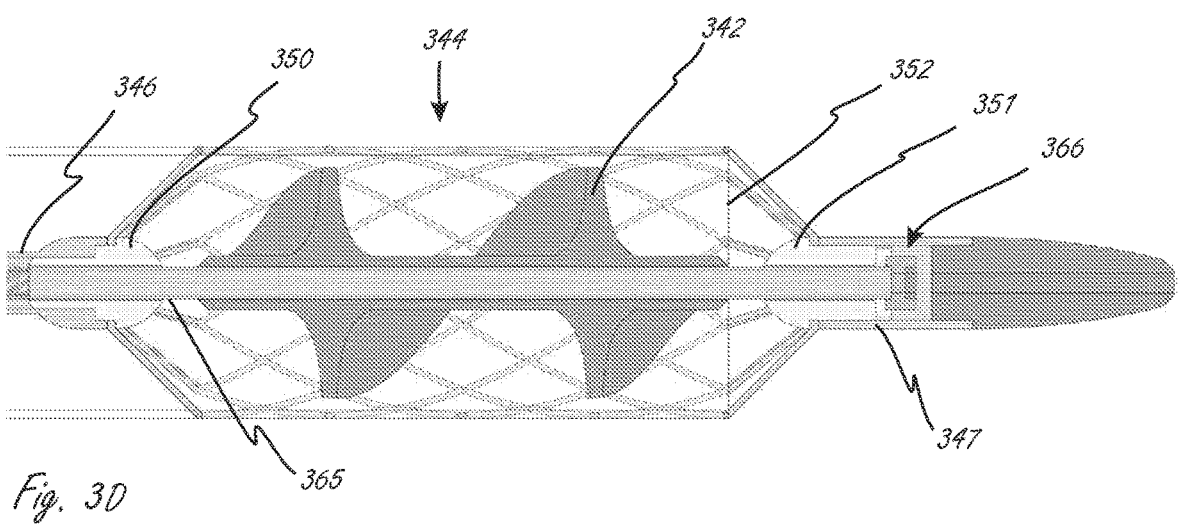

FIGS. 3A-3D show an exemplary pump portion that is similar in some ways to the pump portion shown in FIG. 2. Pump portion 340 is similar to pump portion 1104 in that in includes two expandable members axially spaced from one another when the pump portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Pump portion 340 includes proximal impeller 341 and distal impeller 342, which are coupled to and in operational communication with a drive cable, which defines therein a lumen. The lumen can be sized to accommodate a guidewire, which can be used for delivery of the working portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter.

The drive cable sections can be secured to each other using known attachment techniques. A distal end of fourth section 365 extends to a distal region of the working portion, allowing the working portion to be, for example, advanced over a guidewire for positioning the working portion. In this embodiment the second and fourth sections can be stiffer than first and third sections. For example, second and fourth can be tubular and first and third sections can be wound material to impart less stiffness.

Pump portion 340 includes proximal expandable scaffold 343 and distal expandable scaffold 344, each of which extends radially outside of one of the impellers. The expandable scaffolds have distal and proximal ends that also extend axially beyond distal and proximal ends of the impellers, which can be seen in FIGS. 3B-3D. Coupled to the two expandable scaffolds is blood conduit 356, which has a proximal end 353 and a distal end 352. The two expandable scaffolds each include a plurality of proximal struts and a plurality of distal struts. The proximal struts in proximal expandable scaffold 343 extend to and are secured to shaft section 345, which is coupled to bearing 361, through which the drive cable extends and is configured and sized to rotate. The distal struts of proximal expandable scaffold 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts extend axially from distal expandable scaffold 344 to and are secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts extend from the distal expandable scaffold extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
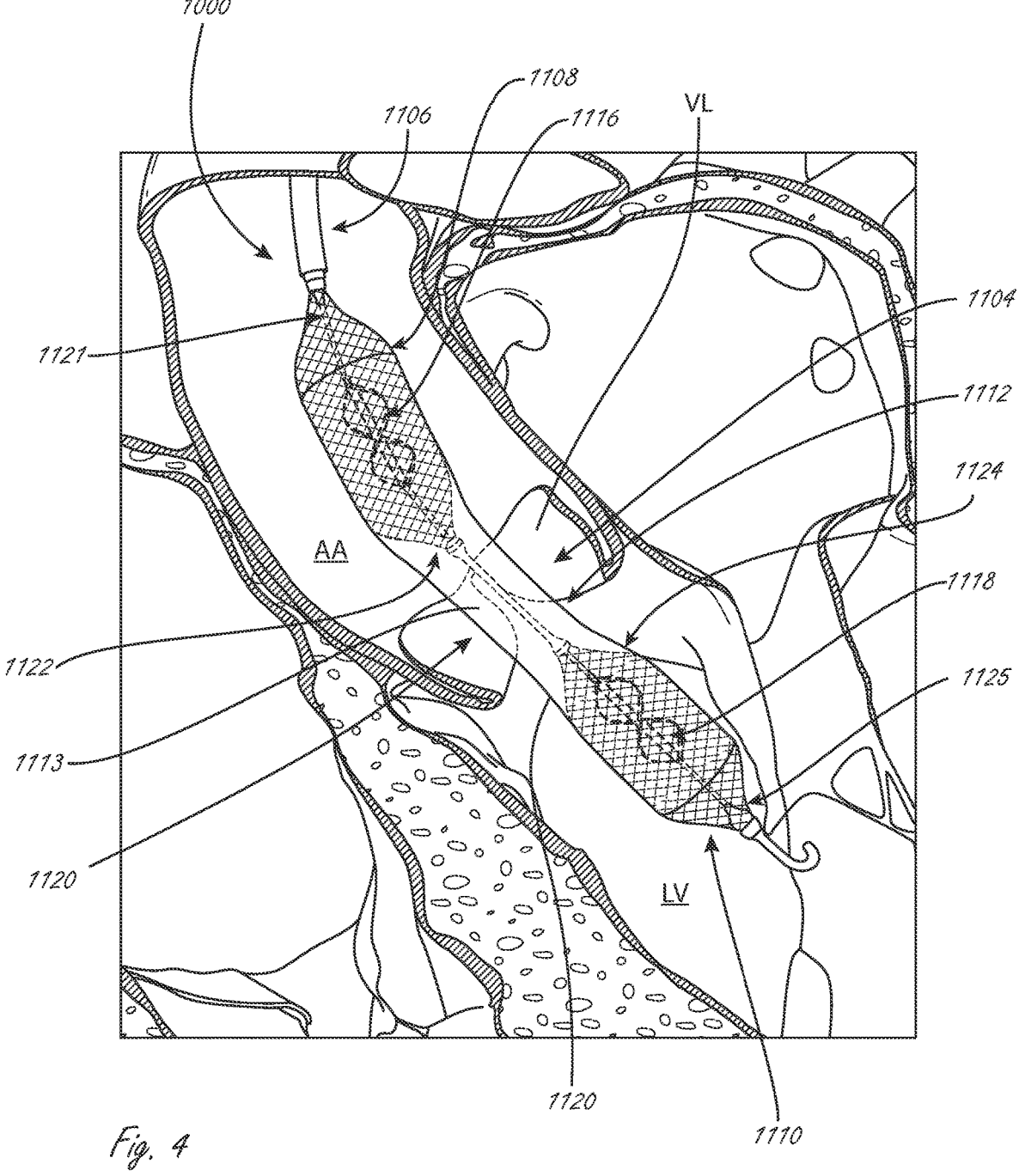
FIG. 4 illustrates an exemplary target location of an expandable pump portion, the pump portion including a blood conduit, a plurality of expandable scaffold sections or support members, and a plurality of impellers.

FIG. 4 illustrates an exemplary placement of pump portion 1104 from catheter blood pump 1000 from FIG. 2. Once difference shown in FIG. 4 is that the conduit extends at least as far as the ends of the impellers, like in FIGS. 3A-3D. FIG. 4 shows pump portion 1104 in a deployed configuration, positioned in place across an aortic valve. Pump portion 1104 can be delivered as shown via, for example without limitation, femoral artery access (a known access procedure). While not shown for clarity, system 1000 can also include an outer sheath or shaft in which working portion 1104 is disposed during delivery to a location near an aortic valve. The sheath or shaft can be moved proximally (towards the ascending aorta "AA" and away from left ventricle "LV") to allow for deployment and expansion of working portion 1104. For example, the sheath can be withdrawn to allow for expansion of second expandable scaffold 1110, with continued proximal movement allowing first expandable scaffold 1108 to expand.

In this embodiment, second expandable scaffold 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable scaffolds 1108 and 1110 causes blood conduit 1112 to assume a more open configuration, as shown in FIG. 4. Thus, while in this embodiment conduit 1112 does not have the same self-expanding properties as the expandable scaffolds, the conduit will assume a deployed, more open configuration when the working end is deployed. At least a portion of central region 1113 of conduit 1112 is positioned at an aortic valve coaptation region and engages leaflets. In FIGS. 3, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable scaffold 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of pump portion 1104, the position of the pump portion can be assessed in any way, such as under fluoroscopy. The position of the pump portion can be adjusted at any time during or after deployment. For example, after second expandable scaffold 1110 is released but before first expandable member 1108 is released, pump portion 1104 can be moved axially (distally or proximally) to reposition the pump portion. Additionally, for example, the pump portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or U.S. Pat. No. 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the working portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the expandable baskets, which can allow for more deformation of the working portion at the location of the leaflets than would occur if an expandable member spanned the aortic valve leaflets. This can cause less damage to the leaflets after the working portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9 F sheath and still obtain high enough flow rates when in use, which is not possible with some products currently in development and/or testing. For example, some products are too large to be able to be reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

The embodiment herein can thus achieve a smaller delivery profile while maintaining sufficiently high flow rates, while creating a more deformable and flexible central region of the working portion, the exemplary benefits of which are described above (e.g., interfacing with delicate valve leaflets).

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable scaffold or member, referred to 270 generally, and blood conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member. Helical tension member 269 (or a helical arrangement of expandable member cells) will act as a collective tension member and is configured so that when the expandable basket is pulled in tension along its length to collapse (such as by stretching to a much greater length, such as approximately doubling in length) tension member 269 is pulled into a straighter alignment, which causes rotation/twisting of the desired segment(s) of the expandable member during collapse, which causes the impeller blades to wrap radially inward as the expandable member and blades collapse. An exemplary configuration of such a tension member would have a curvilinear configuration when in helical form that is approximately equal to the maximum length of the expandable member when collapsed. In alternative embodiments, only the portion(s) of the expandable member that encloses a collapsible impeller is caused to rotate upon collapse.

There are alternative ways to construct the working portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the blood conduits herein act to, are configured to, and are made of material(s) that create a fluid lumen therein between a first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "O." Any of the conduits herein can be impermeable. Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit may extend radially within the expandable member so that inner surface of the conduit is radially within the expandable member where it is secured to the expandable member.

Any of the expandable scaffolds or member(s) herein may be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable scaffold or member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

Figures 6A, 6B, 6C, 7:
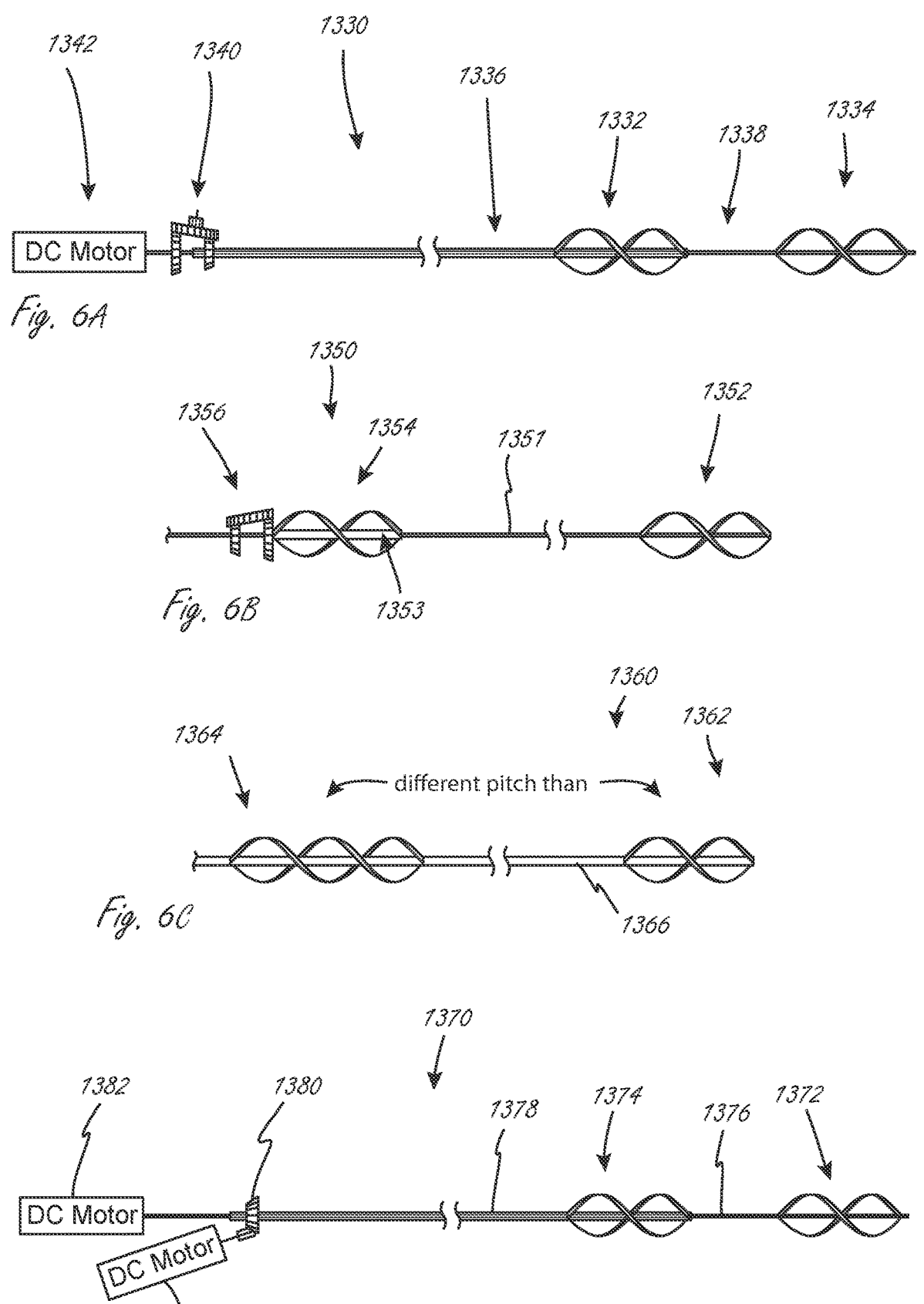
FIG. 6A illustrates at least a portion of an exemplary catheter blood pump that includes a pump portion, wherein at least two different impellers can be rotated at different speeds.
FIG. 6B illustrates at least a portion of an exemplary catheter blood pump that includes a pump portion, where at least two different impellers can be rotated at different speeds.
FIG. 6C illustrates at least a portion of an exemplary catheter blood pump that includes a pump portion with at least two impellers having different pitches.
FIG. 7 illustrates a portion of an exemplary catheter blood pump that includes a pump portion.

In any of the embodiments herein in which the catheter blood pump includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

FIG. 6B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 6A. FIGS. 6A and 6B illustrate how a gearset can be adapted to drive the proximal impeller slower or faster than the distal impeller.

FIG. 7 illustrates an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

In some embodiments, a common drive mechanism (e.g., cable and/or shaft) can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 6C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions (or distal portions) herein with a plurality of impellers can be modified to include first and second impellers with different pitches.

In any of the embodiments herein, the pump portion may have a compliant or semi-compliant (referred to generally together as "compliant") exterior structure. In various embodiments, the compliant portion is pliable. In various embodiments, the compliant portion deforms only partially under pressure. For example, the central portion of the pump may be formed of a compliant exterior structure such that it deforms in response to forces of the valve. In this manner the exterior forces of the pump on the valve leaflets are reduced. This can help prevent damage to the valve at the location where it spans the valve.

Figures 8, 9:
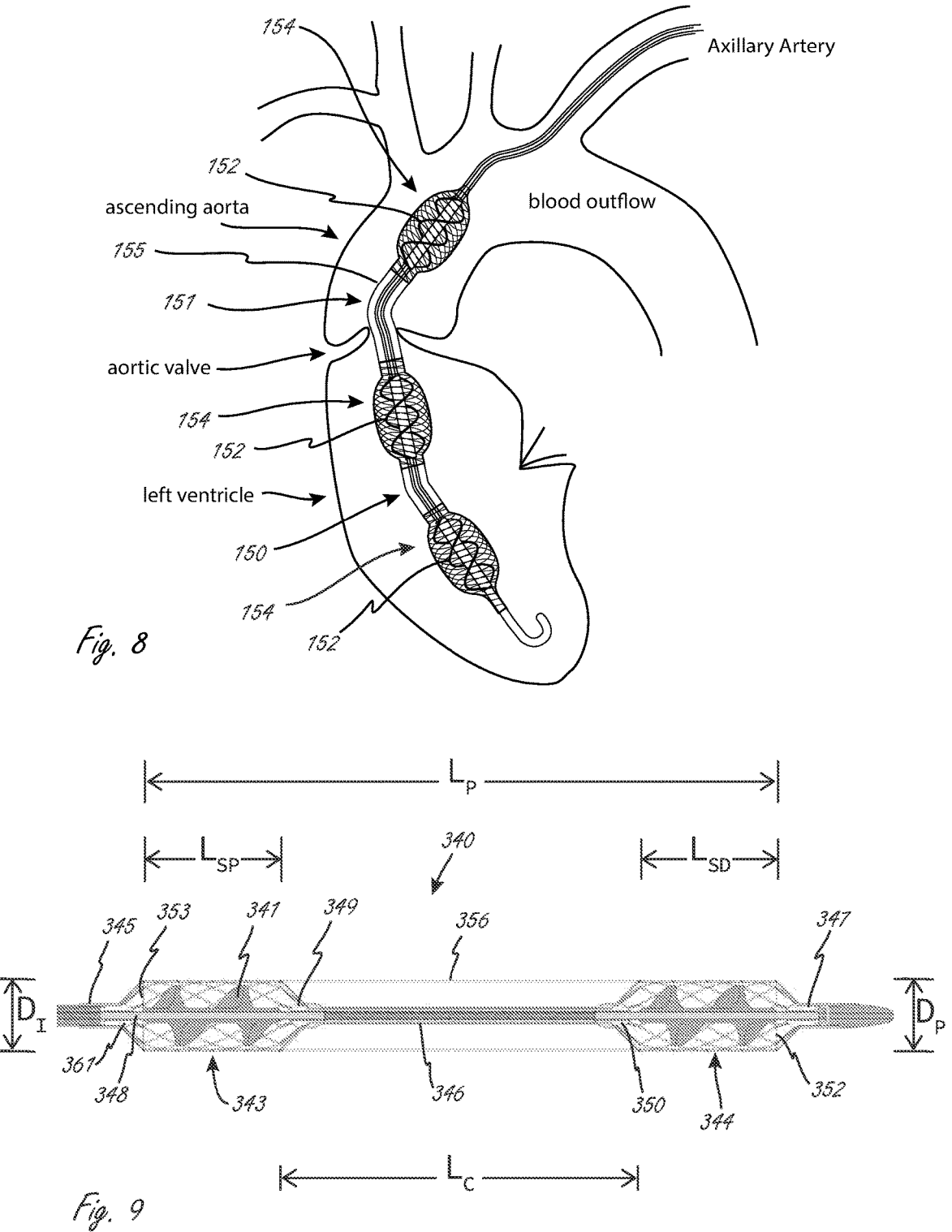
FIG. 8 illustrates an exemplary expandable pump portion including a plurality of expandable impellers, including one or more bends formed therein between adjacent impellers.
FIG. 9 illustrates an exemplary expandable pump portion comprising a plurality of impellers and a blood conduit.

FIG. 8 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1. In FIG. 8, a fluid lumen extends from a distal end to a proximal end, features of which are described elsewhere herein. The embodiment in FIG. 8 can include any other suitable feature, including methods of use, described herein.

The embodiment in FIG. 8 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 8. In this method of placement, a central impeller and distal-most impeller are positioned in the left ventricle, and a proximal-most impeller is positioned in the ascending aorta. Bend 151 is positioned just downstream to the aortic valve.

A bend such as bend 150 or 151 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 8, the pump is positioned via the axillary artery, which is an exemplary method of accessing the aortic valve, and which allows the patient to walk and be active with less interruption. Any of the devices herein can be positioned via the axillary artery. It will be appreciated from the description herein, however, that the pump may be introduced and tracked into position in various manners including a femoral approach over the aortic arch.

One aspect of the disclosure is a catheter blood pump that includes a distal impeller axially spaced from a proximal impeller. Distal and proximal impellers may be axially spaced from each other. For example, the distal and proximal impellers may be connected solely by their individual attachment to a common drive mechanism. This is different from a single impeller having multiple blade rows or sections. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse.

The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. I t can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 9 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between the impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 9), from 0.5 cm to 10 cm, or any subrange thereof. The examples below provide exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 9. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the housing can have a deployed diameter, at least the location of an impeller (and optionally at a location between impellers), shown as dimension Dp in FIG. 9. In some embodiments Dp can be from 0.3 cm to 1.5 cm, or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension Di in FIG. 9. In some embodiments Di can be from 1 mm-30 mm, or any subrange therein. For example, in some embodiments Di may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm-1 mm, such as 0.05 mm to 0.8 mm, or such as 0.1 mm-0.5 mm.

In any of the embodiments herein that includes multiple impellers, the axial spacing between impellers (along the length of the pump portion, even if there is a bend in the pump portion) can be from 2 mm to 100 mm, or any combination of upper and lower limits inclusive of 5 and 100 mm (e.g., from 10 mm-80 mm, from 15 mm-70 mm, from 20 mm-50 mm, 2 mm-45 mm, etc.).

Any of the pump portions herein that include a plurality of impellers may also include more than two impellers, such as three, four, or five impellers (for example).

Figure 10:
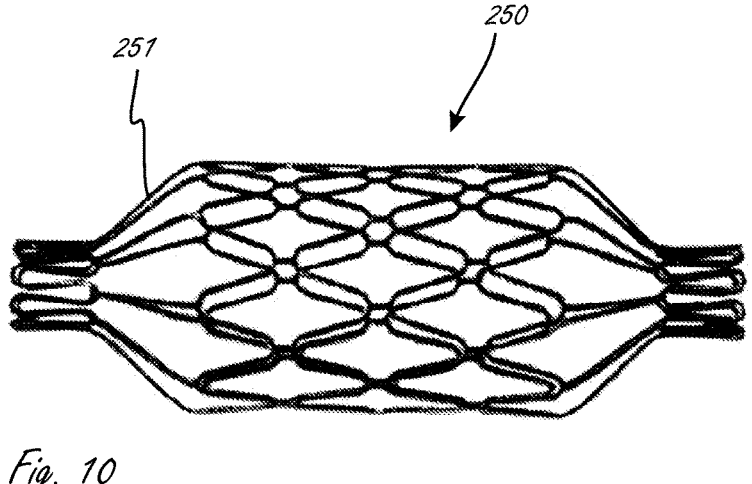
FIG. 10 illustrates an exemplary scaffold design and exemplary struts.

FIG. 10 illustrates an expandable scaffold 250 that may be one of at least two expandable scaffolds of a pump portion, such as the expandable scaffolds in FIGS. 3A-3D, wherein each expandable scaffold at least partially surrounds an impeller. The scaffold design in FIG. 10 has proximal struts 251 (only one labeled) extending axially therefrom. Having a separate expandable scaffold 250 for each impeller provides for the ability to have different geometries for any of the individual impellers. Additionally, this design reduces the amount of scaffold material (e.g., Nitinol) over the length of the expandable blood conduit, which may offer increased tracking when sheathed. A potential challenge with these designs may include creating a continuous membrane between the expandable scaffolds in the absence of an axially extending scaffolding material (see FIG. 3A). Any other aspect of the expandable scaffolds or members herein, such as those described in FIGS. 3A-3D, may be incorporated by reference into this exemplary design. Struts 251 may be disposed at a pump inflow or outflow. Struts 251 may be proximal struts or they may be distal struts.

Figure 11:
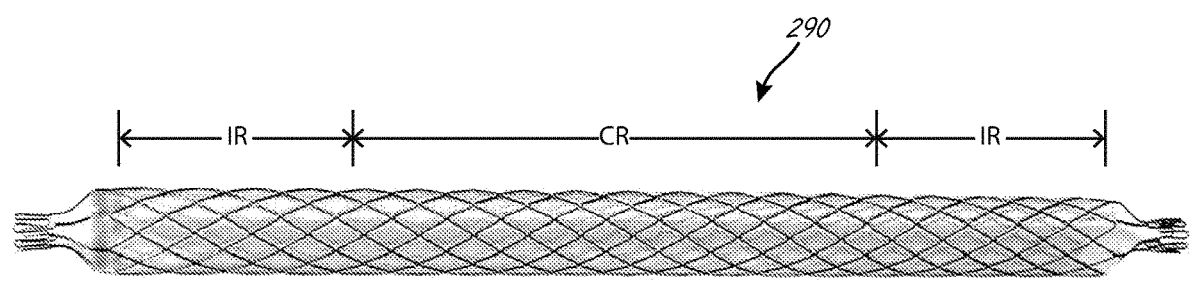
FIG. 11 illustrate an exemplary scaffold design and exemplary struts.

FIG. 11 show an exemplary scaffold along an length of the blood conduit. Central region "CR" may be axially between proximal and distal impellers. Central region "CR" flexibility is increased relative to scaffold impeller regions "IR" due to breaks or discontinuities in the scaffold pattern in the central region. The scaffold has relatively more rigid impeller sections "IR" adjacent the central region where impellers may be disposed (not shown). The relatively increased rigidity in the impeller regions IR may help maintain tip gap and impeller concentricity. This pump scaffold pattern provides for a flexibility distribution, along its length, of a proximal section of relatively less flexibility ("IR"), a central region "CR" of relatively higher flexibility, and a distal section "IR" of relatively less flexibility than the central region. The relatively less flexible sections (i.e., the two IR regions) are where proximal and distal impellers may be disposed (not shown but other embodiments are fully incorporated herein in this regard), with a relatively more flexible region in between. Exemplary benefits of the relative flexibility in these respective sections are described elsewhere herein. FIG. 11 is an example of a scaffold that is continuous from a first end region to a second end region, even though there are breaks or discontinuities in some locations of the scaffold. There is at least one line that can be traced along a continuous structural path from a first end region to a second end region.

The following disclosure provides exemplary method steps that may be performed when using any of the blood pumps, or portions thereof, described herein. It is understood that not all of the steps need to be performed, but rather the steps are intended to be an illustrative procedure. It is also intended that, if suitable, in some instances the order of one or more steps may be different. Before use, the blood pump can be prepared for use by priming the lumens (including any annular spaces) and pump assembly with sterile solution (e.g., heparinized saline) to remove any air bubbles from any fluid lines. The catheter, including any number of purge lines, may then be connected to a console. Alternatively, the catheter may be connected to a console and/or a separate pump that are used to prime the catheter to remove air bubbles.

Figure 12A:
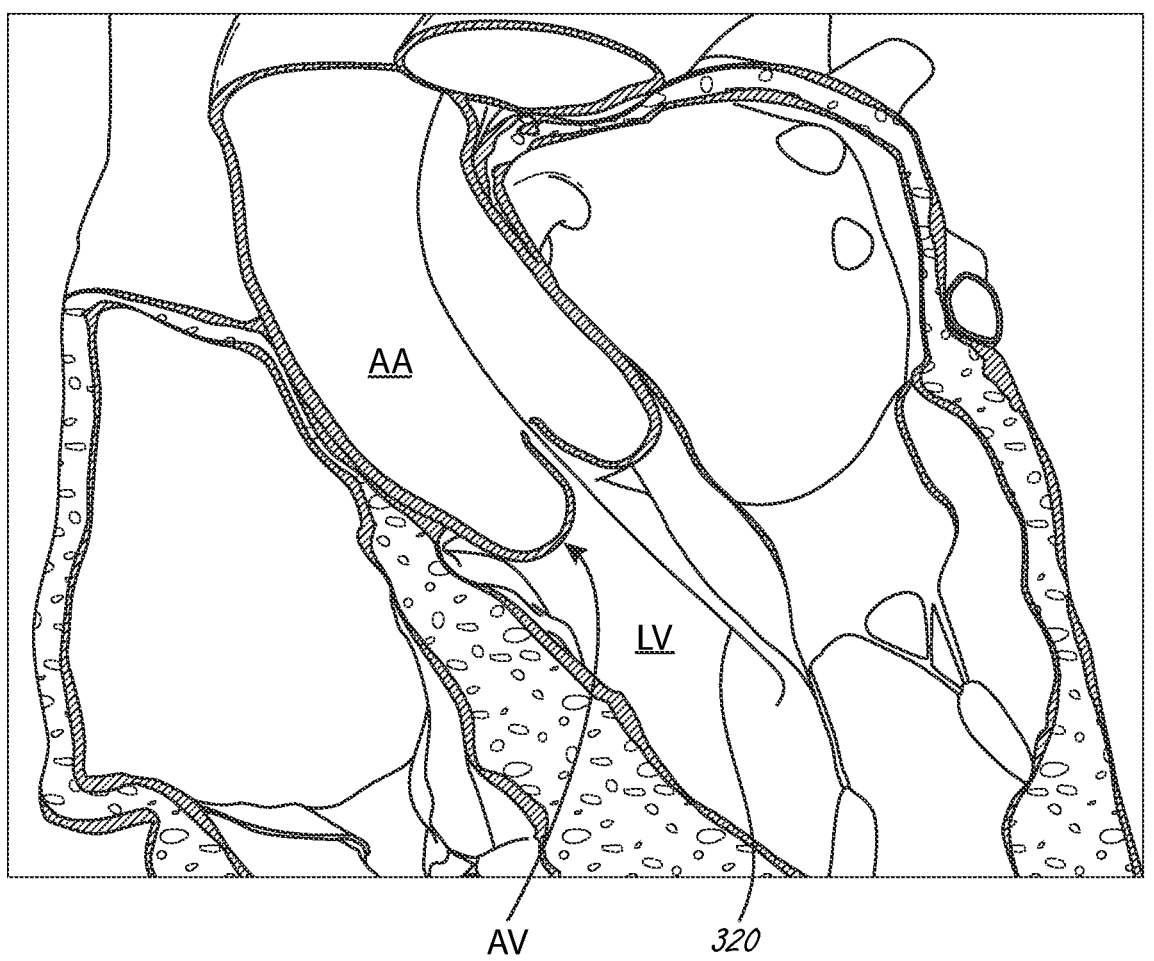
FIGS. 12A-12F illustrate an exemplary sequence of steps that may be performed to deploy an exemplary pump portion of a catheter blood pump.
Figure 12B:
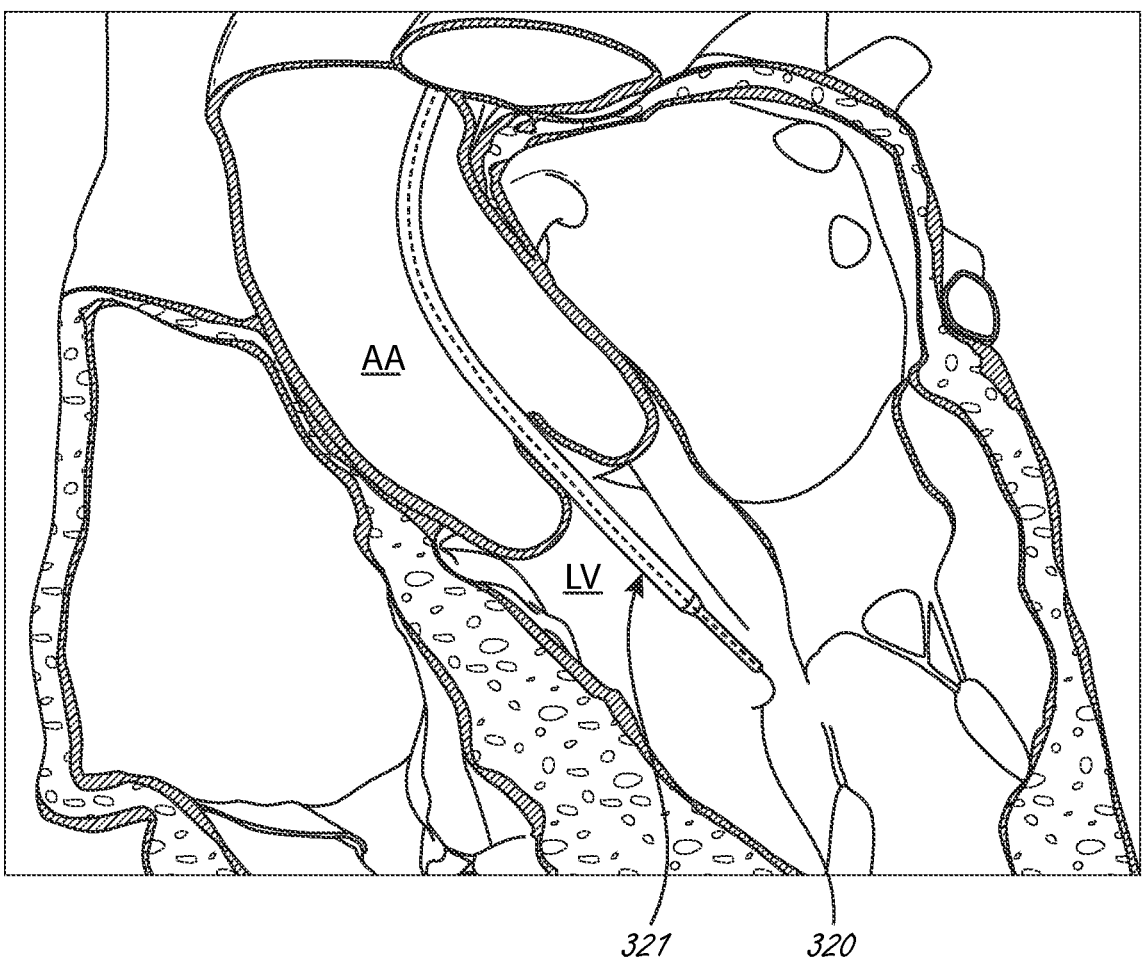

After priming the catheter, access to the patient's vasculature can be obtained (e.g., without limitation, via femoral access) using an appropriately sized introducer sheath. Using standard valve crossing techniques, a diagnostic pigtail catheter may then be advanced over a, for example, 0.035" guide wire until the pigtail catheter is positioned securely in the target location (e.g., left ventricle). The guidewire can then be removed and a second wire 320 (e.g., a 0.018" wire) can be inserted through the pigtail catheter. The pigtail catheter can then be removed (see FIG. 12A), and the blood pump 321 (including a catheter, catheter sheath, and pump portion within the sheath; see FIG. 12B) can be advanced over the second wire towards a target location, such as spanning an aortic valve "AV," and into a target location (e.g., left ventricle "LV"), using, for example, one or more radiopaque markers to position the blood pump.

Figure 12C:
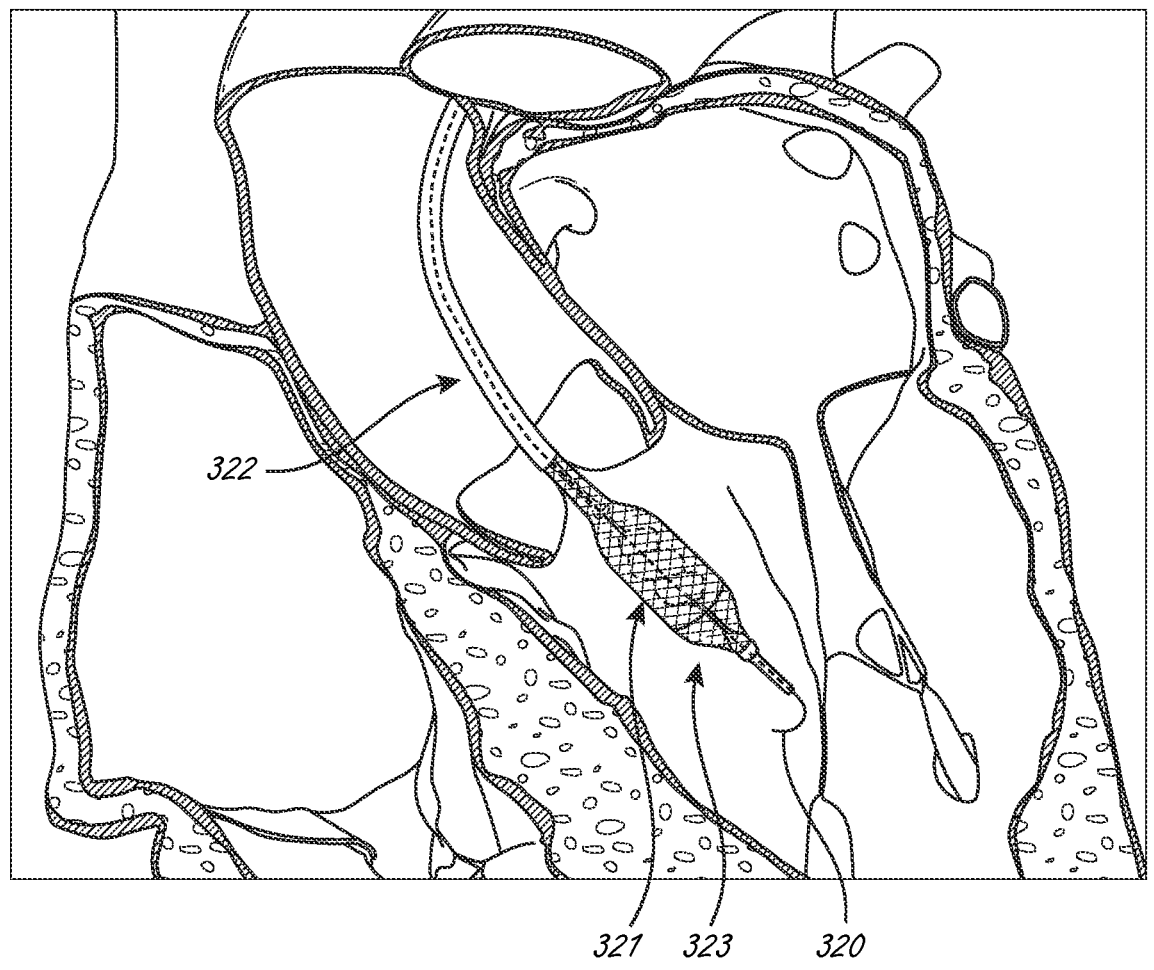
Figure 12D:
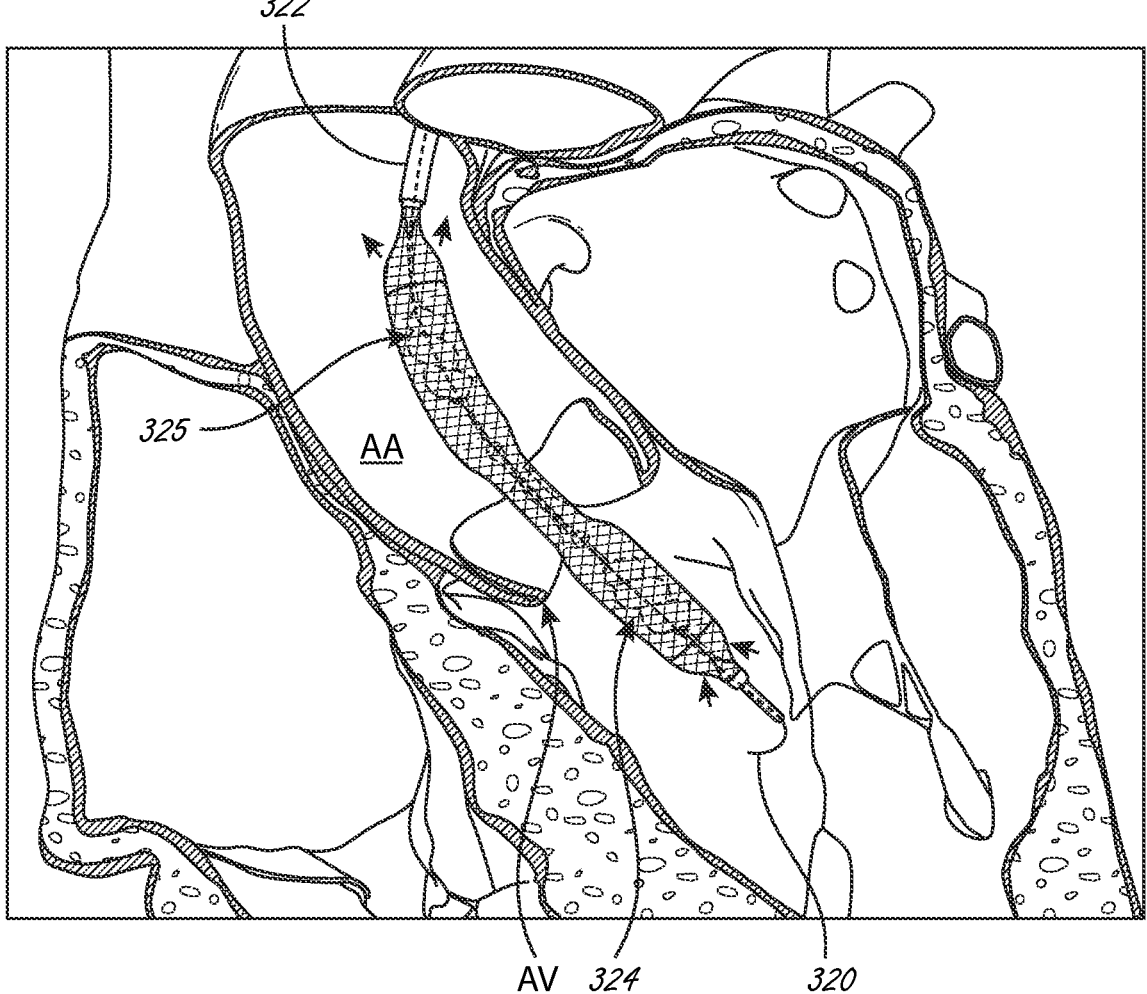

Once proper placement is confirmed, the catheter sheath 322 (see FIG. 12C) can be retracted, exposing first a distal region of the pump portion. In FIG. 12C a distal region of an expandable housing has been released from sheath 322 and is expanded, as is distal impeller 324. A proximal end of housing 323 and a proximal impeller are not yet released from sheath 322. Continued retraction of sheath 322 beyond the proximal end of housing 323 allows the housing 323 and proximal impeller 325 to expand (see FIG. 12D). The inflow region (shown with arrows even though the impellers are not yet rotating) and the distal impeller are in the left ventricle. The outflow (shown with arrows even though the impellers are not rotating yet) and proximal impeller are in the ascending aorta AA. The region of the outer housing in between the two impellers, which may be more flexible than the housing regions surrounding the impellers, as described in more detail herein, spans the aortic valve AV. In an exemplary operating position as shown, an inlet portion of the pump portion will be distal to the aortic valve, in the left ventricle, and an outlet of the pump portion will be proximal to the aortic valve, in the ascending aorta "AA").

Figure 12E:
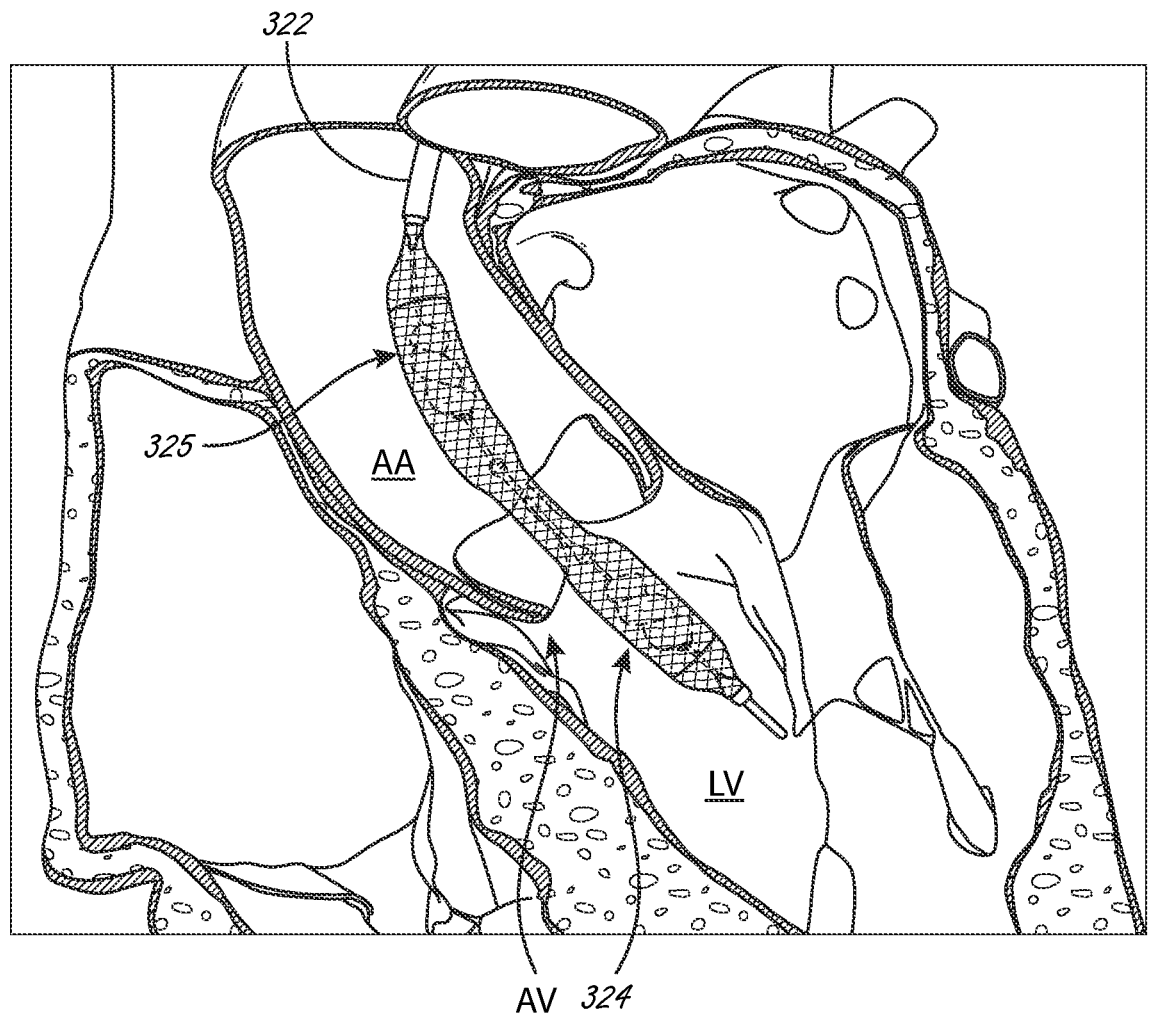
Figure 12F:
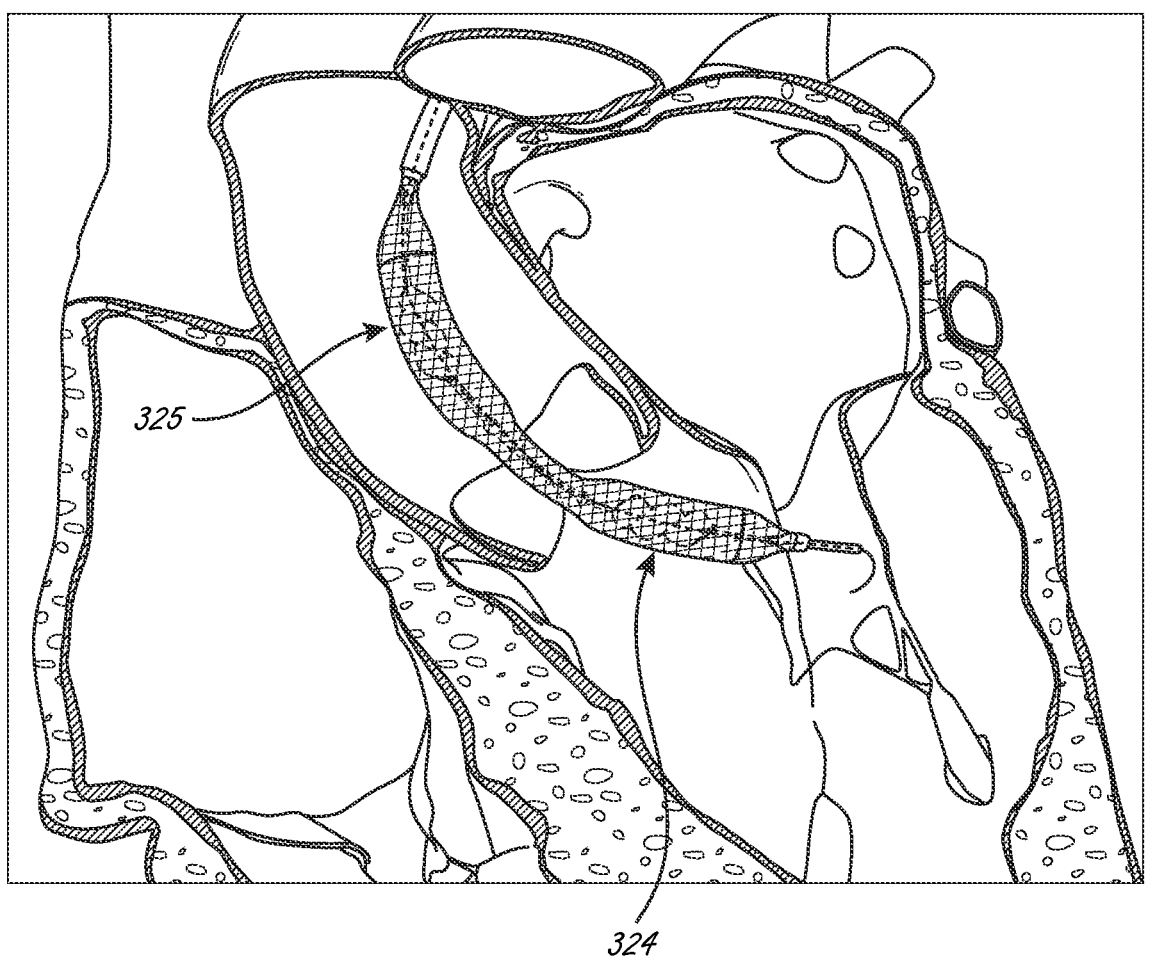

The second wire (e.g., an 0.018" guidewire) may then be moved prior to operation of the pump assembly (see FIG. 12E). If desired or needed, the pump portion can be deflected (active or passively) at one or more locations as described herein, as illustrated in FIG. 12F. For example, a region between two impellers can be deflected by tensioning a tensioning member that extends to a location between two impellers. The deflection may be desired or needed to accommodate the specific anatomy. As needed, the pump portion can be repositioned to achieve the intended placement, such as, for example, having a first impeller on one side of a heart valve and a second impeller on a second side of the heart valve. It is understood that in FIG. 12F, the pump portion is not in any way interfering or interacting with the mitral valve, even if it may appear that way from the figure.

As set forth above, this disclosure includes catheter blood pumps that include an expandable pump portion extending distally relative to a catheter. The pump portions include an impeller housing that includes an expandable blood conduit that defines a blood lumen. The blood conduit may include one or more scaffold sections that together may also be referred to herein as a single scaffold. In some exemplary embodiments the expandable blood conduit may include one or more of a proximal impeller scaffold, a distal impeller scaffold, and a central scaffold disposed between the proximal impeller scaffold and the distal impeller scaffold, where any combination thereof may also be referred to herein as a scaffold. Any individual proximal impeller scaffold or distal impeller scaffold may also be referred to herein as an expandable member, such as is shown in FIGS. 3A-3D. In some embodiments the expandable blood conduit may include a proximal impeller scaffold and additional scaffold extending distally therefrom, such as if the pump portion includes a proximal impeller but does not include a distal impeller. In any of the embodiments herein, a reference to a distal impeller is only by way of example, and pump portions herein need not include a distal impeller. Central scaffolds herein are generally less stiff in response to a radially inward force than a proximal scaffold, and optionally also less stiff than a distal scaffold, such as a distal impeller scaffold. Exemplary advantages of central scaffold sections that are less stiffness are set forth elsewhere herein. The blood conduit may also include a membrane coupled to the one or more scaffolds, the membrane at least partially defining the blood lumen. Membranes in this context may incorporate by reference herein the disclosure of conduits, including any feature or method of manufacturing described above. The catheter blood pumps may include an impeller disposed in a proximal region of the impeller housing, which may be a proximal impeller. The catheter blood pumps may also include a distal impeller in a distal region of the impeller housing. Exemplary impellers, including exemplary proximal and distal impellers, are set forth herein by way of example. An impeller that is at least partially within a portion of a scaffold may be described with respect to the relative position of the scaffold, such the a proximal impeller within at least a portion of a proximal scaffold, or a distal impeller within at least a portion of a distal scaffold.

When a proximal impeller is described as being within a proximal scaffold, it is understood that the proximal scaffold need not axially extend over an entire length of the impeller, as long as there is some amount of axial overlap. For example, some proximal impellers herein extend proximally from a blood conduit, and a proximal region of the proximal impeller is not surrounded by a blood conduit scaffold, while a distal region of the impeller is surrounded by scaffold. Similarly, when a distal impeller herein (if the pump includes a distal impeller) is described as being within a distal scaffold, it is understood that the distal scaffold need not axially extend over an entire length of the impeller, as long as there is some degree of axial overlap therebetween.

FIGS. 13A-17 illustrate exemplary designs for expandable scaffolds herein, which may at least partially surround an impeller that is at least partially disposed within a conduit that creates a fluid lumen. The scaffold patterns in FIGS. 13A-17 may be scaffold patterns that only extend over a particular impeller (e.g., a proximal basket or distal basket), or they may be scaffold patterns that extend over an entire blood conduit scaffold.

FIGS. 13A-17 illustrate expandable support members or scaffolds that each have an expanded configuration, wherein in the expanded configuration the support member has a plurality of continuous axially extending elements (e.g., 408, 410, 420, 430, 440) that are continuous and axially extending over at least 50% of a length of the expandable support member (e.g., L$_s$), and wherein the expandable support member includes a plurality of sets of connectors (e.g., 412/414, 409, 422/424, 432/434, 442/444) each set of connectors extending between first and second circumferentially adjacent continuous axially extending elements. In some embodiment the axially extending elements are linear or substantially linear.

Figures 13A, 13B, 13C:
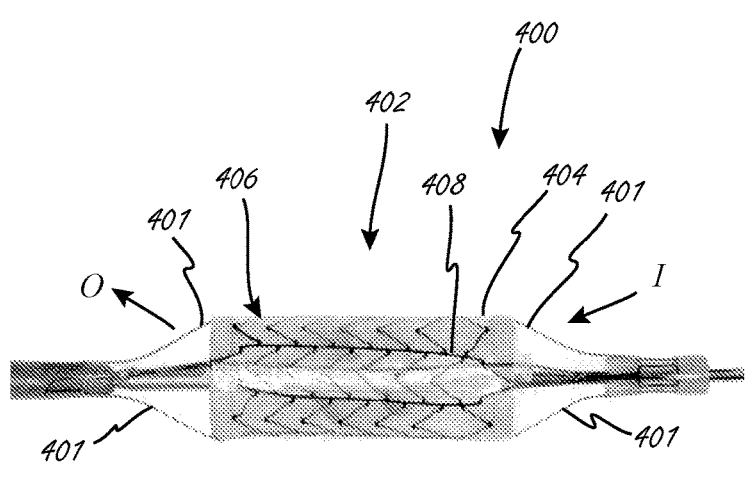
FIGS. 13A and 13B illustrate exemplary portions of an expandable pump portion.
FIG. 13C illustrates a scaffold from FIGS. 13A and 13B shown in a flattened and non-expanded configuration, as well as optional distal and proximal struts extending axially therefrom.

FIGS. 13A-13C illustrate an exemplary pump portion 400 or a portion thereof that comprises an expandable impeller housing 402, wherein the expandable impeller housing having a blood conduit 404, the conduit defining a blood lumen between an housing inflow "I" and a housing outflow "O". The expandable impeller housing also includes an expandable scaffold or support member 406 at least partially surrounding an impeller (not shown in FIGS. 13A-13C) that is at least partially disposed within the conduit. FIGS. 14A-17 illustrate an expandable scaffold of the pump portion. It is understood that any expandable scaffold in any of FIGS. 13A-17 may be used in place of any expandable scaffold herein. Impeller housing 402 may illustrate the entire impeller housing, or it may only represent only a portion thereof, including only a single scaffold section, such as with any of the multi-impeller designs herein. It is thus understood that the structure shown in FIGS. 13A-C may only be a portion of the expandable housing of a pump portion. For example, a pump portion may include two of the expandable scaffold sections shown in FIGS. 13A-C, axially spaced apart, and coupled by a flexible membrane, for example.

FIGS. 13A-C illustrate an expandable impeller housing that includes a plurality of axially extending elements 408 circumferentially spaced apart around the housing 402 from adjacent axially extending elements, as shown. FIGS. 13A and 13B show an expanded configuration of the housing, while FIG. 13C illustrates a model of a flat, unexpanded configuration with unitary struts 401 extending axially therefrom, as shown. The plurality of axially extending elements may be referred to as "elements" in the context of scaffolds for simplicity, but it is understood that they are not to be considered any other type of "element" herein unless specifically indicated as such. The elements in this embodiment may be axial and linear in the housing expanded configuration. Expandable scaffold 406 also includes circumferential connectors 409 that circumferentially connect adjacent axial elements and extend from one axial element to an adjacent axial element. In this exemplary embodiment all of the connectors have the same general configuration, which includes first and second segments meeting at a rounded peak that is oriented axially (proximally or distally depending on the reference frame), otherwise stated as pointing axially. Length Ls of the scaffold and length Le of the elements is illustrated in FIG. 13C. Optional struts 401 are shown (which may be unitary with the scaffold). The axial elements 408 in this embodiment extend from a first axial element end 405 to second axial element end 405', which extend almost the entire length of the scaffold Ls. As shown, ends 405' of the elements (only one labeled) extend to a distal end region 407' of the scaffold 406. End 405 extends to proximal end region 407. The pump portion also includes a transition region 411, which includes circumferential extensions of adjacent axial elements, after which they meet to form a strut 401, as shown.

Figure 14A:
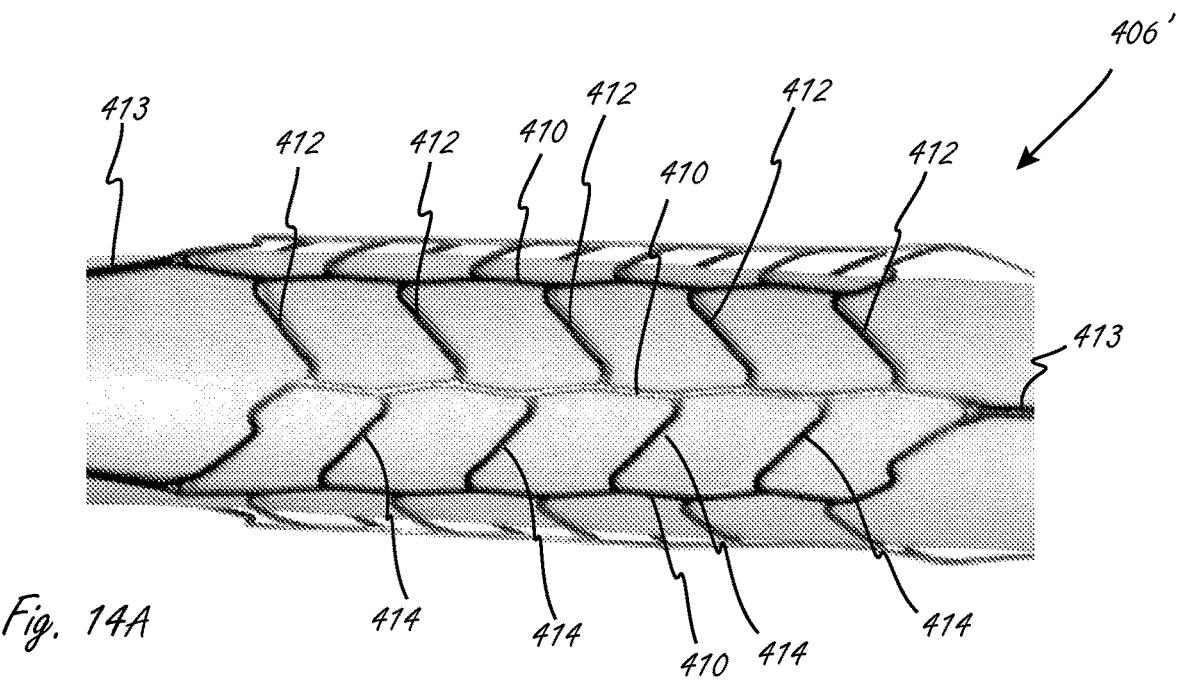
FIG. 14A illustrates an exemplary expanded scaffold that may be part of any of the expandable pump portions herein.
Figure 14B:
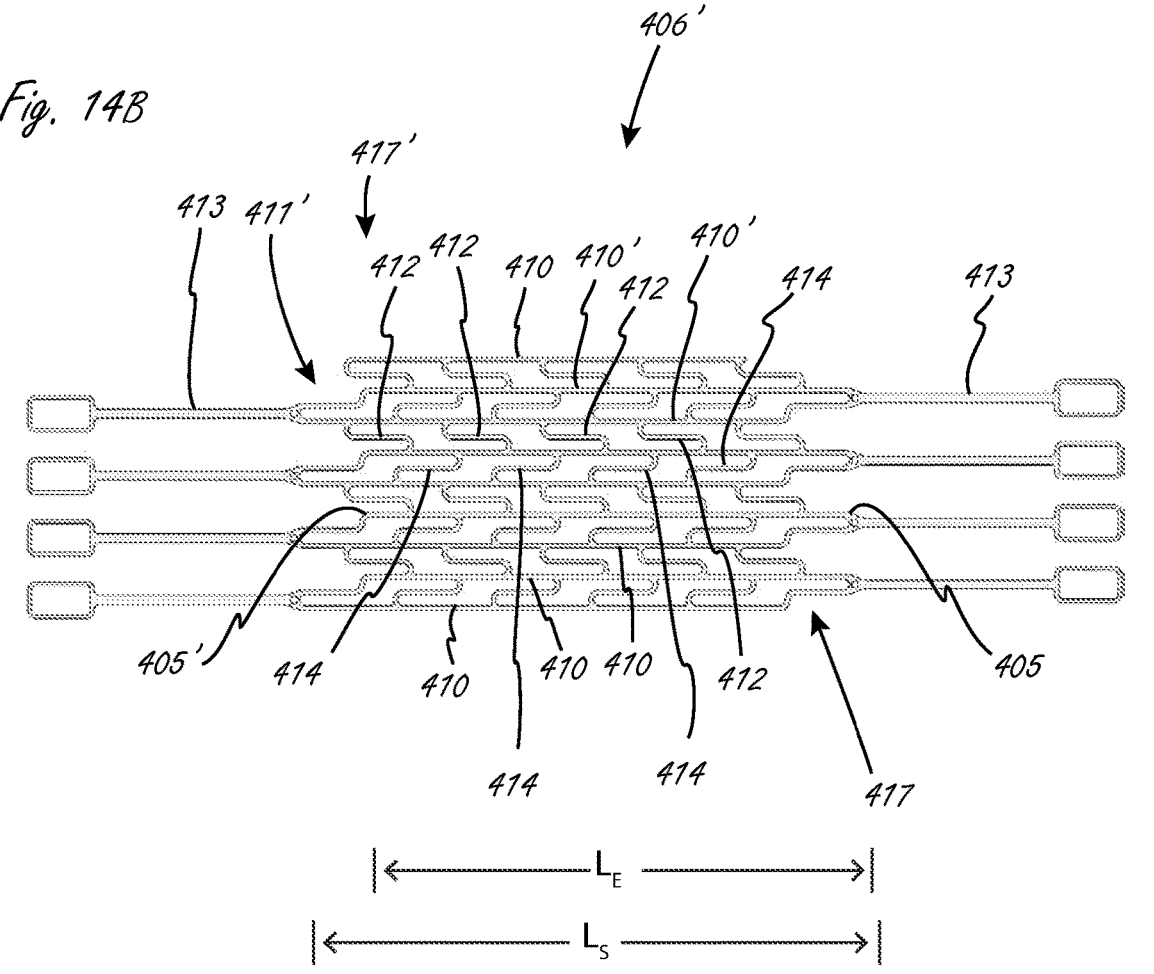
FIG. 14B illustrates the scaffold and struts from FIG. 14A in a flattened and non-expanded configuration.

FIGS. 14A (expanded) and 14B (unexpanded) illustrate an exemplary expandable scaffold 406', which includes a plurality of axially extending elements 410. A first set of connectors 412 have "S" configurations, and a second circumferentially adjacent set of connectors 414 have inverse (reverse) "S" shapes. In the expanded configuration in FIG. 14A the axial elements 410 may be linear, or they may have a slight curvilinear configuration as shown. Scaffold 406' includes transition region 411', which may have similar features to the transition region 411 herein. The relevant description from any other embodiment may be incorporated with the scaffold in FIGS. 14A-B (e.g., lengths of scaffold or support member and axial elements, transition region, etc.). Some of the optional struts 413 are shown, as are ends 405/405' of the axial elements. Scaffold 406' may be proximal or distal scaffold, or it may extend along the length of the impeller housing.

FIGS. 15A and 15B illustrate an exemplary expandable scaffold 406" that is similar to those in FIGS. 13, 14, 16, and 17. Axially extending elements 420 are shown, adjacent ones of which are connected by circumferential connectors 422 and 424, ends of which are axially offset. A first set of connectors 422 has a general S configuration, while a second set of connectors 424 are reverse S-shaped. In this embodiments the axially extending elements 420 are curvilinear, as shown. The pattern of S and inverse-S alternates around the expandable member, as it does in the scaffolds in FIGS. 14A and 14B. Scaffold 406" also includes a transition region 421, examples of which are described elsewhere herein. Scaffold 406" may be proximal or distal scaffold, or it may extend along the length of the impeller housing.

Figure 16:
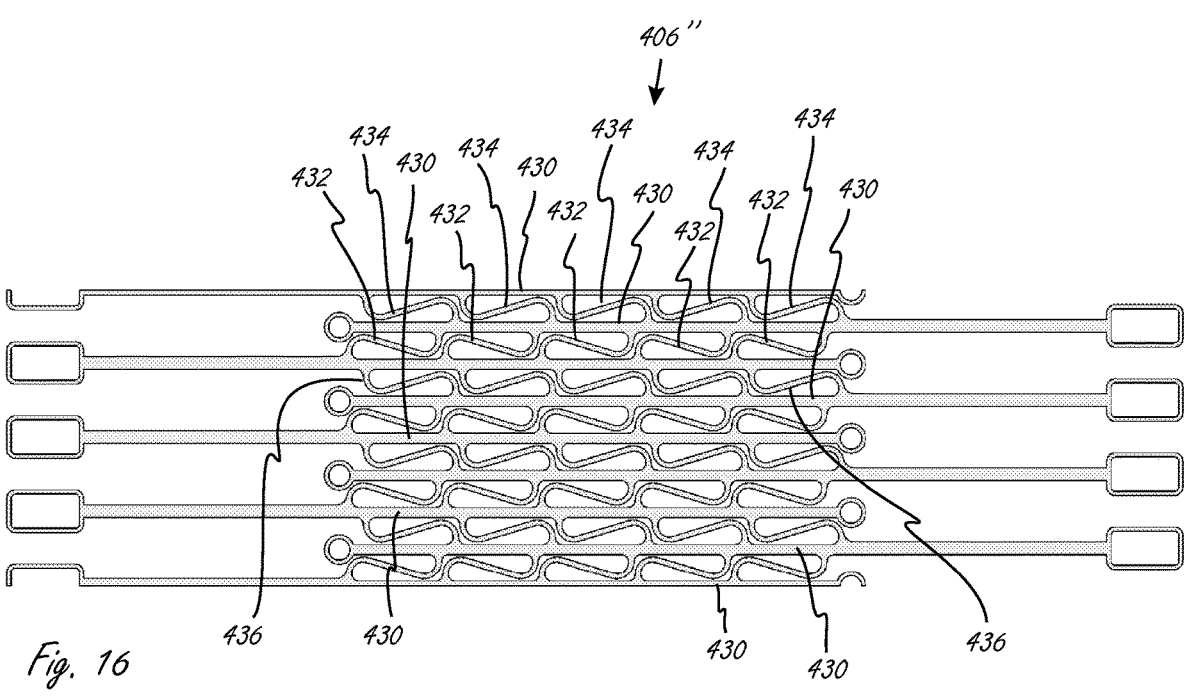
FIG. 16 illustrates an exemplary scaffold and optionally coupled struts in a flattened and non-expanded configuration.

FIG. 16 illustrates a collapsed (unexpanded) configuration of an exemplary scaffold 406''', which may have any other suitable features of any other support member or scaffold herein. Axially extending elements 430 are shown, connected by first set of S-shaped connectors 434 and a second set of inverse-S shaped connectors 432. The pattern of S and inverse-S shapes alternates circumferentially around the scaffold 406''' as shown. Scaffold 406''' may be proximal or distal scaffold, or it may extend along the length of the impeller housing.

Figure 17:
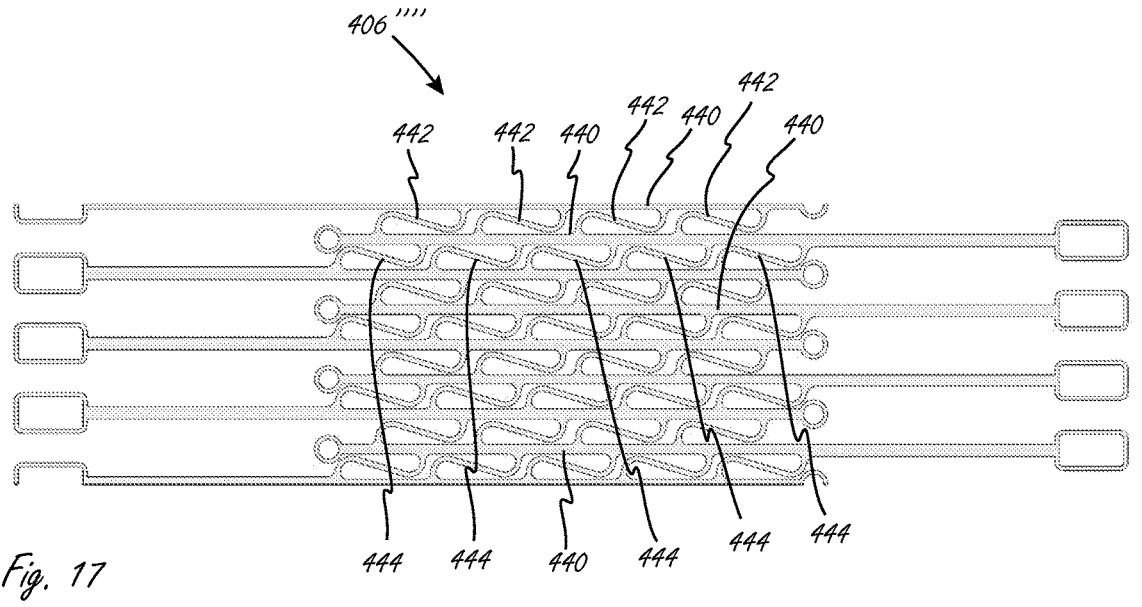
FIG. 17 illustrates an exemplary scaffold and optionally coupled struts in a flattened and non-expanded configuration.

FIG. 17 illustrates a collapsed (unexpanded) configuration of an exemplary scaffold 406"", which may have any other suitable features of any other support member or scaffold herein. Axially extending elements 440 are shown, connected by inverse-S shaped connectors. All sets of the connectors in this embodiment (e.g., set 442 and set 444) have the same configuration, and in this embodiment are all inverse-S shaped. Exemplary struts are shown axially disposed relative to the scaffold 406"", and the scaffold 406"" may include transition sections which are described elsewhere herein. Scaffold 406"" may be a proximal scaffold or a distal scaffold, or it may extend along the length of the impeller housing.

The scaffolds and blood conduit embodiments in FIGS. 13A-17 are illustrative, and may be modified to include aspects of other embodiments herein. The following description may provide modifications to the scaffolds in FIGS. 13A-17, any of which may be incorporated into any of the scaffolds in FIGS. 13A-17.

In any of the scaffolds shown in FIGS. 13A-17, at least a first end of each of the plurality of axially extending elements may extend to one or more of a proximal end region (e.g., 417', 407') and a distal end region (e.g., 417) of the expandable scaffold.

In any of the scaffolds shown in FIGS. 13A-17, at least one of, and optionally all of, the plurality of axially extending elements may be linear. In any of the scaffolds shown in FIGS. 13A-17, at least one of, and optionally all of, the plurality of axially extending elements may be curvilinear.

In any of the scaffolds shown in FIGS. 13A-17, each one of the plurality of axially extending elements may have proximal and distal ends, wherein the proximal and distal ends are substantially circumferentially aligned.

In any of the scaffolds shown in FIGS. 13A-17, each of the plurality of axially extending elements may have a circumferential span (illustrated as "CS" in FIG. 15A) that is not larger than 10 degrees circumferentially around the expandable scaffold, optionally not larger than 5 degrees of the expandable scaffold.

In any of the scaffolds shown in FIGS. 13A-17, each of the plurality of axially extending elements may follow a path that is substantially parallel with a longitudinal axis of the expandable scaffold.

In any of the embodiments in FIGS. 13A-17, each of the plurality of axially extending elements may be continuous and axially extending over at least 55% of a length of the expandable scaffold, optionally over at least 60%, optionally over at least 65%, optionally over at least 70%, optionally over at least 75%, optionally over at least 80%, optionally over at least 85%, optionally over at least 90, optionally over at least 95.

In any of the scaffolds shown in FIGS. 13A-17, all of the connectors in all of the sets of the plurality of sets of connectors may have the same configuration. In any of the scaffolds shown in FIGS. 13A-17, all of the connectors in all of the sets of the plurality of sets of connectors may not have the same configuration. In any of the scaffolds shown in FIGS. 13A-17, each individual set of connectors may have a plurality of connectors that have the same configuration. In any of the embodiments in FIGS. 13A-17, all of the connectors in all of the sets of the plurality of sets of connectors may have an S-shape. In any of the embodiments in FIGS. 13A-17, all of the connectors in all of the sets of the plurality of sets of connectors may have a reverse (or inverted) S-shape. In any of the scaffolds shown in FIGS. 13A-17, all of the connectors in a first set of connectors may have a S shape. In any of the scaffolds shown in FIGS. 13A-17, a second set of connectors that is circumferentially adjacent to the first set of connectors may all have an inverted S shape. In any of the scaffolds shown in FIGS. 13A-17, S shape/inverted S shape connectors may alternate around the circumference of the expandable scaffold.

In any of the embodiments in FIGS. 13A-17, a first set of connectors that extend in a first circumferential direction from a first axially extending element may extend from the first axially extending element at axial locations that are different from the axial locations at which a second set of connectors extend from the first axially extending element in a second circumferential direction (i.e., the connectors have ends that are axially offset).

In any of the embodiments in FIGS. 13A-17, the expandable scaffold may include a transition region connecting a first axially extending element with a strut, optionally wherein the transition region is considered part of the expandable scaffold. A transition region may also connect the strut with a second axially extending element, the second axially being circumferentially adjacent to the first axially extending around the blood conduit. In any of the scaffolds shown in FIGS. 13A-17, the expandable scaffold may extend along substantially the entire length of the conduit. In any of the scaffolds shown in FIGS. 13A-17, the expandable scaffold may extend along less than 50% of the length of the expandable impeller housing. In any of the embodiments in FIGS. 13A-17, the expandable scaffold may extend only in a region of the expandable housing in which an impeller is disposed.

In any of the embodiments in FIGS. 13A-17, the expandable impeller housing may include a second expandable scaffold axially spaced from the first expandable scaffold. A second expandable scaffold may have an expanded configuration with a second plurality of axially extending elements that are axially extending over at least 50% of a length of the second expandable scaffold and wherein the second expandable scaffold may also include a plurality of sets of connectors, each set of connectors extending circumferentially between first and second circumferentially adjacent axially extending elements. A second expandable scaffold may include any features set forth in any of the claims or described elsewhere herein. In any of the scaffolds shown in FIGS. 13A-17, the expandable scaffold may be unitary, that is, made from a single piece of starting material.

Figures 18A, 18B:
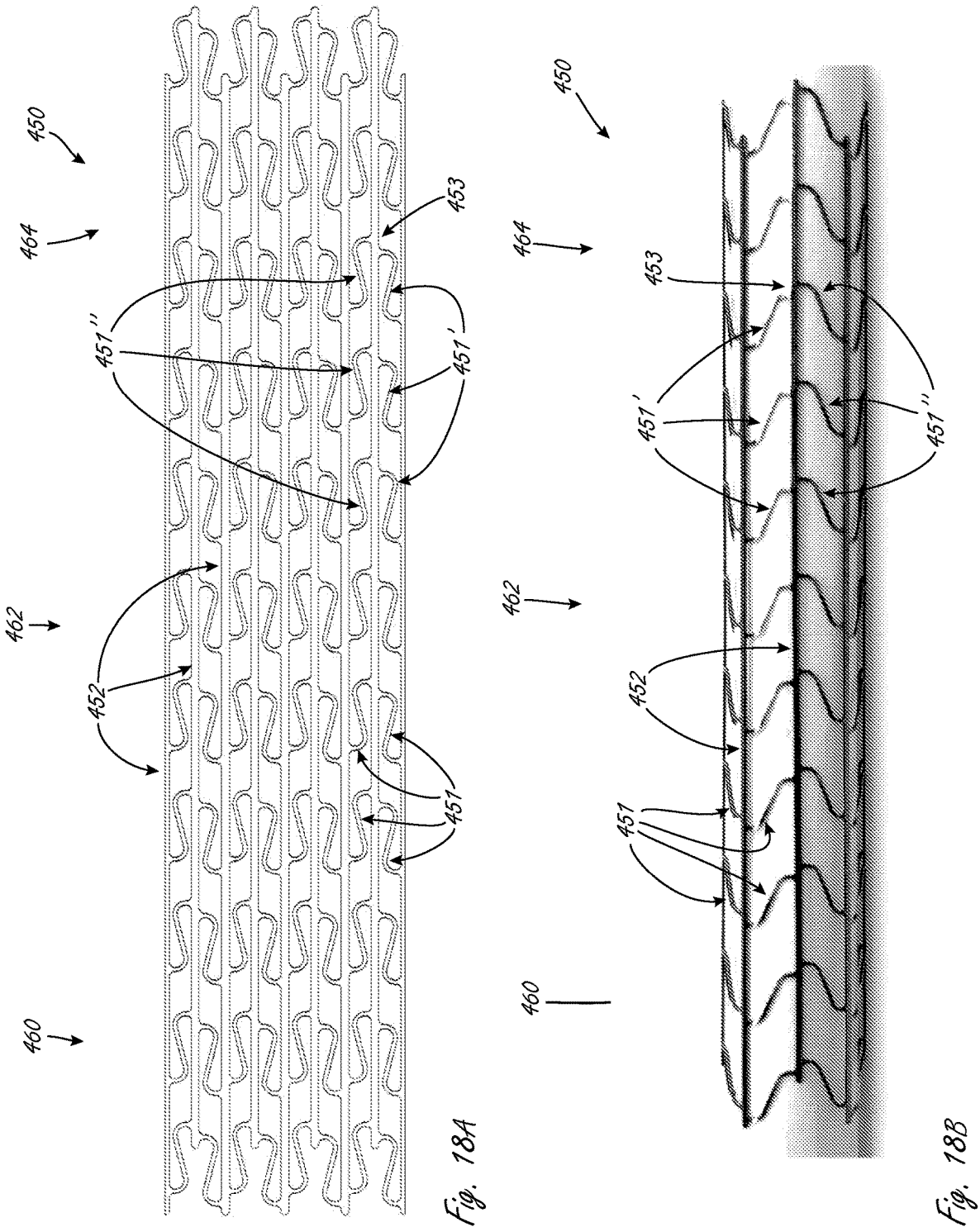
FIG. 18A illustrates an exemplary scaffold in a flattened and non-expanded configuration.
FIG. 18B illustrates the scaffold from FIG. 18A in an expanded configuration.

FIGS. 18A and 18B illustrate an exemplary scaffold 450 comprising a plurality of axially extending elements 452 (eight in this example). Scaffold 450 includes a proximal scaffold 460, a central scaffold 462, and distal scaffold 464. In this example axially extending elements 452 are linear. Central scaffold 462 is connected to proximal scaffold 460 and to distal scaffold 464 in this example, and in particular, is unitary with them in this example. FIG. 18B illustrates an expanded configuration, and FIG. 18A illustrates an as-cut flat illustration of the scaffold. The axially extending elements 452 that are labeled in FIG. 18B are circumferentially adjacent axial elements. Adjacent axially extending elements are connected by a plurality of circumferential connectors 451, which in this example have general S or inverse-S configurations, which include at least one bend formed therein. As shown, each circumferential connector is circumferentially adjacent to another circumferential connectors, and together they extend around the blood conduit. In this example, as shown, circumferentially adjacent circumferential connectors are displaced axially relative to one another. For example, circumferential connectors 451' are axially displaced (or axially offset) relative to circumferential connectors 451". Axially displaced or axially offset in this context refers to proximal ends of the connectors being axially offset, distal ends of the connectors being axially offset, or both. In this example, a section of each one of the axially extending elements connects adjacent circumferential connectors that are axially displaced. For example, section 453 of one of the axially extending elements 452 connects circumferential connector 451' and 451", which creates the axially displaced nature of the circumferentially adjacent circumferential connectors. In this example, distal ends of connectors 451" are further distally than the distal ends of the circumferentially adjacent connectors 451', as shown. FIGS. 18A and 18B also illustrate a first group of a plurality of circumferential connectors having a first axial position, and a second group of the plurality of circumferential connectors having a second axial position, wherein the first and second axial positions alternate circumferentially around the blood conduit, as shown.

Figures 19A, 19B:
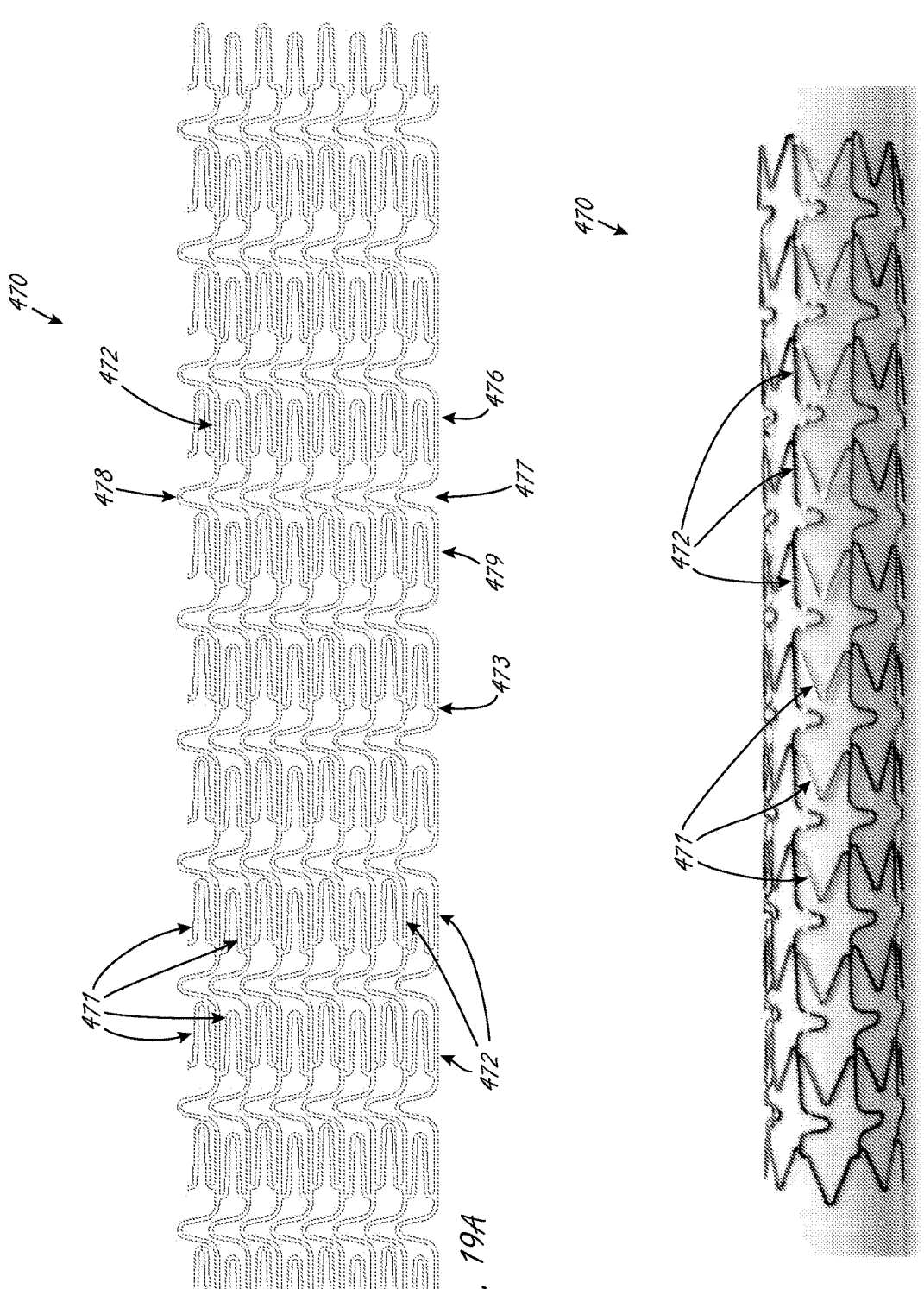
FIG. 19A illustrates an exemplary scaffold in a flattened and non-expanded configuration.
FIG. 19B illustrates the scaffold from FIG. 19A in an expanded configuration.

FIGS. 19A and 19B illustrate an exemplary scaffold 470. Scaffold 470 includes a plurality of axially extending elements 472, which are linear is sections but are not linear along the entire scaffold 470 length. Scaffold 470 also includes connectors 471 that circumferentially connect circumferentially adjacent axial elements 472. Connectors 471 includes peaks that are oriented, or point, axially, and in this example may be oriented distally or proximally Scaffold 470 includes a proximal scaffold, a central scaffold, and a distal scaffold that are connected, and in this example are unitary, just as with the scaffold in FIGS. 18A and 18B. Both the proximal scaffold, central scaffold, and distal scaffold comprise a plurality of linear axially extending elements spaced apart around the blood conduit, wherein first and second adjacent linear axially extending elements are each connected by a circumferential connector having at least one bend formed therein. The circumferential connectors defining a plurality of circumferential connectors around the blood conduit, and wherein circumferentially adjacent circumferential connectors of the plurality of circumferential connectors are displaced axially relative to one another. Like in FIGS. 18A and 19B, a section 473 of each one of the axially extending elements (in this example linear) connects circumferentially adjacent circumferential connectors that are axially displaced, as shown. FIGS. 19A and 19B illustrate a first group of a plurality of circumferential connectors having a first axial position, and wherein a second group of the plurality of circumferential connectors have a second axial position, wherein the first and second axial positions alternate circumferentially around the blood conduit. In this embodiment, the proximal, central, and distal scaffolds are generally have the same configuration (except the ends of the distal and proximal scaffolds).

Scaffold 470 also includes second region 477 that is axially adjacent first region 476, wherein second region 477 comprises a plurality of peaks 478 that are shown oriented orthogonally relative to a long axis of the blood conduit (membrane not shown for clarity). In this example, each of the plurality of peaks 478 is an extension of one of the axially extending elements 472 in the first region 476, as shown. Scaffold 470 also includes third region 479 that is axially adjacent second region 477, the third region 470 comprising a second plurality of linear axially extending elements as shown that are spaced apart around the blood conduit, and a second plurality of circumferential connectors 471, where the second region 477 joins the first region 476 and third region 479. In this example this pattern continues along the length of the scaffold.

Figures 20A, 20B:
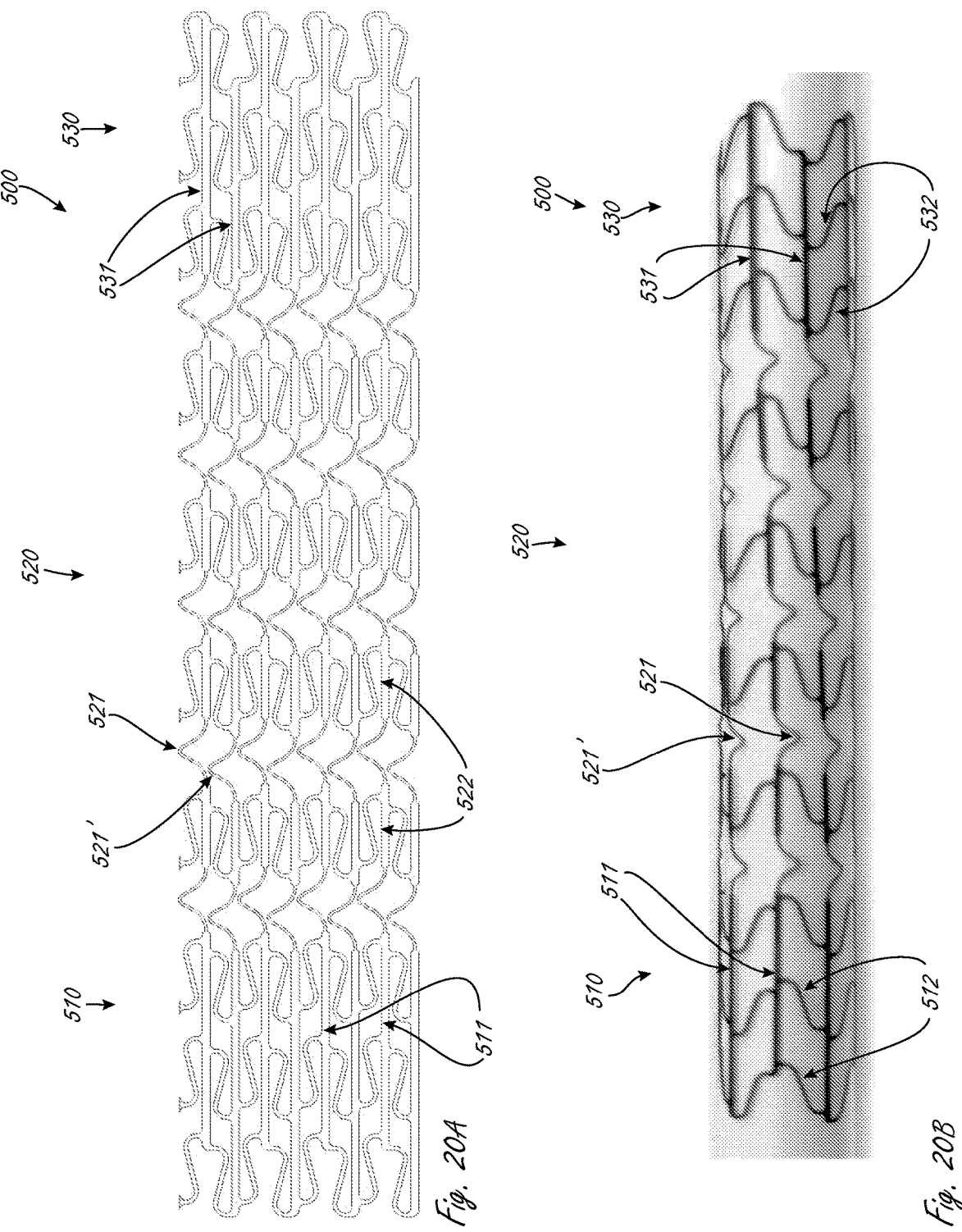
FIG. 20A illustrates an exemplary scaffold in a flattened and non-expanded configuration.
FIG. 20B illustrates the scaffold from FIG. 20A in an expanded configuration.

FIGS. 20A and 20B illustrate exemplary scaffold 500, with FIG. 20B showing the expanded configuration and FIG. 20A illustrating a flattened non-expanded configuration. Features that are shown in FIGS. 20A and 20B that are the same as features shown in other scaffolds herein may be expressly included in this embodiment even if not described herewith. Scaffold 500 includes proximal scaffold 510, central scaffold 520 and distal scaffold 530, which are unitary in this embodiment. In this embodiment the central scaffold 520 has a pattern and configuration such that it is less stiff in response to a radially inward force than proximal scaffold 510 and distal scaffold 530. Proximal scaffold 510 may be a proximal impeller scaffold, and distal scaffold 530 may be a distal impeller scaffold, within at least a portion of which a proximal impeller and a distal impeller may be disposed, respectively. Scaffold 500 central scaffold 520 has a pattern that is different than the pattern in scaffold sections 510 and 530. In this example, scaffold sections 510 and 530 have patterns that are substantially the same. Scaffold 500 includes circumferential connectors in proximal scaffold 510, central scaffold 520, and distal scaffold 530, as shown.

For example, proximal scaffold 510 includes circumferential connectors 512, and distal scaffold 530 includes circumferential connectors 532. The circumferential connectors in scaffold 500 have the same configurations as circumferential connectors 451 in the scaffold 450 in FIGS. 18A and 18B, and all descriptions thereof are incorporated by reference with the circumferential connectors into all scaffold sections in scaffold 500. For example only, circumferentially adjacent circumferential connectors are axially displaced (i.e., axially offset) relative to one another, which is described in more detail elsewhere herein. The circumferential connectors also have the S and inverse-S configurations, which is described with respect to other scaffolds herein. The central scaffold 520 in scaffold 500 also includes peaks 521 and 521', similar to peaks 478 in the scaffold in FIGS. 19A and 19B. A first plurality of peaks 521 have a first axial position, and a second plurality of peaks 521' have a second axial position, which can be seen clearly in FIG. 20A. The axial position alternates circumferentially around the scaffold, as shown. Peaks 521 and 521' extend from axially extending elements 522 like the scaffold in FIGS. 19A and 19B. The proximal scaffold and the distal scaffold do not include peaks in this embodiment. Axially extending elements 522 in the central scaffold section have a width that is greater than the width of the scaffold in peak 521 regions, as shown. This difference in width can provide the peak regions with greater flexibility, while the wider axially extending element provide sufficient radial support in the central scaffold. Any of the scaffold sections with the peaks may be considered a first region, and the axially adjacent sections with circumferential connectors and axially extending elements may be considered second regions, examples of which are described elsewhere herein. In this embodiment the axially extending elements are linear as shown, but may be curvilinear in other embodiments.

Figures 21A, 21B:
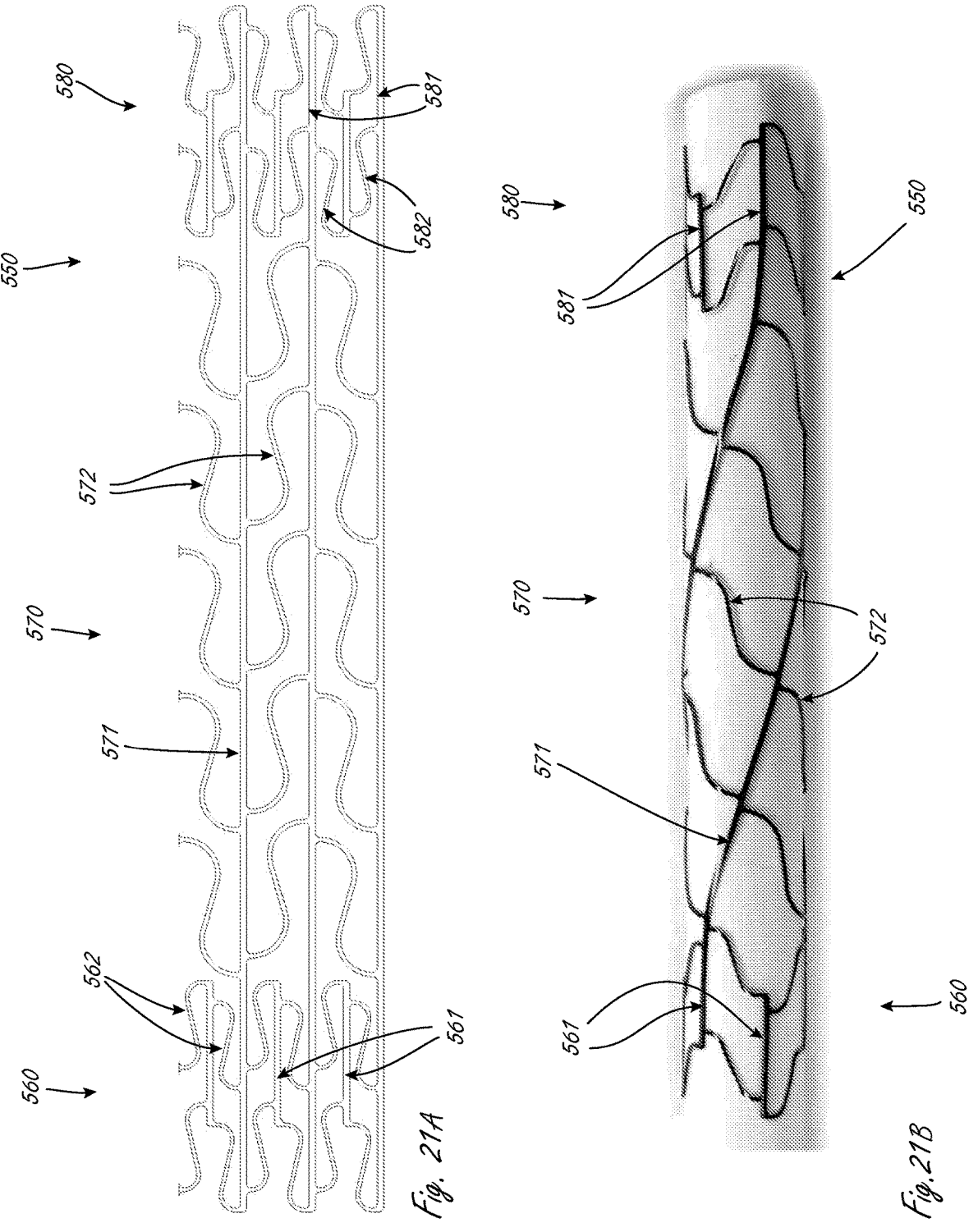
FIG. 21A illustrates an exemplary scaffold in a flattened and non-expanded configuration.
FIG. 21B illustrates the scaffold from FIG. 21A in an expanded configuration.

FIGS. 21A and 21B illustrate exemplary scaffold 550, with FIG. 21B showing the expanded configuration and FIG. 21A illustrating a flattened non-expanded configuration. Features that are shown in FIGS. 21A and 21B that are the same as features shown in other scaffolds herein may be expressly included in this embodiment even if not described herewith. Scaffold 550 includes proximal scaffold 560, central scaffold 570 and distal scaffold 580, which are unitary in this embodiment. Proximal scaffold 560 may be a proximal impeller scaffold, and distal scaffold 580 may be a distal impeller scaffold, within at least a portion of which a proximal impeller and a distal impeller may be disposed, respectively. Scaffold 550 central scaffold 570 has a pattern that is different than the pattern in scaffold sections 560 and 580. In this example, scaffold sections 560 and 580 have patterns that are substantially the same. Scaffold 550 includes circumferential connectors in proximal scaffold 560, central scaffold 570, and distal scaffold 580, as shown. For example, proximal scaffold 560 includes circumferential connectors 562, and distal scaffold 580 includes circumferential connectors 582. The circumferential connectors in scaffold 550 have the same configurations as circumferential connectors 451 in the scaffold 450 in FIGS. 18A and 18B, and all descriptions thereof are incorporated by reference with the circumferential connectors into all scaffold sections in scaffold 550. For example only, circumferentially adjacent circumferential connectors are axially displaced (i.e., axially offset) relative to one another, which is described in more detail elsewhere herein. The circumferential connectors also have the S and inverse-S configurations, which is described with respect to other scaffolds herein. Elements 571 in the central scaffold extend into the proximal and distal scaffold sections as shown, forming linear axially extending elements in the proximal and distal scaffolds. Axially extending elements 561 in proximal scaffold 560 do not extend into the central scaffold, as shown. Similarly, axially extending elements 581 in distal scaffold 580 do not extend into the central scaffold, as shown. Elements 571 in the central scaffold 570 have helical configurations as shown. Adjacent elements 571 are connected with connectors 572 as shown. Connectors 572 may have any characteristics of any circumferential connectors herein, such as the alternating S and inverse-S configurations. FIG. 21A illustrates a flattened non-expanded configuration, and the scaffold 550 may be formed into the configuration shown in FIG. 21B, such as by twisting the ends relative to one another and setting the scaffold in the configuration shown in FIG. 21B.

Figures 22A, 22B:
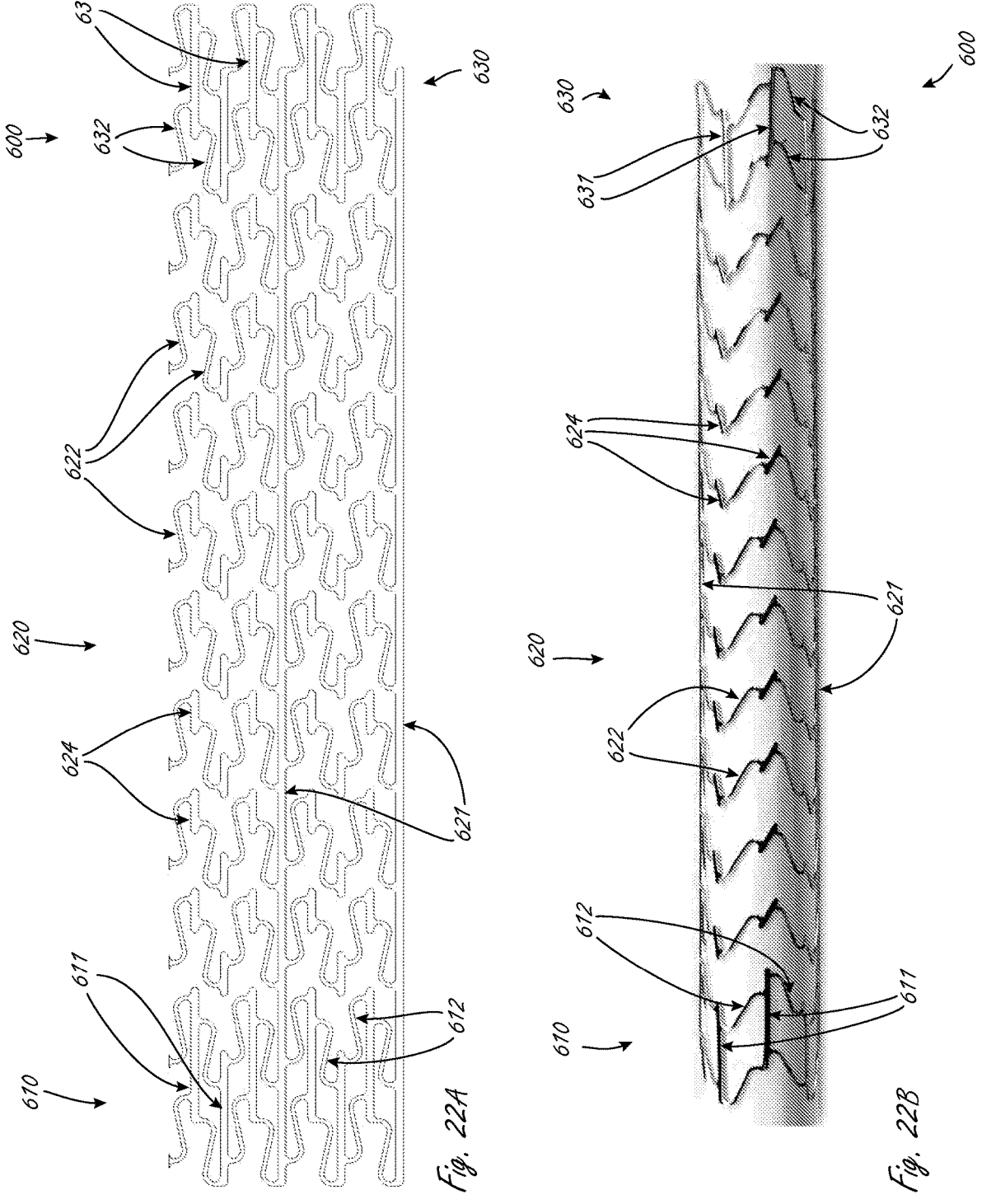
FIG. 22A illustrates an exemplary scaffold in a flattened and non-expanded configuration.
FIG. 22B illustrates the scaffold from FIG. 22A in an expanded configuration.

FIGS. 22A and 22B illustrate exemplary scaffold 600, with FIG. 22B showing the expanded configuration and FIG. 22A illustrating a flattened non-expanded configuration. Features that are shown in FIGS. 22A and 22B that are the same as features shown in other scaffolds herein may be expressly included in this embodiment even if not described herewith. Scaffold 600 includes proximal scaffold 610, central scaffold 620 and distal scaffold 630, which are unitary in this embodiment. Proximal scaffold 610 may be a proximal impeller scaffold, and distal scaffold 630 may be a distal impeller scaffold, within at least a portion of which a proximal impeller and a distal impeller may be disposed, respectively. Scaffold 600 central scaffold 620 has a pattern that is different than the pattern in scaffold sections 610 and 630. In this example, scaffold sections 610 and 630 have patterns that are substantially the same. Scaffold 600 includes circumferential connectors in proximal scaffold 610, central scaffold 620, and distal scaffold 630, as shown. For example, proximal scaffold 610 includes circumferential connectors 612, and distal scaffold 630 includes circumferential connectors 632. The circumferential connectors in the proximal and distal sections of scaffold 600 have the same configurations as circumferential connectors 451 in the scaffold 450 in FIGS. 18A and 18B, and all descriptions thereof are incorporated by reference with the circumferential connectors into all scaffold sections in scaffold 600. For example only, circumferentially adjacent circumferential connectors are axially displaced (i.e., axially offset) relative to one another, which is described in more detail elsewhere herein, and connect axially extending elements 611 and 631, respectively. The circumferential connectors also have S and inverse-S configurations, which is described with respect to other scaffolds herein. Axially extending elements 621 in the central scaffold extend into the proximal and distal scaffold sections as shown, wherein the elements 621 are linear axially extending elements in the proximal and distal scaffolds as well as the central scaffold. Axially extending elements 611 in proximal scaffold 610 do not extend into the central scaffold, as shown. Similarly, axially extending elements 631 in distal scaffold 630 do not extend into the central scaffold, as shown. Elements 621 in the central scaffold 620 have axially extending linear configurations as shown. Central scaffold 620 includes axially extending elements 621 that are connected by circumferential connectors. The circumferential connectors include a plurality of axially extending elements 624, each of which connect circumferentially adjacent circumferential connectors 622, as shown. When scaffold 600 is expanded to the configuration shown in FIG. 22B, the circumferential connectors assume the configuration shown, wherein elements 624 are no longer purely axially extending, such that they form an angle with a long axis of the scaffold, as shown.

Figure 23A:
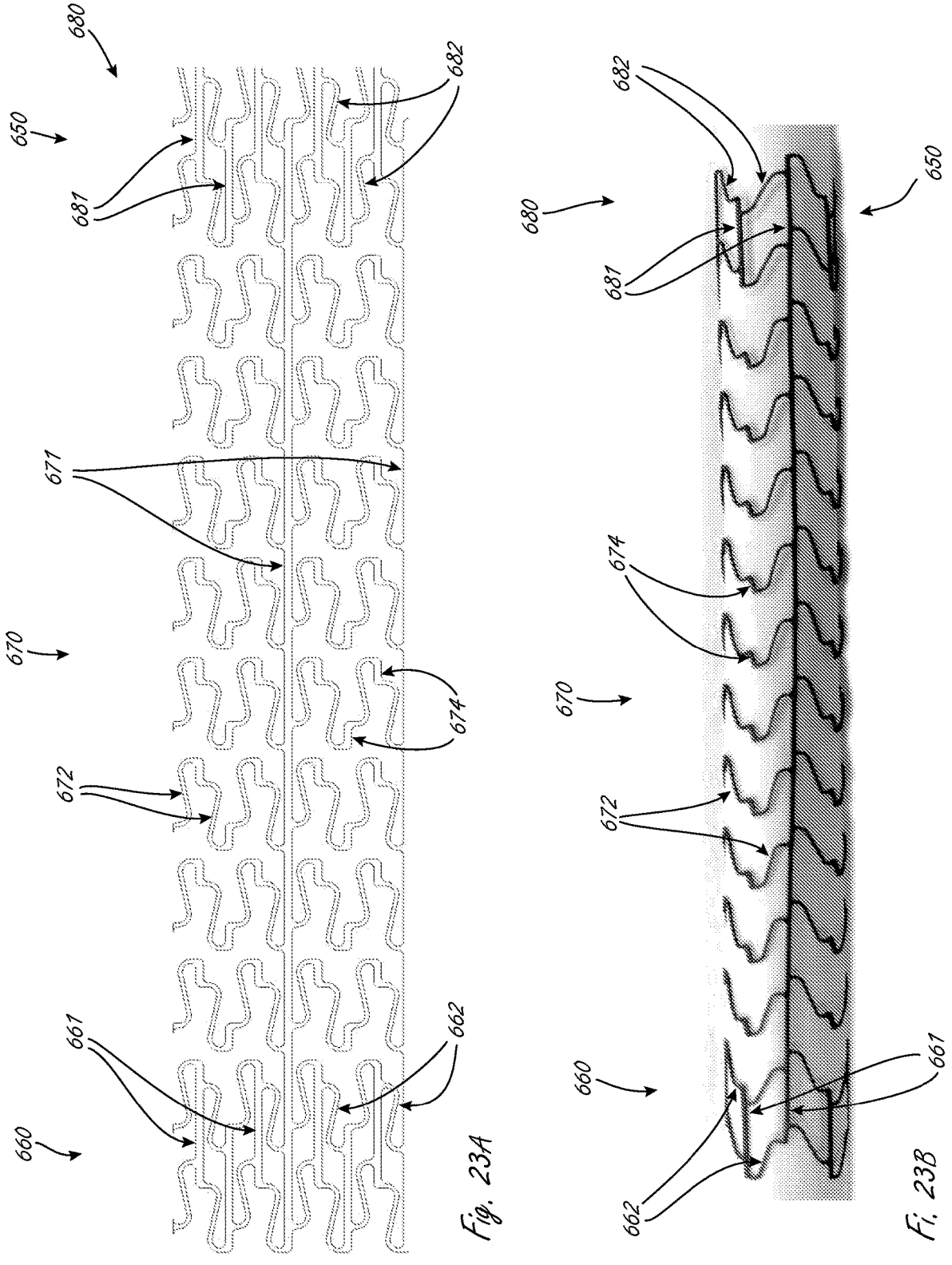
FIG. 23A illustrates an exemplary scaffold in a flattened and non-expanded configuration.

FIGS. 23A and 23B illustrate exemplary scaffold 650, with FIG. 23B showing the expanded configuration and FIG. 23A illustrating a flattened non-expanded configuration. Features that are shown in FIGS. 23A and 23B that are the same as features shown in other scaffolds herein may be expressly included in this embodiment even if not described herewith. Scaffold 650 includes proximal scaffold 660, central scaffold 670 and distal scaffold 650, which are unitary in this embodiment. Proximal scaffold 660 may be a proximal impeller scaffold, and distal scaffold 650 may be a distal impeller scaffold, within at least a portion of which a proximal impeller and a distal impeller may be disposed, respectively. Scaffold 650 central scaffold 670 has a pattern that is different than the pattern in scaffold sections 660 and 680. In this example, scaffold sections 660 and 680 have patterns that are substantially the same. Scaffold 650 includes circumferential connectors in proximal scaffold 660, central scaffold 670, and distal scaffold 680, as shown. For example, proximal scaffold 660 includes circumferential connectors 662, and distal scaffold 650 includes circumferential connectors 682. The circumferential connectors in the proximal and distal sections of scaffold 650 have the same configurations as circumferential connectors 451 in the scaffold 450 in FIGS. 18A and 18B, and all descriptions thereof are incorporated by reference with the circumferential connectors into all scaffold sections in scaffold 650. For example only, circumferentially adjacent circumferential connectors are axially displaced (i.e., axially offset) relative to one another, which is described in more detail elsewhere herein, and connect axially extending elements 661 and 681, respectively. The circumferential connectors also have S and inverse-S configurations, which is described with respect to other scaffolds herein. Axially extending elements 671 in the central scaffold extend into the proximal and distal scaffold sections as shown, wherein the elements 671 are linear axially extending elements in the proximal and distal scaffolds as well as the central scaffold. Axially extending elements 661 in proximal scaffold 660 do not extend into the central scaffold, as shown. Similarly, axially extending elements 681 in distal scaffold 650 do not extend into the central scaffold, as shown. Elements 671 in the central scaffold 670 have axially extending linear configurations as shown. Central scaffold 670 includes axially extending elements 671 that are connected by circumferential connectors. The circumferential connectors include a plurality of axially extending elements 674, each of which connect circumferentially adjacent circumferential connectors 672, as shown. When scaffold 650 is expanded to the configuration shown in FIG. 23B, the circumferential connectors 672 assume the configuration shown, wherein elements 674 are no longer purely axially extending, such that they form an angle with a long axis of the scaffold, as shown. Elements 674 in FIG. 23A are formed by removing material axially disposed between axially adjacent elements 674.

Figures 24A, 24B:
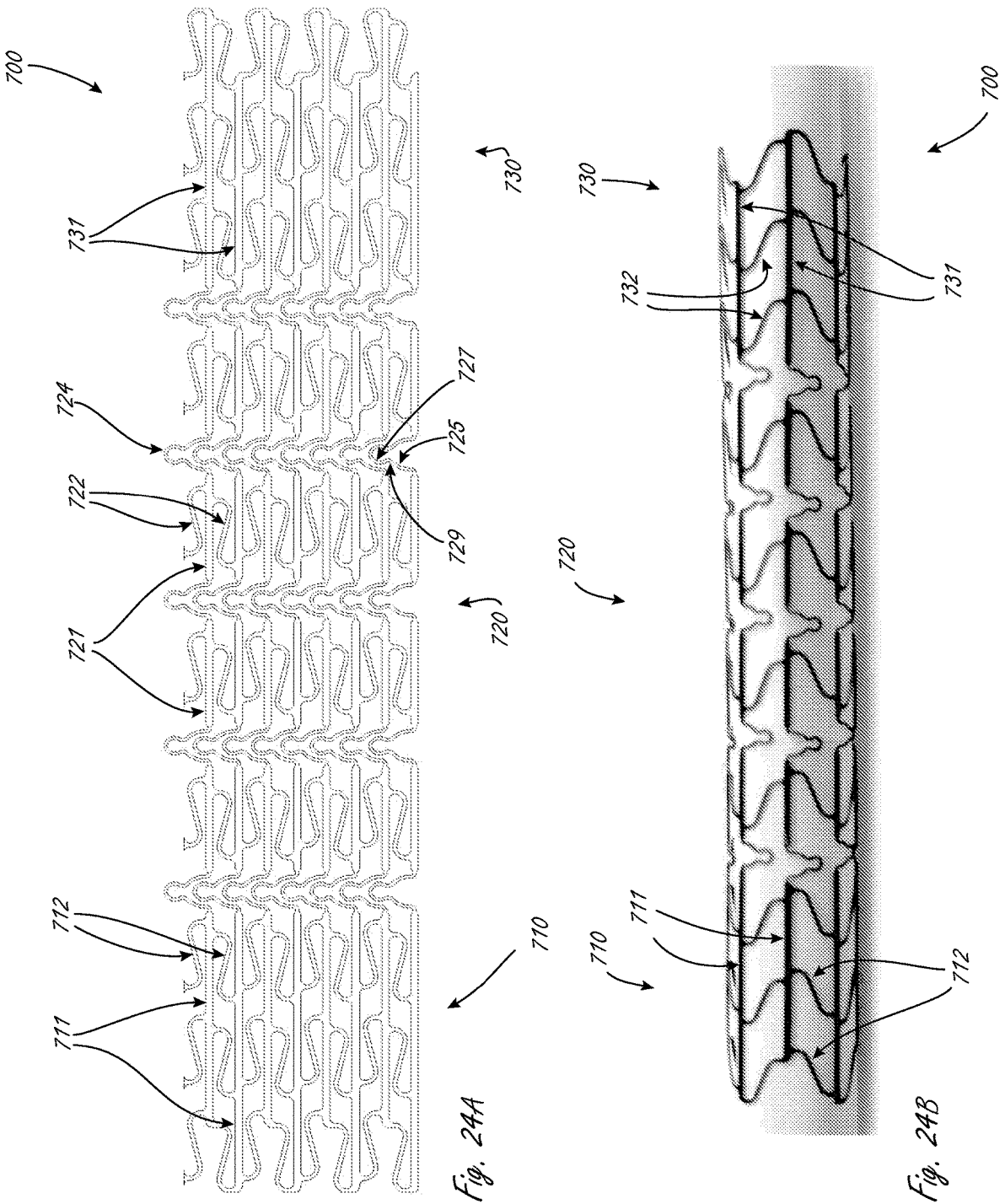
FIG. 24A illustrates an exemplary scaffold in a flattened and non-expanded configuration.
FIG. 24B illustrates the scaffold from FIG. 24A in an expanded configuration.

FIGS. 24A and 24B illustrate exemplary scaffold 700, with FIG. 24B showing the expanded configuration and FIG. 24A illustrating a flattened non-expanded configuration. Features that are shown in FIGS. 24A and 24B that are the same as features shown in other scaffolds herein may be expressly included in this embodiment even if not described herewith. For example, scaffold 700 is the same in some ways to the scaffolds shown in FIGS. 19A, 19B, 20A and 20B. Scaffold 700 includes proximal scaffold 710, central scaffold 720 and distal scaffold 730, which are unitary in this embodiment. Proximal scaffold 710 may be a proximal impeller scaffold, and distal scaffold 730 may be a distal impeller scaffold, within at least a portion of which a proximal impeller and a distal impeller may be disposed, respectively. Scaffold 700 central scaffold 720 has a pattern that is different than the pattern in scaffold sections 710 and 730. In this example, scaffold sections 710 and 730 have patterns that are substantially the same. Scaffold 700 includes circumferential connectors in proximal scaffold 710, in central scaffold 720, and in distal scaffold 730, as shown. For example, proximal scaffold 710 includes circumferential connectors 712, and distal scaffold 730 includes circumferential connectors 732. The circumferential connectors in the proximal and distal sections of scaffold 700 have the same configurations as circumferential connectors 451 in the scaffold 450 in FIGS. 18A and 18B, and all descriptions thereof are incorporated by reference with the circumferential connectors into all scaffold sections in scaffold 700. For example only, circumferentially adjacent circumferential connectors are axially displaced (i.e., axially offset) relative to one another, which is described in more detail elsewhere herein, and connect axially extending elements 711 and 731, respectively. The circumferential connectors also have S and inverse-S configurations alternating circumferentially around the scaffold, which is described with respect to other scaffolds herein. Scaffold 700 includes a plurality of axially extending elements 711, which are linear in sections but do not extend along the entire length of scaffold 700. Scaffold 700 also includes circumferential connectors 712 that circumferentially connect circumferentially adjacent axial elements 711. The proximal scaffold, central scaffold, and distal scaffold comprise a plurality of linear axially extending elements 711, 721, and 731, respectively, that are circumferentially spaced apart around the respective scaffold section, wherein first and second adjacent linear axially extending elements are each connected by a circumferential connector 712, 722, and 732, respectively, having at least one bend formed therein. The circumferential connectors define a plurality of circumferential connectors around the scaffold, and wherein circumferentially adjacent circumferential connectors of the plurality of circumferential connectors are displaced axially relative to one another, as shown and described elsewhere herein. As is the case in FIGS. 18A and 19B, a section of each one of the axially extending elements (in this example linear elements) connects circumferentially adjacent circumferential connectors that are axially displaced, as shown. FIGS. 24A and 24B illustrate a first group of a plurality of circumferential connectors having a first axial position, and wherein a second group of the plurality of circumferential connectors have a second axial position, wherein the first and second axial positions alternate circumferentially around the scaffold.

Scaffold 700 also includes a second region that is axially adjacent a first region, wherein the second region comprises a plurality of peaks 724 that are shown oriented orthogonally relative to a long axis of the scaffold 700. In this example, each of the plurality of peaks 724 is an extension of one of the axially extending elements 721, as shown. Scaffold 700 also includes a third region that is axially adjacent the second region, the third region comprising a second plurality of linear axially extending elements as shown that are spaced apart around the scaffold, and a second plurality of circumferential connectors 722, where the second region joins the first region and third region. In this embodiment, the second region includes first convex section 725 and second convex section 727, connected at location 729.

Figures 25A, 25B:
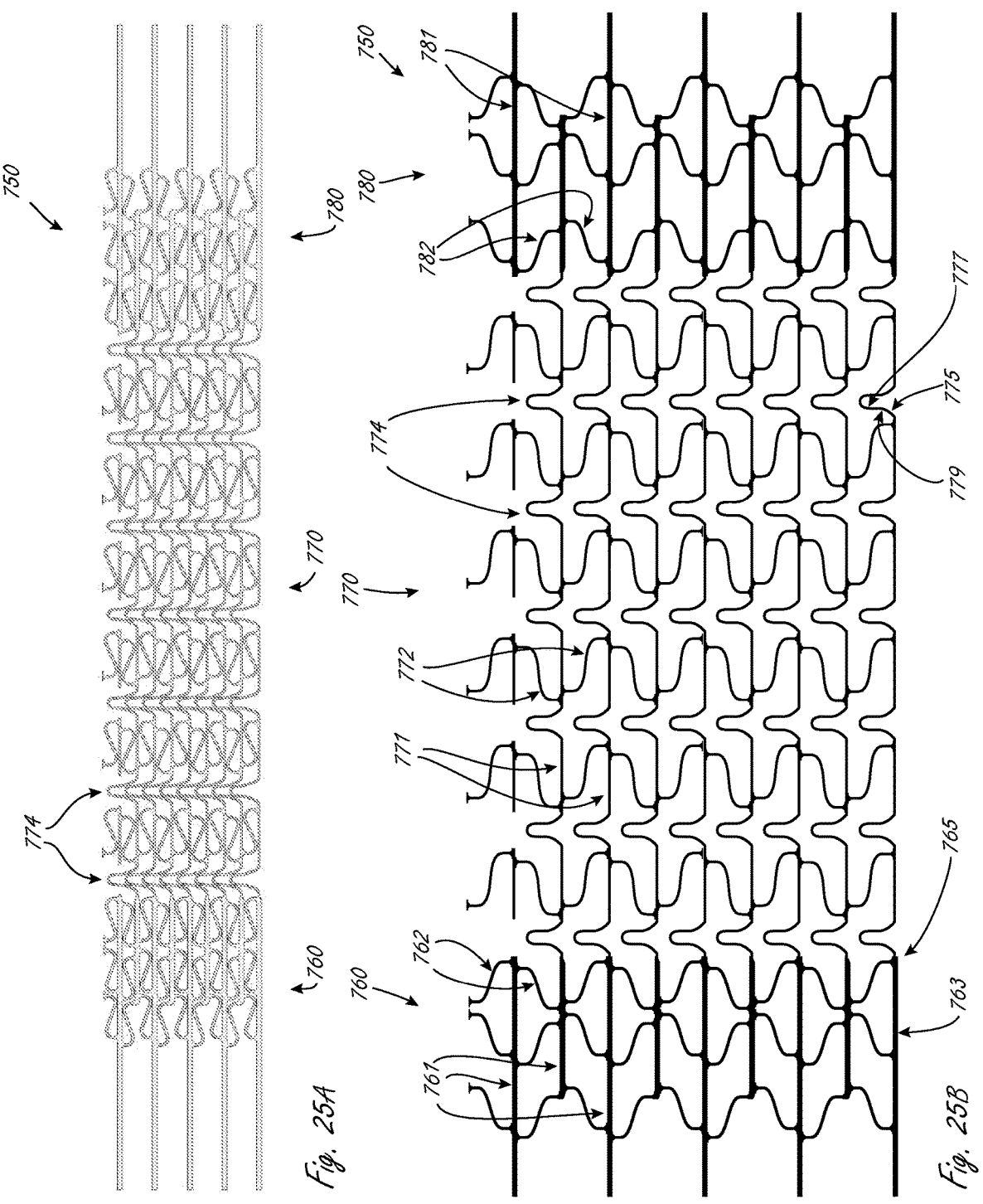
FIG. 25A illustrates an exemplary scaffold in a flattened and non-expanded configuration.
FIG. 25B illustrates the scaffold from FIG. 25A in an flattened expanded configuration.

FIGS. 25A and 25B illustrate an exemplary scaffold 750, which in this example includes a proximal scaffold 760, central scaffold 770 and distal scaffold 780, which are unitary. Scaffold 750 is similar in several ways to scaffold 700 in FIGS. 24A and 24B, the disclosure of which is completely incorporated by reference in the description of FIGS. 25A and 25B, any features of which may be included in scaffold 750. One difference is that scaffold 750 central scaffold 770 includes a first region that includes peaks 774, wherein the first region includes sections 775 and 777 connected at location 779, wherein sections 775 and 777 create a smoother curvilinear region than sections 725 and 727 in scaffold 700. An additional difference is that scaffold 750 includes proximal and distal scaffolds that both include mirrored sections, such as sections 763 and 765 as shown in FIG. 25B. The mirrored aspect refers to axially adjacent connectors 762 in section 763 that are mirrored with respect to connectors 762 in section 765. The same mirrored aspect is shown in distal scaffold 780. The mirrored sections in proximal scaffold 760 are closer to central scaffold 770 than the mirrored sections in distal scaffold 780, as shown.

In alternative embodiments, mirrored sections in a distal scaffold may be closer to a central scaffold than mirrored sections in a proximal scaffold. The description of all other aspects of scaffolds herein, including axially extending elements and circumferential connectors, are incorporated by reference herein into the scaffold 750. FIG. 25B shows a flat expanded configuration, while FIG. 25A shows a flat non-expanded configuration.

FIGS. 26A and 26B illustrate scaffold 800, which as shown includes many of the same features as scaffold 750 shown in FIGS. 25A and 25B. FIG. 26A illustrate a flattened unexpanded configuration, while FIG. 26B illustrates transition region 801 of scaffold 800 called out in FIG. 26A. A difference between the scaffolds is that in FIGS. 26A and 26B, proximal scaffold 810 includes mirrored sections that are further from central scaffold 820 than mirrored section in distal scaffold, as shown. FIG. 26B illustrates a transition region between proximal scaffold 810 and central scaffold 820. Scaffold 800 includes orthogonally oriented peaks 824 as described elsewhere herein. Scaffold first regions includes sections 825 and 827, which may be the same as sections 775 and 777 in scaffold 750. FIG. 26B illustrates the widths of axially extending elements 811 being greater than the widths of elements 821 in central scaffold, as shown. The thickness measurements are into the page in the figures (in the "z" direction), while the width measurements are in the plane of the page in the figures shown. One thickness "t" of element 811 is labeled for reference. As shown, the thickness "t" of element 811 is greater than the thickness of elements 821 in the central scaffold section.

Figures 27A, 27B:
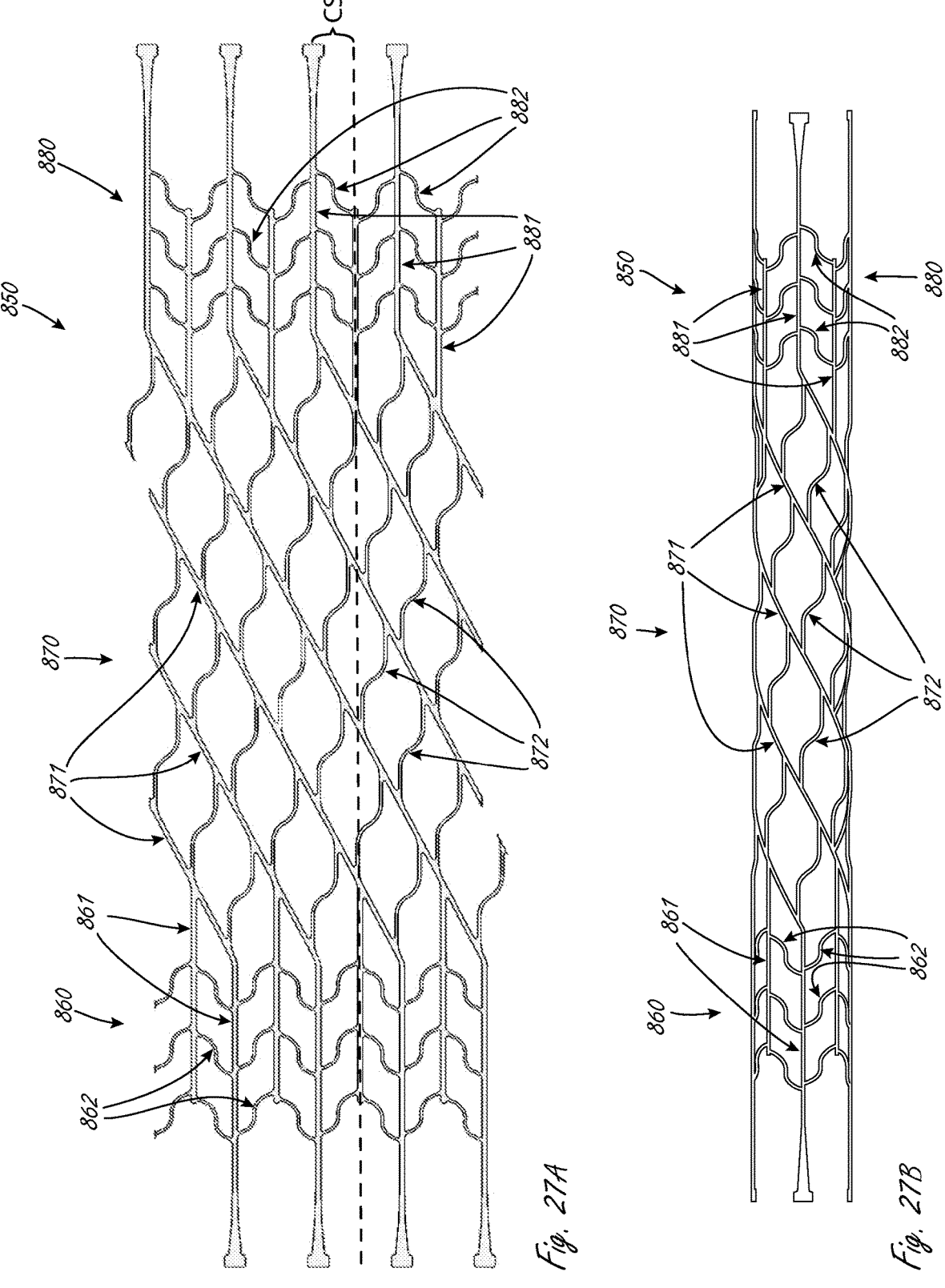
FIG. 27A illustrates an exemplary scaffold in a flattened and non-collapsed configuration.
FIG. 27B illustrates the scaffold from FIG. 27A in a non-collapsed configuration.

FIGS. 27A and 27B illustrate exemplary scaffold 850, which is similar in several ways to scaffold 550 shown in FIGS. 21A and 21B. Scaffold 850 includes proximal scaffold 860, central scaffold 870 and distal scaffold 880, which in this embodiment may be unitary. Scaffold 850 central scaffold 870 includes helical elements 871 in the non-collapsed configuration (FIG. 27A) and the wrapped configuration (FIG. 27B). In this and any other embodiment herein the scaffold may be manufactured (e.g., including laser cutting of a tubular member) such that the expanded configuration is the configuration is which the scaffold is laser-cut from the tubular member. This is in contrast to any examples herein in which the scaffold is laser cut from a smaller diameter tubular member, and then expanded and set into an expanded configuration. In any of the embodiments herein, a laser cut diameter may be equal to a non-collapsed diameter to, for example without limitation, provide better concentricity. This may also allow coating of a membrane to adhere to struts and have a smoother inner diameter.

Proximal scaffold 860 and distal scaffold 880 have substantial the same configuration, but they are displaced circumferentially by circumferential spacing "CS" (labeled in FIG. 27A). Adjacent helical elements 871 are connected by connectors 872. All other similar aspect of other scaffolds herein may be incorporated herein, including, by way of example only, the axially offset nature of circumferentially adjacent circumferential connectors in proximal scaffold 860 and distal scaffold 880.

FIG. 27A illustrates exemplary distal and proximal struts extending axially from the scaffold, only one strut of which 865 is labeled. In this example there are four proximal and four distal struts. As shown, the struts are tapered and are wider at ends further from the scaffold, which may increase stability over the impellers compared to struts that have a constant width over their entire length. Any of the pump portions herein may include any number of struts that have the same configuration as struts 865.

In any of the embodiments herein, the scaffold may be cut from a tubular member that has an expanded scaffold diameter. In these embodiments, the tubular member has a diameter that is the same or substantially the same as the desired scaffold deployed configuration (un-sheathed). Alternatively, in any of the embodiments herein, the scaffold may be cut from a tubular member that has a non-expanded scaffold diameter. In this embodiments, the tubular member has a diameter less than a scaffold expanded diameter, and after being cut the scaffold may be expanded set in the expanded deployed configuration.

In any of the embodiments herein, a distal scaffold may have a length that is greater than a length of a proximal scaffold. In any of the embodiments herein, a distal scaffold may have a length that is less than a length of a proximal scaffold. In any of the embodiments herein, a distal scaffold may have a length that is the same as a length of a proximal scaffold.

In any embodiment herein, a central scaffold may have a length that is greater than a length of one or both of a proximal scaffold and a distal scaffold.

Any of the different scaffold sections herein may be connected with one or more welds, and may not be unitary with each other.

In any of the embodiments herein, any section or sections of the scaffold may have a thickness (measured radially between a scaffold inner diameter and a scaffold outer diameter) that is the same as or different than a thickness of any other section of the scaffold. For example, a thickness of a scaffold section may be decreased by electropolishing one or more sections more than other sections (which may include no electropolishing). Varying the thickness may be in addition to or alternative to varying the width, which may allow for more design options, as may be desired.

In any of the embodiments herein, an axial distance between proximal and distal scaffold sections may be from 30 mm to 50 mm, such as from 35 mm to 45 mm In any of the embodiments herein, the pump portion may be from 40 mm and 80 mm, such as from 50 mm to 70 mm, such as from 55 mm to 65 cm.

In any of the embodiments herein that include first and second impellers, an axial distance between impellers may be from 40 mm to 60 mm, such as from 45 mm to 55 mm In any of the embodiments herein, a diameter of the expanded (or non-collapsed) blood conduit may be from 6 mm to 8.5 mm, such as from 6 mm to 8 mm, such as from 6.5 mm to 7.5 mm In any of the embodiments herein, a diameter of any of the impellers when expanded may be from 5 mm to 7 mm, such as from 5.5 mm to 6.5 mm.

The disclosure below is related to intravascular blood pumps that are configured to be collapsible for delivery to a target location and expandable to a larger operational configuration, wherein the blood pumps further include an expandable flow diverter in the outflow of the pump.

Figure 28A:
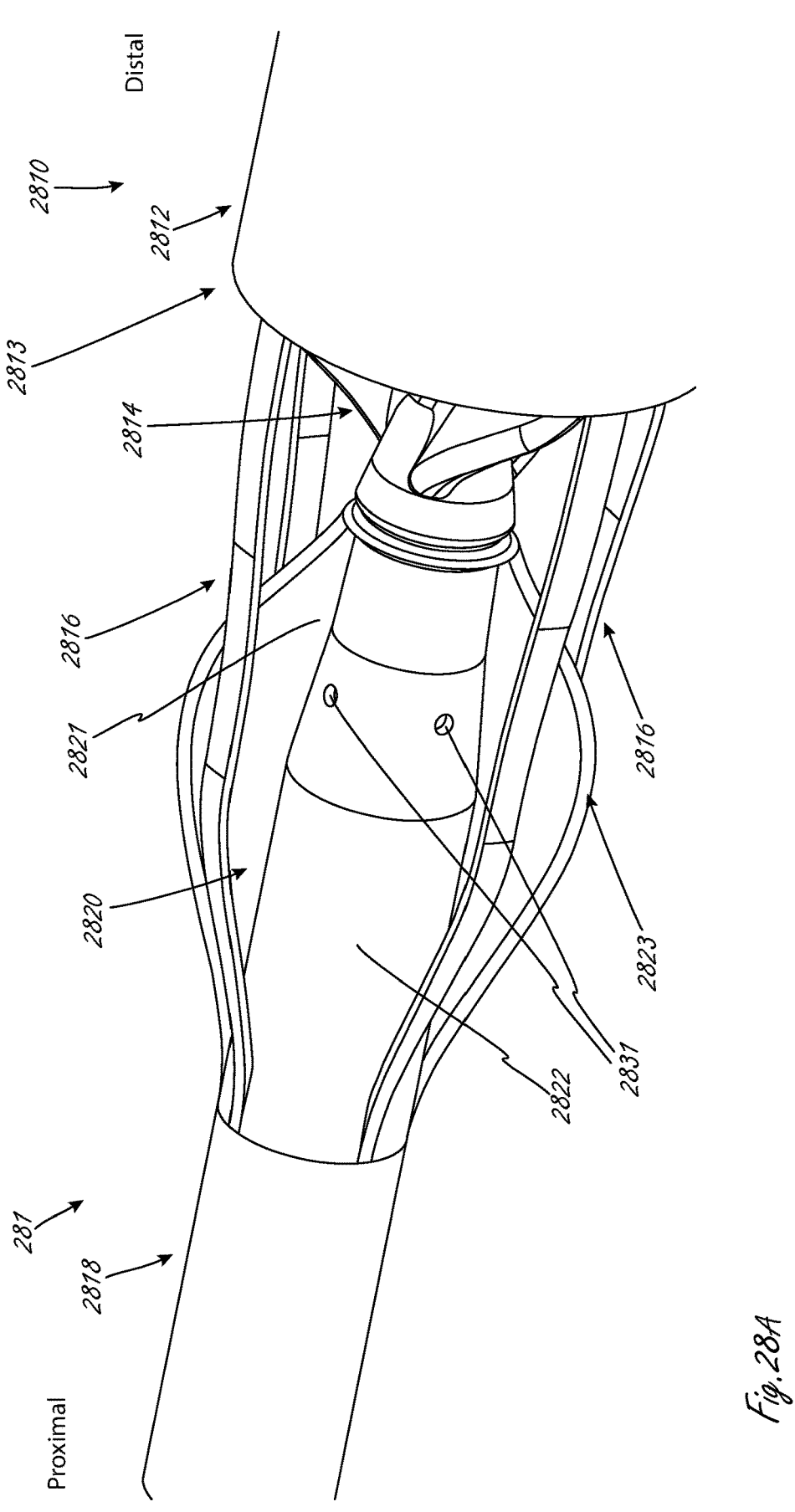
FIG. 28A illustrates an outflow of a catheter blood pump with an expanded flow diverter positioned in the outflow.

FIG. 28A illustrates a perspective partial view of an exemplary blood pump 281, including pump portion 2810. Pump portion 2810 includes blood or fluid conduit 2812 shown in an expanded configuration. Exemplary details of fluid conduits can be found herein, such as one or more scaffold or reinforcing sections and for example, one or more membrane layers secured to scaffold(s) that at least partially define a fluid lumen of the conduit. Pump portion 2810 also includes one or more impellers 2814. FIG. 28A shows impeller 2814, and it is understood that pump portions herein may include one or more (e.g., three) impellers. In the exemplary embodiment in FIG. 28A, impeller 2814 may be a first impeller, such as any of the proximal impellers herein, and pump portion 2810 may also include one or more additional impellers, such as any of the distal impellers herein. As shown, a proximal portion of impeller 2814 extends proximally beyond a proximal end 2813 of fluid conduit 2812, while a distal portion of impeller 2814 is disposed within the fluid conduit.

Figure 28B:
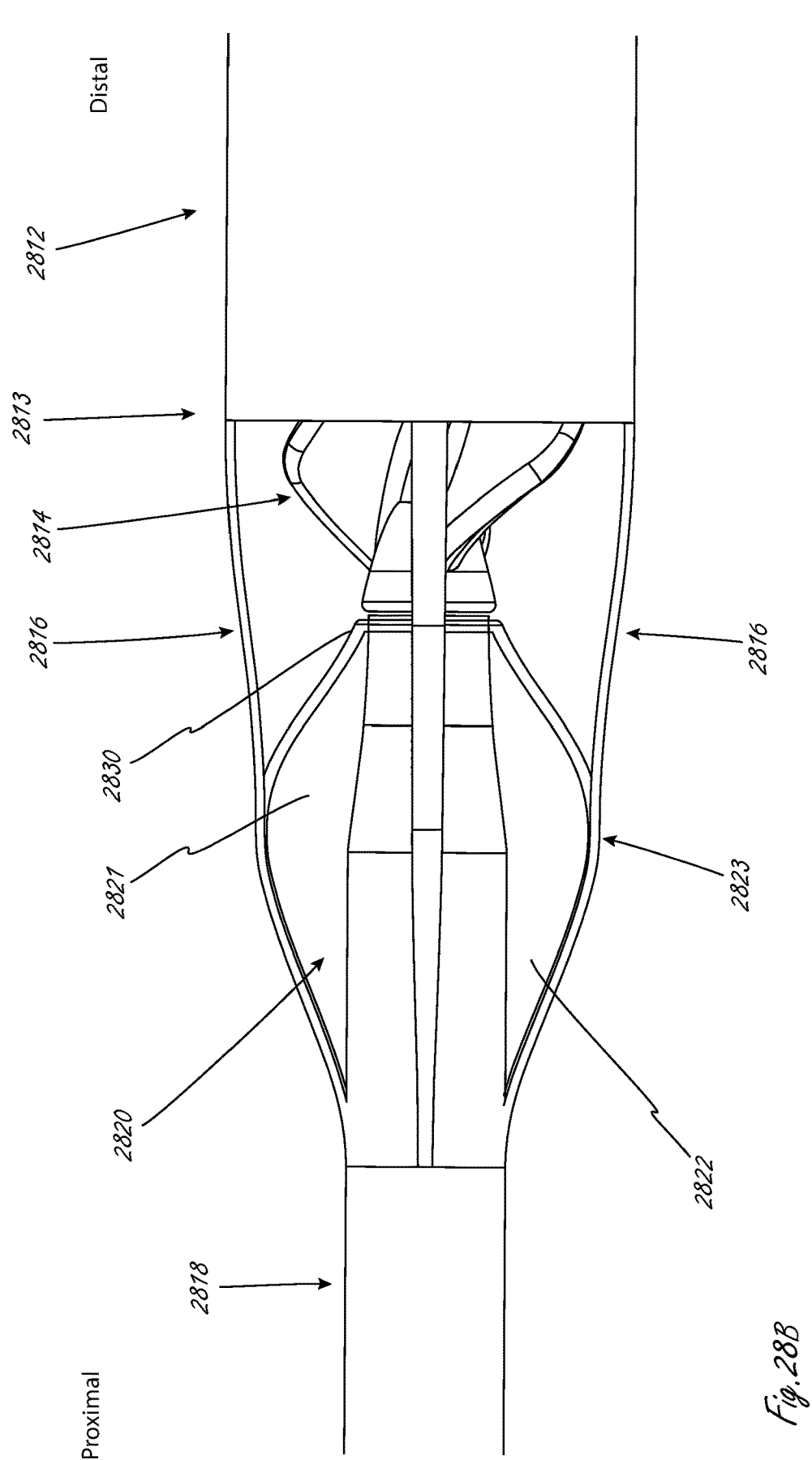
FIG. 28B is a side view of the outflow region from FIG. 28A.
Figure 28C:
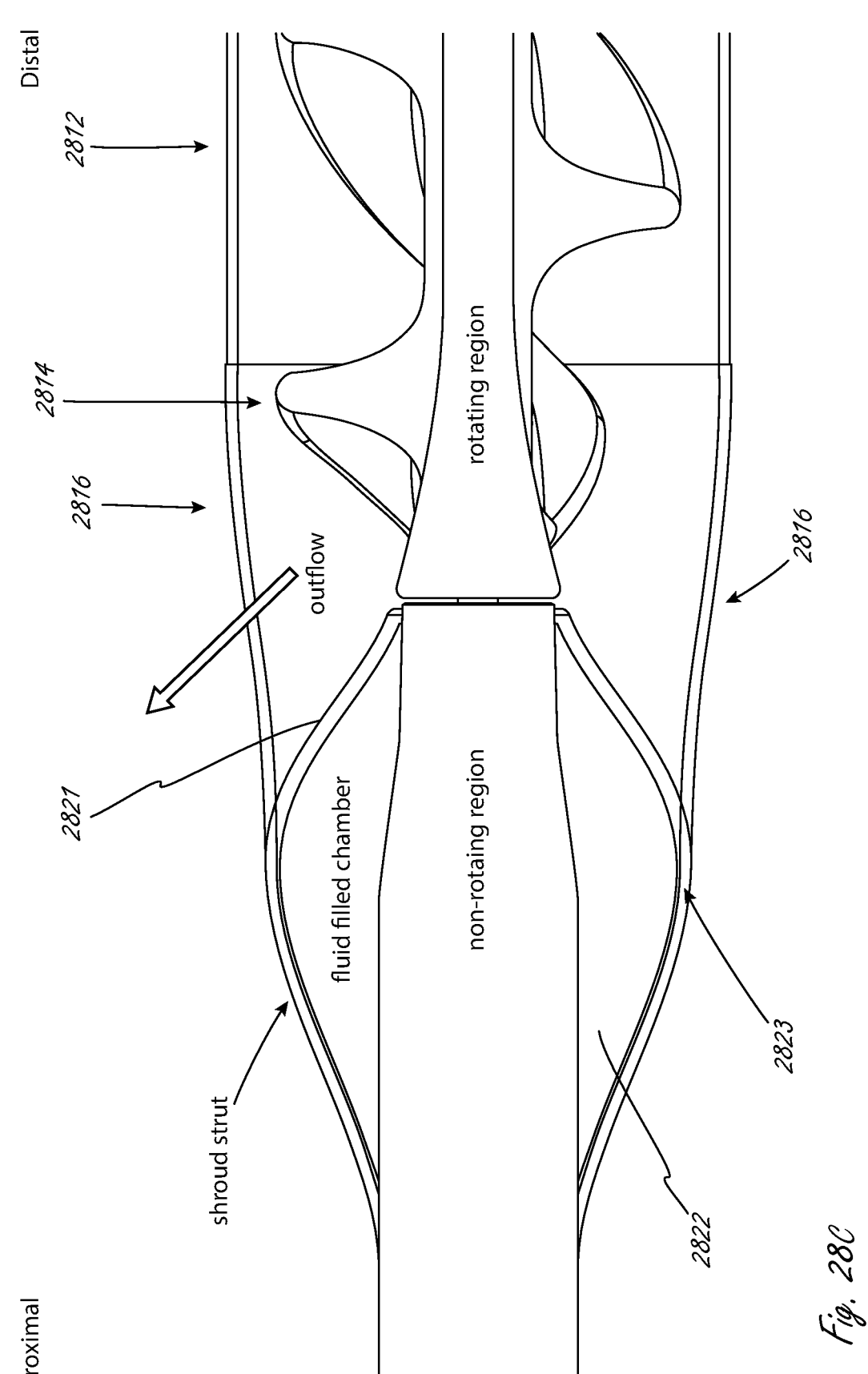
FIG. 28C is a side view of the outflow region from FIG. 28B.

FIG. 28B illustrate substantially the same partial view from FIG. 28A, but is a side view. FIG. 28C is a sectional view of the side view shown in FIG. 28B, including additional descriptions of exemplary and optional aspects.

Fluid conduit 2812 and impeller 2814 are each shown in expanded configurations in FIGS. 28A-28C. As set forth in more detail above, the pump portions herein may be deployed from collapsed configurations by proximal retraction of a sheath or other delivery member. Blood pump 281 also includes an expandable flow diverter 2820, which is shown in an expanded configuration in FIGS. 28A-28C. The expandable flow diverters herein are adapted to collapse to at least some extent to facilitate delivery of the pump portion, and are adapted to expand or be expandable (including any combination of self-expansion, active expansion, and partial self-expansion and partial active expansion) for pump operation.

Expandable flow diverter 2820 is not configured to rotate with impeller 2814. In this embodiment, flow diverter 2820 is non-rotating when the impeller is rotated during pump operation. As such, flow diverter 2820 is rotationally uncoupled from impeller 2814 (and uncoupled from a distal impeller if included in the pump portion).

The expanded flow diverters herein may be configured (e.g., shaped) to provide one or more benefits when they are expanded when the pump is being operated. An exemplary benefit is that the expanded flow diverters can be sized, shaped and axially disposed to reduce a recirculation/separation zone proximal to the pump portion outflow, which can beneficially lower hemolysis. For example, the flow diverter in FIGS. 28A-28C is disposed completely outside of the fluid conduit 2812 (and also proximal to impeller 2814, a portion of which is outside of fluid conduit 2812), and has a outer profile that defines the size and shape of the flow diverter. Another exemplary benefit to expanded flow diverter is that it can provide a more efficient radial flow component, which can aid in the generation of static pressure. FIG. 28C illustrates an arrow indicating exemplary outflow pathway, illustrating an increase in radial component compared to a similar pump without the flow diverter. FIGS. 28B and 28C also illustrate the volume occupied or taken up by the presence of the expanded flow diverter 2820, illustrating how it can reduce a recirculation/separation zone proximal to the pump portion outflow. An additional benefit of the flow diverters herein is that they are also configured to be collapsed for delivery into a smaller profile, which helps reduce their delivery profile.

The term "flow diverter" herein (even in the claims) is not meant to limit the functions or benefits that may be provided by their presence. For example, any of the expandable flow diverters herein may alternatively be referred as a recirculation zone reducer and/or a hemolysis reducer, or derivatives thereof.

Exemplary flow diverter 2820 includes a distal surface 2821 that increases in radial dimension in a distal to proximal direction. Distal surface 2821 may be substantially linear, it may be curved, or a combination thereof. In some embodiments any of the distal surfaces herein (e.g., surface 2821) may be referred to as ramped, but this does not necessary impart a particular shape to the surface. Surface 2821 helps increase a radial flow component, as shown in FIG. 28C. Distal surface 2821 leads to peak region 2823, which leads to proximal surface 2822 of the flow diverter. Proximal surface 2822 generally decreases in radial dimension in a distal to proximal direction. Proximal surface 2822 may be substantially linear, it may be curved, or a combination thereof. In some embodiments any of the proximal surfaces herein (e.g., surface 2822) may be referred to as ramped, but this does not necessary impart a particular shape to the surface.

Flow diverting surfaces herein refer to surfaces of a flow diverter that function to modify flow from the impeller, and may be configured to modify flow from the impeller. In some embodiments, the flow diverting surfaces may increase a radial flow component. Distal surface 2821 is a non-limiting example of a flow diverting surface.

In some embodiments, flow diverters herein may function to increase a radial blood flow component, compared to blood flow without the flow diverter. An increase in a radial flow component may occur at a location proximal to a proximal end of the fluid conduit.

Flow diverters herein may be non-bladed in that they may not include blades or vanes. Flow diverter 2820 is an example of a non-bladed flow diverter.

The axial length (parallel to long axis of pump portion) of surface 2821 may be shorter than the axial length of proximal surface 2822. That is, surface 2821 may be considered generally steeper than surface 2822 (which does not require a constant slope on either surface). A steeper curve to surface 2821 may help increase radial flow more abruptly proximal to the fluid conduit, where proximal surface 2822 may have a more gentle reduction in radial dimension.

In any of the embodiments herein, including the embodiment in FIGS. 28A-28C, flow diverter may be considered to have a bulbous shape when in an expanded configuration.

Expanded flow diverter 2820 is an example of a flow diverter that has an outer profile that is substantially or generally axisymmetric (revolved 360 degrees around the long axis).

The axial position of the flow diverters herein can help provide its beneficial functions. For example, as shown in exemplary FIGS. 28A-28C, distal surface 2821 is disposed completely proximal to the fluid conduit 2812. Positioning the distal surface 2821 near, but completely proximal to the fluid conduit 2812, allows the outflow to be unimpeded at the proximal end 2813 of conduit 2812, while still creating an increase in the radial flow component with surface 2821 proximal to the fluid conduit 2812. In the figures herein, the entirety of the flow diverter is outside of the fluid conduit.

In some variations not shown, a portion of the flow diverter may extend into the fluid conduit, such as a distal portion of distal surface 2821. In these variations, a peak region of the flow diverter, such as peak region 2823, and the entirety of a proximal surface (e.g., proximal surface 2822) may be disposed outside of and proximal to the fluid conduit. In FIGS. 28A-28C, impeller 2814 could be disposed completely within the fluid conduit to allow space for a portion of the flow diverter to be disposed in the fluid conduit.

Impeller 2814, as shown, has a proximal region that extends proximally outside of the fluid conduit. The impellers herein may have a proximal end region that includes a hub with a diameter that increases gradually in an axial direction, distal to proximal, an example of which is shown in FIGS. 28A-28C. In FIGS. 28A-28C, the radially outer surface of the proximal hub region is configured to provide a gradual and smoother (less abrupt) transition to an outer surface of flow diverter 2820, in this embodiment distal surface 2821. There can be a small gap between the impeller and the flow diverter, as shown in FIGS. 28B and 28C, to prevent friction and wear of parts when the impeller is rotated at relatively high speeds.

In some embodiments an outermost radial dimension of the flow diverter, relative to a long axis of the pump portion, may be at least 25% of an outermost radial dimension of the adjacent impeller (e.g., impeller 14). The outermost radial dimension of the adjacent impeller will generally be an outermost dimension of an impeller blade. In some embodiments an outermost radial dimension of the flow diverter, relative to a long axis of the pump portion, may be at least 55% of an outermost radial dimension of the adjacent impeller, and in some embodiments at least 60%, in some embodiments at least 65%, in some embodiments at least 70%, in some embodiments at least 75%, in some embodiments at least 80%, in some embodiments at least 85%, in some embodiments at least 90%, in some embodiments at least 95%. In some embodiments, an outermost radial dimension of the flow diverter, relative to a long axis of the pump portion, may be at least 100% or more of an outermost radial dimension of the adjacent impeller.

With any of these examples, an upper limit of the outermost radial dimension of the flow diverter may be 150%, 200%, 250%, or 300% of the outermost radial dimension of the adjacent impeller. The embodiment in FIGS. 28A-28C is an example of a blood pump with a flow diverter that is at least 55% of, at least 60% of, at least 65% of, at least 70% of, at least 75% of, at least 80% of, at least 85% of, at least 90% of, at least 95% of, and at least 100% or more of an outermost radial dimension of the adjacent impeller. An exemplary benefit of flow diverters that have any of the these outermost expanded dimension (but not necessarily limited to those set forth herein) is that it can be large enough to create a significant enough increase in the radial flow components. Flow diverters that have relatively very small outer radial dimensions will create less of an impact on radial flow, and will occupy less volume thus have less of an impact in reducing a recirculation/separation zone proximal to the pump portion outflow.

The flow diverters herein are configured to be collapsed for delivery, and are configured to be expandable to an operation or deployed configuration. The flow diverters herein may be at least partially self-expandable. The flow diverters herein may be at least partially expanded with an active expansion mechanism, such as mechanical, pneumatic, and/or hydraulic.

Flow diverters herein may be at least partially self-expandable. Flow diverters herein may comprise one or more materials that help facilitate at least partial self-expansion, such as, for example without limitation, a polymeric material or other materials with self-expanding properties such as nitinol. The flow diverters can be relatively thin-walled, which may help facilitate self-expansion.

In the embodiment in FIGS. 28A-28C, proximal portions of struts 2816 are secured to the flow diverter, while more distal portions of struts are not, as is shown. As described in FIG. 28C, the expanded struts 2816 may help expand flow diverter 2820 to some extent due to the secured interface, and they can also help maintain the shape of the flow diverter. Struts 2816 may comprise a self-expanding material such as nitinol, for example, and have distal end regions secured relative to the fluid conduit.

Additionally, or alternatively, the blood pump can be configured such that a flow diverter may be configured to be expanded at least partially with a pneumatic expansion mechanism and/or hydraulic expansion. For example, any of the flow diverters can have an inner volume in fluid (liquid and/or gas) communication with a fluid source. The fluid source can house a fluid that is delivered to the inner volume to expand the flow diverter. Any of the flow diverters herein may be configured and adapted such that they leak or weep some volume of fluid from an inner volume to a location outside of the flow diverter (e.g., via a plurality of pores).

The flow diverters may be secured to the blood pump using, for example, a variety of balloon catheter and balloon bonding techniques. The distal ends of the flow diverter can be secured to the blood pump, and as such the flow diverter is considered to have a closed distal end, which may help expand the flow diverter and maintain a desired expanded configuration, particularly if it is filled with fluid.

An additional aspect of the disclosure relates to outflow regions of intravascular blood pumps, and the structure of the end of the blood conduits at or adjacent the outflow. Pump outflows can be a transition region from a blood pump fluid conduit to a larger vessel (e.g., ascending aorta), and the transition may results in fluid losses and a decrease in pump performance, such as without limitation, increases in turbulent flow. It may be beneficial for pump portions of intravascular blood pumps to have outflow regions that are adapted and configured to reduce fluid losses and minimize decreases in pump performance The disclosure that follows relates to intravascular blood pumps and outflow regions thereof that are configured to decrease fluidic losses and/or increase performance at the pump outflow. As used herein, the decrease(s) are compared generally to blood conduits that have circular ends, such as of a cylindrical proximal end region of a blood conduit. Aspects described below may be incorporated into any of suitable blood pump herein, and vice versa.

In some embodiments, the pump portion is adapted to decrease fluidic losses and/or increase performance at the pump outflow due at least partially to a configuration of a proximal end region of a fluid conduit of the pump. For example, the configuration of the proximal region can be such that it reduces eddy currents and drag, compared to circular ends (e.g., of a cylindrical fluid conduit proximal end region).

Blood conduits herein may have a proximal end that is defined by a configuration that is non-circular. In some embodiments herein, the blood conduit has a proximal end region (that includes a blood conduit proximal end) that is defined by a configuration that is non-cylindrical. Blood conduits herein may have a proximal end that has an undulating configuration. Fluid conduits herein may have a proximal end that defines a non-degenerate two dimensional surface. For example, the fluid conduit in exemplary FIG. 1 is an example of a fluid conduit with a non-circular proximal end. Additionally, for example, the fluid conduit in exemplary FIG. 1 is an example of a fluid conduit with a non-cylindrical proximal end region.

Figure 29:
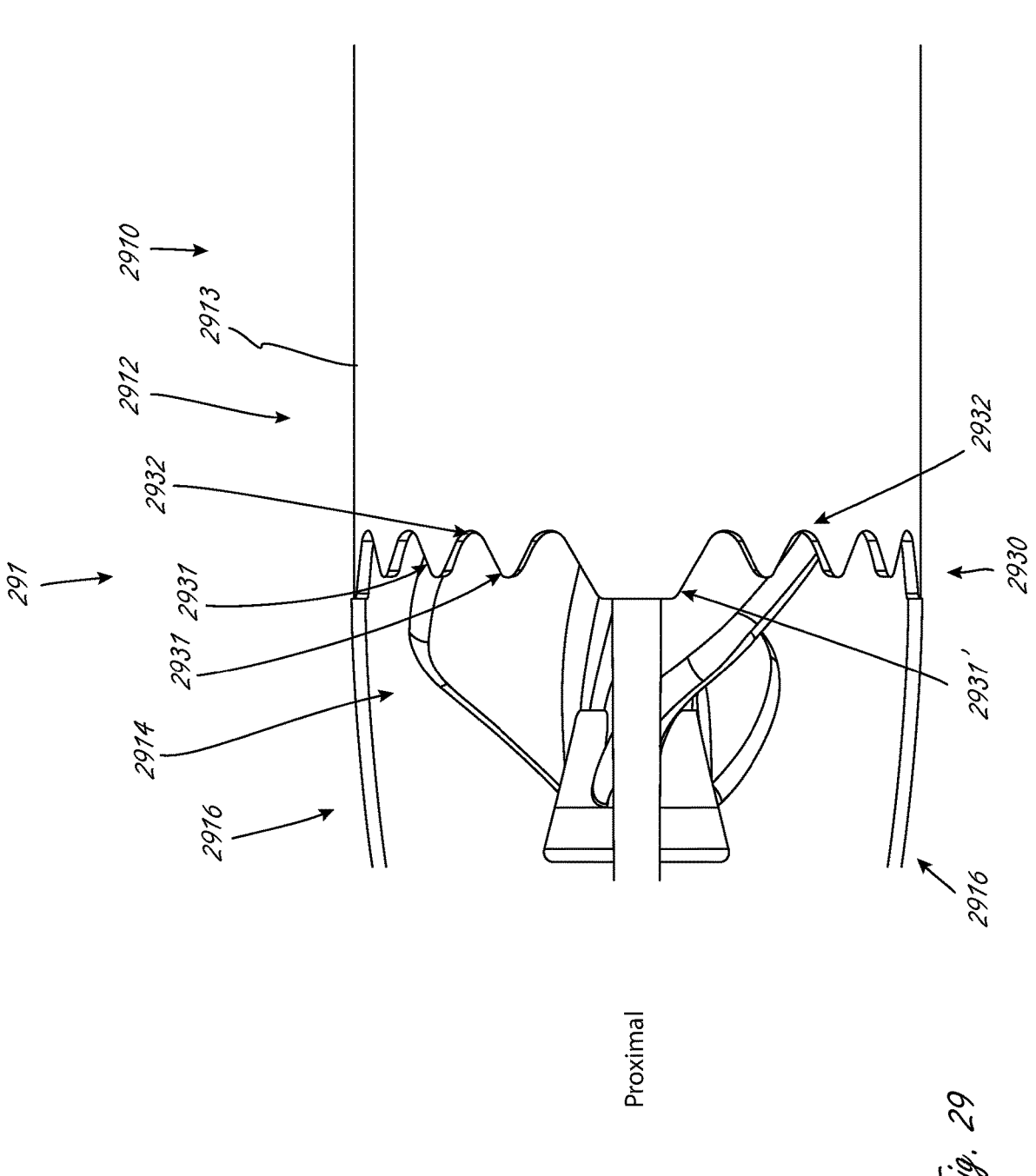
FIG. 29 illustrates an exemplary outflow region of a pump portion of a catheter blood pump.

FIG. 29 is a side view, illustrating a portion of exemplary blood pump 291. Blood pump 291 may also include any other aspect or feature described herein, unless indicated to the contrary. Blood pump 291 includes collapsible and expandable pump portion 2910, only a proximal portion of which is shown. Pump portion 2910 includes a collapsible and expandable blood conduit 2912 and a collapsible and expandable impeller 2914. The blood pump 291 includes proximal fluid conduit struts 2916 (only two are labeled), which extend proximally from the blood conduit 2912.

Exemplary blood conduit 2912 includes a proximal end 2930. Proximal end 2930 has a configuration that can decrease fluidic losses and/or increase performance at the pump outflow compared to circular end (e.g., of a cylindrical end region of a comparable blood conduit). In this exemplary and particular embodiment, proximal end 2930 has a configuration that includes protrusions 2931 and depressions 2932 extending around the proximal end 2930. In this particular embodiment, the protrusions and depressions are alternating around the proximal end. Proximal end 2930 may also simply be considered to have protrusions 2931 that extend proximally, without necessarily requiring that depressions be considered separate features. That is, the protrusions may be considered to inherently create depressions. In this example, the proximal end includes protrusions with curved peaks. In variations, the proximal end of the fluid conduit may have a sawtooth pattern, with sharper peaks, for example.

The configuration of proximal end 2930 can be in contrast to a circular end of a fluid conduit. If the fluid conduit proximal end is circular, blood flow out of the fluid conduit may have a substantially lower pressure than the blood flowing around the fluid conduit, which may cause more eddy currents and increase the amount of drag. The configuration of proximal end 2930 with the alternating protrusions and depressions is an example of an end configuration that may decrease fluidic losses and increase pump performance compared to a fluid conduit proximal end that is circular.

In this exemplary embodiment, a proximal portion of impeller 14 optionally extends further proximally than a proximal end of the fluid conduit 2912, as shown, and additional exemplary aspects of which are described herein.

Fluid (or blood) conduits herein may include one or more layers of material, at least an innermost portion of which can at least partially define an inner surface of the fluid conduit. For example, fluid conduits herein may include one or more membrane layers, at least an innermost portion of which at least partially define the fluid conduit. For example, any of the fluid conduit layers described herein are expressly incorporated by reference herein. In the embodiment shown in figure 291, fluid conduit 2912 can include one or more layers of material 2913, at least an inner surface of which at least partially defines the fluid conduit. Reference will be made to layer 2913, but it is understood "layer" 2913 may include one or more layers of material secured together in a variety of ways and using a variety of techniques.

Layer 2913 can be secured to one or more pump portion support members (e.g., expandable scaffold(s)), which can be configured and adapted to provide radial support to the fluid conduit.

In the embodiment of figure 291, layer 2913 includes a proximal end with a configuration that causes one or more of a decrease fluidic losses or an increase in performance at the pump outflow. Layer 2913 is an example of a layer that has a proximal end that has a non-circular configuration. Layer 2913 is an example of a layer that has a proximal end region with a configuration that is non-cylindrical. In this merely exemplary embodiment, layer 2913 includes alternating protrusions and depressions, which help define and create the alternating protrusions and depressions of the fluid conduit proximal end. Any of the the fluid conduit layers (e.g., layer 2913) may have a proximal end with a configuration of any of the fluid conduit proximal ends described herein (e.g., sawtooth).

A proximal region of any of the support members herein (e.g., expandable scaffolds) may also have a proximal end with a configuration that is non-circular, such as any of the configurations herein. For example, any of the support members herein may have a proximal end with a configuration that includes protrusions and depressions, which may alternative around the support member.

The proximal end of any of the layers herein (e.g., layer 2913) may follow a configuration of a expandable and collapsable support member proximal end. A proximal end of the layer and a proximal end of the support member can have configurations that are the same or substantially the same (e.g., the same but for very minor differences). For example, in FIG. 29, a proximal end of layer 2913 can have a configuration that follows a configuration of a proximal end of a support member (not specifically shown, but can be any of the support members described herein). For example, layer 2913 can have a proximal end with a non-circular configuration (an example of which is shown) that follows a non-circular configuration of a proximal end of a support member or scaffold.

A layer proximal end may follow a support scaffold proximal end for at least 180 around the support member, optionally at least 200 degrees, optionally at least 220 degrees, optionally at least 240 degrees, optionally at least 270 degrees, optionally at least 300 degrees, optionally at least 330 degrees, and it may follow the support member for a fully 360 degrees.

In some embodiments the layer may have a non-circular proximal end (e.g., such as shown in FIG. 29) and the support member may have a circular end. For example, some layers may be able to provide enough radial support alone without having a support member that has the exact same proximal end configuration of the layer.

In embodiments in which the fluid conduit proximal end includes protrusions (e.g., protrusions 2931), not all of the protrusions necessarily extend to the same location proximally For example, as shown in exemplary FIG. 29, some of the protrusions 2931 extend further proximally than others. In this merely exemplary embodiment, protrusions from which a strut 2916 extends extend further proximally than protrusions 2931 from which a strut 2916 does not extend.

Additionally, not all of the protrusions need to have same configuration. For example, as shown in FIG. 291, some protrusions have a flatter peak than others. In this merely exemplary embodiment, some protrusions that are disposed radially in between struts 2916 extend to the same extent proximally Exemplary features of struts 2916 are described herein, and any feature or use thereof is incorporated by reference into this embodiment.

The pump portion may include one or more impellers, examples of which are disclosed herein. Impeller 2914 may be a proximal pump impeller, and the pump may also include a distal impeller, for example, disposed further distally than the proximal impeller.

The configuration of proximal end 2930 may also help with resheathing and collapsing towards a smaller delivery profile, and it may ease one or more aspects of the manufacture of the pump portion.

Catheter blood pumps herein may include or otherwise be used with an outer sheath 3010 or sheath-like member (any of which may be referred to herein as "sheath") in which an expandable pump portion of the blood pump may be delivered. Relative axial movement between the expandable pump portion 3002 and the sheath 3010 (e.g., sheath proximal retraction) allows the pump to expand when no longer constrained radially by the sheath.

Some aspects of the disclosure herein include catheter pumps in which a sheath 3010 is positioned and/or adapted to be positioned relative to an operational impeller 3004 to improve flow at a pump outflow 3005, including without limitation, reducing recirculation and negative flow effects at an outflow of the pump compared to alternative design in which the sheath 3010 is not so positioned. The sheath may be functionally similar to the expandable/deployable flow diverters at the pump outflow that are described herein. In this context, however, the structure that provides the function is disposed in or carried by the axially movable sheath.

With the use of some other expandable pump portions herein, an outer sheath is retracted proximally relative to the pump such that its effects on flow at the outflow are negligible. In FIGS. 30 and 31, however, the distal end 3007 of sheath 3010 is shown relatively closer to outflow 3005 (and thus also closer to the shroud 3006 and impeller 3004), which increases the diameter that the fluid sees at the pump outflow 3005 (compared to a sheath that retracted further proximally than that which is shown in FIG. 30). The sheath 3010 in the position shown at the outflow 3005 in FIG. 30 occupies volume at the outflow, helping reduce swirl and backflow (reduces recirculation), compared to designs with the sheath further proximally, all other features being the same. An exemplary scaffold and membrane of shroud 3006 of expandable pump portion 3002 is also shown. An exemplary vessel in which the pump portion 3002 may be positioned in also shown, which may be an ascending aorta. The strut region shown may include any of the struts described herein.

FIG. 31 illustrates an alternative catheter pump 3102 that includes a pump portion 3102 and an expandable flow diverter 3130, which may have any feature of any of the flow diverters elsewhere herein. In this example, the flow diverter 3130 is part of or carried by a distal end region 3107 of sheath 3010, optionally at the distal end of the sheath or very closer thereto, as shown. The expandable flow diverter 3130 may be one or more layers of material sealed at distal and proximal ends to sheath components, having an interior volume being in fluid communication with an external fluid reservoir such that fluid delivery into the flow diverter 3130 expands the flow diverter to the position shown in dotted lines in FIG. 31. The expanded configuration as shown may have any of the structural or functional characteristics of any of the expandable flow diverters herein, such as the relative slopes of the distal and proximal surfaces. The flow diverter

3130 may comprise a polymeric material, and may be deformable for inflation. The flow diverter 3130 may inflate towards or to a preformed or pre-set configuration, such as the shape shown in FIG. 31, which may help the flow diverter assume a desired expanded configuration. Outflow 305 is also shown.

In any of the examples herein, the distal end of the sheath may be disposed 0.1 inch-1 inch proximal to a proximal end of the shroud when the impeller(s) is operated to move blood through the fluid conduit, and in some embodiments 0.1 inch-0.9 inch, and in some embodiments 0.1 inch-0.8 inch, and in some embodiments 0.1 inch-0.7 inch, and in some embodiments 0.1 inch-0.6 inch, and in some embodiments 0.1 inch-0.5 inch, and in some embodiments 0.1 inch-0.4 inch.

In any of the examples herein, an expandable flow diverter (such as flow diverter 3130 is shown in FIG. 31) part of or carried by the an outer sheath may have a distal end that is disposed 0.1 inch-1 inch proximal to a proximal end of the shroud when the impeller(s) is operated to move blood through the fluid conduit, and in some embodiments 0.1 inch-0.9 inch, and in some embodiments 0.1 inch-0.8 inch, and in some embodiments 0.1 inch-0.7 inch, and in some embodiments 0.1 inch-0.6 inch, and in some embodiments 0.1 inch-0.5 inch, and in some embodiments 0.1 inch-0.4 inch.

In use, an outer sheath may be retracted proximally relative to an expandable pump to allow and/or cause the expandable pump to expand. In some uses, the sheath may be retracted such that a distal end region is at or adjacent a pump outflow, such as shown in FIGS. 30 and 31. Positioning the distal end of the sheath at the desired position may be accomplished in a variety of ways. For example, the position of the sheath may be detectable under radiographic visualization using one or more markers on one or more portions of the blood pump, such as a marker near a distal end of the sheath. The sheath can be retracted until the distal end is at a desired position relative to the expandable pump and/or shroud and/or impeller. The pump may include a handle that is configured to facilitate relative movement of the sheath.

In some embodiments the pump may be adapted with a control feature to limit proximal movement of the sheath after a certain amount of proximal movement, which automatically positions the sheath distal end and/or distal end region at a desired position at or adjacent the pump outflow and prevents further proximal retraction. This may be referred to herein as a movement limiter. The sheath movement limiter feature may be incorporated into the handle of the blood pump, for example. For example, a handle can include a sheath actuator that is operatively coupled with the sheath, such that actuation of the actuator causes proximal movement of the sheath, but proximal movement is limited to a certain axial distance relative to a distal end of the sheath when the sheath is in a sheath delivery position. This type of controlled sheath movement and controlled sheath positioning at the outflow may be referred to herein as a stop, a sheath movement limiter, a sheath outflow positioner, or other similar phrase that imparts the function to cause the distal end of the sheath to be positioned at or adjacent a pump outflow, such as any of the exemplary distances provided herein (e.g., 0.1 inch to 1 inch from a proximal end of a fluid conduit).

The pump may comprise an outer sheath movement resister that is adapted to resist proximal movement of the outer sheath. A sheath movement resist feature may be incorporated into the handle of the blood pump, for example.

For example, a handle can include a sheath actuator that is operatively coupled with the sheath, such that actuation of the actuator causes proximal movement of the sheath, but proximal movement is resisted because of the movement resister after a distal end of the sheath has moved a certain distance proximally from an initial delivery position. A movement resister may cause a tactile feedback to a user (e.g., physician) to alert the user that the distal end of the sheath is in a desired position. For example, the user may feel resistance when trying to further actuate a handle actuator. Any of the movement resisters herein may allow for continued proximal sheath movement, but may be able to alert the user of the position of the distal end of the sheath without necessarily automatically stopping sheath movement. The user may decide whether or not to cease movement of the sheath after the resistance.

FIG. 32 illustrates a portion of an exemplary pump 3202 similar to that shown in FIGS. 30 and 31 and which may include any aspect thereof. An exemplary advantage of positioning the sheath 3210 near the outflow 3205 as shown is that the sheath may optionally include or carry structural components that may benefit from being at or adjacent the outflow. For example without limitation, FIG. 32 illustrates a pump 3202 with an exemplary sensor 3240 carried by the sheath distal end region 3207, as shown. In some embodiments sensor 3240 may be within 3 inches from a sheath distal end 3207, such as within 2 inches from the sheath distal end, or within 1 inch from the sheath distal end.

The sensor may be, for example without limitation, a flow sensor or a pressure sensor. A sensor may be used to sense flow and/or pressure, and the output therefrom may be used in a variety of ways, such as controlling one or more aspects of the pump (e.g., speed, axial position, etc.). The sensor may be considered a "proximal" pump sensor, and the pump may also include one or more distal sensors that are disposed distal to the shroud proximal end, such as at or adjacent the pump inflow. A distal sensor and a proximal sensor may be used to sense flow and/or pressure, and the output therefrom may be used in a variety of ways, such as controlling one or more aspects of the pump (e.g., speed, axial position, etc.). Sensor 3240 as shown in FIG. 32 may be in electrical communication with electronics extending proximally along and/or within the sheath, optionally extending to a handle portion of the blood pump. The electronics may be in communication with an external console or other component that is adapted to receive the information transmitted from the sensor. A sensor disposed on or carried by the sheath as shown in exemplary FIG. 32 may provide an exemplary benefit of sensor electronic routing on or carried by the sheath.

The invention claimed is:

1. A method of directing outflow of an intravascular blood pump, comprising:

expanding a collapsible blood pump from a collapsed configuration at a location within a subject, the expanding step including expanding a collapsible fluid conduit from a collapsed configuration and expanding one or more collapsible impellers, the one or more impellers disposed at least partially within the collapsible fluid conduit;

expanding an expandable flow diverter into an expanded configuration in which a flow diverting surface of the expandable flow diverter is axially positioned completely proximal to a proximal end of the fluid conduit and proximal to the one or more impellers; and rotating the at least one impeller to cause blood to move from a fluid conduit distal end towards the fluid conduit proximal end.

2. The method of claim 1, wherein the flow diverter is rotationally uncoupled from the one or more impellers.

3. The method of claim 1, wherein a radial dimension of the flow diverting surface increases in an axial distal-to-proximal direction.

4. The method of claim 1, wherein the flow diverter includes a proximal surface proximal to the flow diverting surface, the proximal surface having a radial dimension that decreases in an axial distal-to-proximal direction.

5. The method of claim 1, wherein increasing the radial flow component also causes blood to flow between a plurality of pump proximal struts that extend proximally from the fluid conduit.

6. The method of claim 5, wherein the plurality of struts are coupled to the flow diverter along a portion of each of the struts, and wherein causing blood to flow between the plurality of struts comprises causing blood to flow between the plurality of struts at locations where the plurality of struts are not coupled to the flow diverter.

7. The method of claim 1, wherein expanding the flow diverter reduces a blood re-circulation zone at a location proximal to the fluid conduit proximal end.

8. The method of claim 1, wherein expanding a collapsible blood pump includes expanding one of the one or more impellers into an expanded position in which a portion of the one impeller extends proximally relative to the proximal end of the fluid conduit.

9. The method of claim 1, wherein expanding the expandable flow diverter comprises allowing the flow diverter to at least partially self-expand.

10. The method of claim 1, wherein expanding the expandable flow diverter comprises inflating the flow diverter with a fluid.

11. The method of claim 1, further comprising expanding one or more proximal fluid conduit struts, wherein expanding the one or more proximal struts causes the flow diverter to at least partially expand and/or help prevent the flow diverter from completely collapsing.

12. The method of claim 1, wherein expanding the expandable flow diverter comprises expanding the flow diverter into a bulbous expanded configuration.

13. The method of claim 1, wherein expanding the flow diverter comprises expanding the expandable flow diverter into an expanded configuration in which a radially outermost dimension of the flow diverter is at least 50% of a radially outermost dimension of the impeller, optionally at least 55%, optionally at least 60%, optionally at least 65%, optionally at least 70%, optionally at least 75%, optionally at least 80%, optionally at least 85%, optionally at least 90%, optionally at least 95%, optionally at least 100%, and optionally no more than 300%.

14. A method of directing outflow of an intravascular blood pump >comprising:

expanding a collapsible blood pump from a collapsed configuration at a location within a subject, the expanding step including expanding a collapsible fluid conduit from a collapsed configuration, expanding one or more collapsible impellers disposed at partially within the collapsible fluid conduit, and expanding one or more proximal fluid conduit struts;

expanding an expandable flow diverter into an expanded configuration in which at least a portion of the flow diverter is disposed proximal to the fluid conduit and at least a portion of the flow diverter is secured to the plurality of struts, whereby expanding the one or more proximal fluid conduit struts causes the flow diverter to at least partially expand towards the expanded configuration; and rotating the at least one impeller to cause blood to move from a fluid conduit distal end towards the fluid conduit proximal end.

15. The method of claim 14, wherein expanding the flow diverter further comprises allowing the flow diverter to self-expand to some extent due to a material of the flow diverter.

16. The method of claim 14, wherein expanding the flow diverter further comprises advancing a fluid into an inner volume defined by the flow diverter.

17. A method of directing outflow of an intravascular blood pump comprising:

expanding a collapsible blood pump from a collapsed configuration at a location within a subject, the expanding step including expanding a collapsible fluid conduit from a collapsed configuration, expanding one or more collapsible impellers disposed at partially within the collapsible fluid conduit, and optionally expanding one or more proximal fluid conduit struts;

expanding an expandable flow diverter into an expanded configuration in which at least a portion of the flow diverter is disposed proximal to the fluid conduit, wherein expanding the flow diverter comprises expanding the expandable flow diverter into an expanded configuration in which a radially outermost dimension of the flow diverter is at least 25% of a radially outermost dimension of the one or more impellers, optionally at least 50%, optionally at least 55%, optionally at least 60%, optionally at least 65%, optionally at least 70%, optionally at least 75%, optionally at least 80%, optionally at least 85%, optionally at least 90%, optionally at least 95%, optionally at least 100%, and optionally no more than 300%; and rotating the at least one impeller to cause blood to move from a fluid conduit distal end towards the fluid conduit proximal end.

* * * * *